(12) United States Patent
Adam et al.

(10) Patent No.: US 6,407,094 B1
(45) Date of Patent: Jun. 18, 2002

(54) GLUTAMATE RECEPTOR ANTAGONISTS

(75) Inventors: Geo Adam, Schopfheim (DE);
Alexander Alanine, Riedisheim (FR);
Erwin Goetschi, Reinach (CH);
Vincent Mutel, Mulhouse (FR);
Thomas Johannes Woltering, Weil am Rhein (DE)

(73) Assignee: Hoffmann-la Roche Inc., Nutley, NJ (US)

( * ) Notice: Subject to any disclaimer, the term of this patent is extended or adjusted under 35 U.S.C. 154(b) by 0 days.

(21) Appl. No.: 09/687,240

(22) Filed: Oct. 13, 2000

(30) Foreign Application Priority Data

Oct. 15, 1999 (EP) .............................................. 99120520

(51) Int. Cl.[7] .................... C07D 243/12; C07D 409/04; C07D 405/04; C07D 417/04; A61K 31/55
(52) U.S. Cl. ........................................ 514/221; 540/517
(58) Field of Search .......................... 540/517; 514/221

(56) References Cited

FOREIGN PATENT DOCUMENTS

| WO | WO 97/05109 | 2/1997 |
|----|-------------|--------|
| WO | WO 99/26927 | 6/1999 |

OTHER PUBLICATIONS

J. Org. Chem., 1973, vol. 38, p. 3224.
Wilson, J. et al., Aust. J. Chem. 1983, vol. 36, pp. 2317–2325.
Tetr. Lett. 1997, vol. 38, p. 3841–3844.
Tetr. Lett. 1993 vol. 34, pp. 7595–7598.
Bull. Chem. Soc. Jpn. 1983, vol. 56 p. 3855–3856.
J. Org. Chem. 1998, vol. 63 pp. 8551–8553.
Tetr. Lett. 1984, vol. 25, p. 839–842.
Synth. Commun. 1985, vol. 15, p. 1039–1049.
J. Med. Chem. 1987 vol. 30 pp. 1342–1347.
Tetrahedron 1984 vol. 40, p. 2985–2988.
Chem. Pharm. Bull. 1983 vol. 31 p. 1896–1901.
Tetrahedron Lett. 1998 vol. 39 p. 2253–2256.
Journal of Antibiotics 1978, vol. 31 pp. 1245–1251.
Tetrahedron Letters, 1995 vol. 36 pp. 7115–7118.
Rao et al., *Synthesis of H–1,5–Benzodiazepin–2(3H)–ones from 5(4H)–Isoxazolone, a Heterocyclic Bifunctional C–3 Synthon*, synthesis, vol. . 5, pp. 446–448 (1992).

*Primary Examiner*—Bruck Kifle
(74) *Attorney, Agent, or Firm*—George W. Johnston; Patricia S. Roche-Tramaloni; Arthur D. Dawson

(57) ABSTRACT

The present invention relates to compounds of with a base structure of formula 1

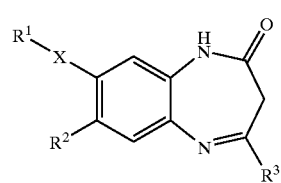

The compounds of formula I are shown to have activity as metabotropic glutamate receptor antagonists.

7 Claims, No Drawings

GLUTAMATE RECEPTOR ANTAGONISTS

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

SUMMARY OF THE INVENTION

The present invention relates to compounds of the general formula I

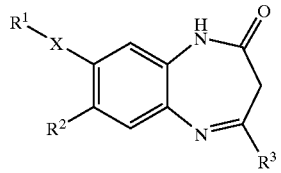

These compounds have been discovered to act as metabotropic glutamate receptor antagonists and accordingly are useful for the treatment of a range of neurological disorders, including psychosis, schizophrenia, Alzheimer's and other cognitive and memory disorders.

Objects of the present invention are compounds of formula I and their pharmaceutically acceptable salts per se and as pharmaceutically active substances, their manufacture, medicaments based on a compound in accordance with the invention and their production, as well as the use of the compounds in accordance with the invention in the control or prevention of neurologial disorders, and, respectively, for the production of corresponding medicaments.

DETAILED DESCRIPTION

The present invention relates to compounds of formula I

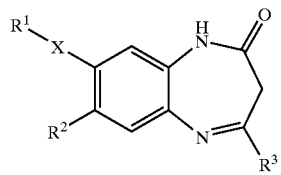

wherein

X is a single bond or an ethynediyl group, wherein,

In case X is a single bond, $R^1$ is halogen or phenyl which is optionally substituted with halogen, lower alkyl, halo-lower alkyl, lower alkoxy, halo-lower alkoxy, or cyano;

In case X is an ethynediyl group, $R^1$ is phenyl, optionally substituted with halogen, lower alkyl, halo-lower alkyl, lower cycloalkyl, lower alkoxy or halo-lower alkoxy;

$R^2$ is halogen; hydroxy; lower alkyl; lower halo-alkyl; lower alkoxy; hydroxymethyl; hydroxyethoxy; lower alkoxy-(ethoxy)$_n$ (n=1 to 4); lower alkoxymethyl; cyanomethoxy; morpholine-4-yl; thiomorpholine-4-yl; 1-oxothiomorpholine-4-yl; 1,1-dioxothiomorpholine-4-yl; 4-oxo-piperidine-1-yl; 4-alkoxy-piperidine-1-yl; 4-hydroxy-piperidine-1-yl; 4-hydroxyethoxy-piperidine-1-yl; 4-lower alkyl-piperazine-1-yl; alkoxycarbonyl; 2-dialkylamino-ethylsulfanyl-; N,N-bis lower alkylamino lower alkyl; carbamoylmethyl; alkylsulfonyl; lower alkoxycarbonyl-lower alkyl; alkylcarboxy-lower alkyl; carboxy-lower alkyl; alkoxycarbonylmethylsulfanyl; carboxymethylsulfanyl; 1,4-dioxa-8-aza-spiro[4.5]dec-8-yl; carboxy-lower alkoxy; cyano-lower alkyl; 2,3-dihydroxy-lower alkoxy; carbamoylmethoxy; 2-oxo-[1,3]-dioxolan-4-yl-lower alkoxy; (2-hydroxy-lower alkyl)-lower alkyl amino; hydroxycarbamoyl-lower alkoxy; 2,2-dimethyl-tetrahydro-[1,3]dioxolo[4,5c]-pyrrol-5-yl; lower alkoxy-carbamoyl-lower alkoxy; 3R-hydroxy-pyrrolidin-1-yl; 3,4-dihydroxy-pyrrolidin-1-yl; 2-oxo-oxazolidin-3-yl; lower alkyl-carbamoylmethoxy; or aminocarbamoyl-lower alkoxy;

$R^3$ is a 5 or 6 membered aryl or heteroaryl which are optionally substituted by halogen; cyano; nitro; azido; hydroxy; carboxy; morpholine-4-carbonyl; carbamoyl; thiocarbamoyl; N-hydroxycarbamoyl; trimethylsilylethynyl; or lower alkyl; lower alkoxy; halo-lower alkyl; 4-lower alkyl-piperazine-1-carbonyl; lower alkylcarbamoyl which are optionally substituted by amino, lower alkylamino, acylamino, oxo, hydroxy, lower alkoxy, lower alkylthio, or carboxy which is optionally esterified or amidated; or an optionally substituted five-membered aromatic heterocycle, which may be optionally substituted by amino, lower alkylamino, acylamino, oxo, hydroxy, lower alkoxy, lower alkylthio, or carboxy which is optionally esterified or amidated, or lower alkyl which is optionally substituted by halogen, amino, lower alkylamino, acylamino, hydroxy, lower alkoxy, lower alkylthio, acyloxy, lower alkenoyl, lower alkylsulfinyl, lower alkylsulfonyl, cycloalkylsulfinyl, cycloalkylsulfonyl, hydroxyimino, alkoxyimino, carboxy which is optionally esterified or amidated, lower alkenyl, oxo, cyano, carbamoyloxy, sulfamoyl which is optionally substituted by lower alkyl, or amidino which is optionally substituted by lower alkyl, —C(NRR')=NR" (where R, R' and R" are hydrogen or lower alkyl)
and their pharmaceutically acceptable addition salts.

It has surprisingly been found that the compounds of formula I are metabotropic glutamate receptor antagonists. Compounds of formula I are distinguished by valuable therapeutic properties.

The compounds of the present invention can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral scherosis (ALS), dementia caused by AIDS, eye injuries, retinopathy, indiopathic parkinsonism or parkinsonism caused by medicaments as well as conditions which lead tn glutamate-deficiency functions, such as e.g. muscle spasms, convulsions, migraine, urinary incontinence, nicotine addiction, opiate addiction, anxiety, vomiting, dyskinesia and depressions.

Objects of the present invention are compounds of formula I and their pharmaceutically acceptable salts per se and as pharmaceutically active substances, their manufacture, medicaments based on a compound in accordance with the invention and their production, as well as the use of the compounds in accordance with the invention in the control or prevention of illness of the aforementioned kind, and, respectively, for the production of corresponding medicaments.

Preferred compounds of formula I in the scope of the present invention are those in which $R^3$ is phenyl substituted in meta position by cyano; halogen; or imidazolyl which is optionally substituted by lower alky or methylsulfanyl; 1,2,3-triazolyl; 1,2,4-triazolyl; or isoxazolyl which is optionally substituted by lower alkyl.

The following are examples of such compounds:

3-(8-Chloro-4-oxo-7-phenylethynyl-4,5-dihydro-3H-benzo[b][1,4]diazepin-2-yl)-benzonitrile
3-[8-(4-Methyl-piperazin-1-yl)-4-oxo-7-phenylethynyl-4,5-dihydro-3H-benzo[b][1,4]diazepin-2-yl]-benzonitrile;
3-(8-Chloro-4-oxo-7-phenyl-4,5-dihydro-3H-benzo[b][1,4]diazepin-2-yl)-benzonitrile;
[4-(3-Cyano-phenyl)-2-oxo-8-phenylethynyl-2,3-dihydro-1H-benzo[b][1,4]diazepin-7-ylsulfanyl]-acetic acid methyl ester;
2-[4-(3-Cyano-phenyl)-2-oxo-8-phenylethynyl-2,3-dihydro-1H-benzo[b][1,4]diazepin-7-yl]-acetamide;
3-(8-Methoxy-4-oxo-7-phenylethynyl-4,5-dihydro-3H-benzo[b][1,4]diazepin-2yl)-benzonitrile
3-(8-Cyanomethyl-4-oxo-7-phenylethynyl-4,5-dihydro-3H-benzo[b][1,4]diazepin-2-yl)-benzonitrile;
4-(3-Iodo-phenyl)-7-(2-methoxy-ethoxy)-8-phenylethynyl-1,3-dihydro-benzo[b][1,4]diazepin-2-one;
4-(3-Imidazol-1-yl-phenyl)-7-(2-methoxy-ethoxy)-8-phenylethynyl-1,3-dihydro-benzo[b][1,4]diazepin-2-one;
[RS]-3-[4-Oxo-8-(2-oxo-[1,3]dioxolan-4-ylmethoxy)-7-phenylethynyl-4,5-dihydro-3H-benzo[b][1,4]diazepin-2-yl]-benzonitrile;
7-Hydroxymethyl-4-(3-imidazol-1-yl-phenyl)-8-phenylethynyl-1,3-dihydro-benzo[b][1,4]diazepin-2-one;
[4-(3-Imidazol-1-yl-phenyl)-2-oxo-8-phenylethynyl-2,3-dihydro-1H-benzo[b][1,4]diazepin-7-yloxy]-acetonitrile;
8-(4-Fluoro-phenylethynyl)-7-hydroxymethyl-4-(3-imidazol-1-yl-phenyl)-1,3-dihydro-benzo[b][1,4]diazepin-2-one;
7-(2-Hydroxy-ethoxy)-4-(3-imidazol-1-yl-phenyl)-8-phenylethynyl-1,3-dihydro-benzo[b][1,4]diazepin-2-one;
8-(4-Fluoro-phenyl)-7-[4-(2-hydroxy-ethoxy)-piperidin-1-yl]-4-(3-imidazol-1-yl-phenyl)-1,3-dihydro-benzo[b][1,4]diazepin-2-one;
8-(4-Fluoro-phenyl)-7-hydroxy-4-(3-imidazol-1-yl-phenyl)-1,3-dihydro-benzo[b][1,4]diazepin-2-one;
8-(2-Fluoro-phenyl)-7-methoxy-4-[3-(2-methyl-imidazol-1-yl)-phenyl]-1,3-dihydro-benzo[b][1,4]diazepin-2-one;
8-(2-Fluoro-phenyl)-7-hydroxy-4-(3-[1,2,3]triazol-1-yl-phenyl)-1,3-dihydro-benzo[b][1,4]diazepin-2-one;
8-(2-Fluoro-phenyl)-7-hydroxy-4-[3-(2-methyl-imidazol-1-yl)-phenyl]-1,3-dihydro-benzo[b][1,4]diazepin-2-one;
8-(2-Fluoro-phenyl)-7-hydroxy-4-[3-(2-methylsulfanyl-imidazol-1-yl)-phenyl]-1,3-dihydro-benzo[b][1,4]diazepin-2-one;
8-(2,5-Difluoro-phenyl)-7-methoxy-4-(3-[1,2,3]triazol-1-yl-phenyl)-1,3-dihydro-benzo[b][1,4]diazepin-2-one;
8-(2-Fluoro-phenyl)-7-hydroxy-4-[3-(3-methyl-isoxazol-5-yl)-phenyl]-1,3-dihydro-benzo[b][1,4]diazepin-2-one;
3-[7-(2,5-Difluoro-phenyl)-8-hydroxy-4-oxo-4,5-dihydro-3H-benzo[b][1,4]diazepin-2-yl]-benzonitrile;
8-(4-Fluoro-phenylethynyl)-7-hydroxy-4-(3-imidazol-1-yl-phenyl)-1,3-dihydro-benzo[b][1,4]diazepin-2-one; and
8-(4-Fluoro-phenylethynyl)-7-hydroxy-4-(3-[1,2,3]triazol-1-yl-phenyl)-1,3-dihydro-benzo[b][1,4]diazepin-2-one.

Compounds of formula 1, wherein $R^3$ is thiophenyl, preferably thiophen-2-yl, which is optionally substituted by cyano or halogen; or $R^3$ is pyridinyl, preferably pyridin-4-yl, which is optionally substituted in 2-position by cyano or halogen, or wherein $R^3$ is thiazolyl which is optionally substituted in 2-position with imidazolyl or 4-methylimidazolyl, are also preferred.

The following compounds are particularly preferred:

5-[7-(2-Fluoro-phenyl)-8-methoxy-4-oxo-4,5-dihydro-3H-benzo[b][1,4]diazepin-2-yl]-thiophene-2-carbonitrile;
2-[7-(2-Fluoro-phenyl)-8-hydroxy-4-oxo-4,5-dihydro-1H-benzo[b ][1,4]diazepin-2-yl]-thiophene-3-carbonitrile;
4-[7-(2-Fluoro-phenyl)-8-methoxy-4-oxo-4,5-dihydro-3H-benzo[b][1,4]diazepin-2-yl]-pyridine-2-carbonitrile;
4-[7-(4-Fluoro-phenyl)-8-hydroxy-4-oxo-4,5-dihydro-3H-benzo[b][1,4]diazepin-2-yl]-pyridine-2-carbonitrile;
4-[7-(2-Fluoro-phenyl)-8-hydroxy-4-oxo-4,5-dihydro-3H-benzo[b][1,4]diazepin-2-yl]-pyridine-2-carbonitrile; and
8-(2-Fluoro-phenyl)-4-[2-(4-methyl-imidazol-1-yl)-thiazol-4-yl]-1,3-dihydro-benzo[b][1,4]diazepin-2-one.

All tautomeric forms of the compounds of the invention are also embraced herewith.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower cycloalkyl" used in the present description denotes cyclic saturated hydrocarbon residues with 3–5 carbon atoms, preferably with 3 carbon atoms, such as cyclopropyl.

The term "lower alkoxy" denotes a lower alkyl residue in the sense of the foregoing definition bonded via an oxygen atom.

The term "halogen" embraces fluorine, chlorine, bromine and iodine.

The term "5 or 6 membered aryl or heteroaryl" embraces phenyl, thiophenyl, pyridine, partially hydrated pyridine.

The expression "five-membered aromatic heterocycle" embraces, furan, thiazol, imidazol, pyrazol, 1,3-thiazol, 1,3-oxazol, 1,2-oxazol, 1,2-thiazol, 1,2,3-triazol, 1,2,4-triazol, 1,2,4-oxadiazol, 1,2,3-oxadiazol, 1,2,4-thiadiazol, 1,2,3-thiadiazol and tetrazol.

The compounds of formula I and their pharmaceutically acceptable salts can be manufactured according to the following methods:

Scheme A

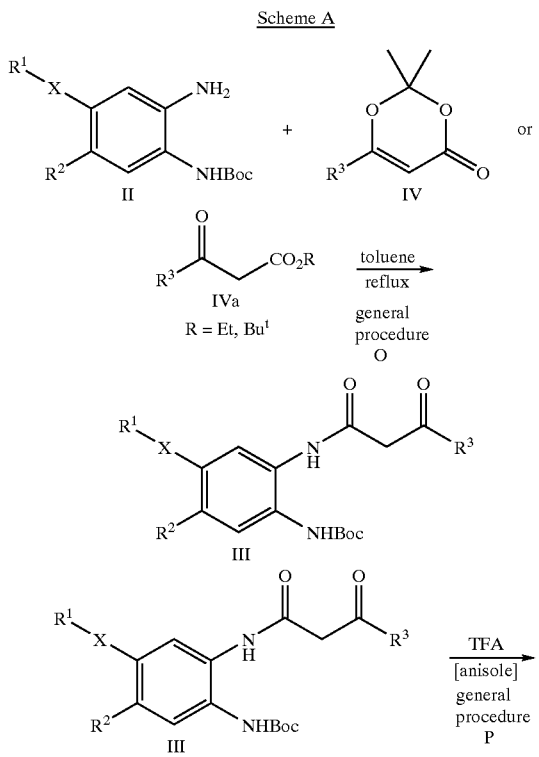

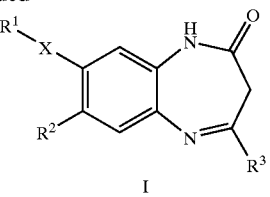

I

According to scheme A, compounds of formula I, in which X, $R^1$, $R^2$ and $R^3$ are as described above, can be prepared from compounds of formula II via an acylation-deprotection-cyclization sequence:

For example reacting compounds of formula II with a dioxinone IV, in which $R^3$ is as described above, in an inert solvent such as toluene or xylene at elevated temperatures, preferably between 80° C. and 160° C. gives rise to compounds of formula III.

Alternatively, compounds of formula III can also be prepared by for example reaction of a compound of formula II with a β-ketoester (formula IVa), in which $R^3$ is as described above using the same conditions as described for the reaction with the dioxinones.

Afterwards, cleaving the BOC protecting group in compounds of formula III and concomitant cyclization of the deprotected compound yields the desired compounds of formula I. Any other suitable amino protecting group, such as e.g. Fmoc or benzyloxycarbonyl (Z), can be alternatively used instead of the BOC group.

The deprotection-cyclization step can be carried out by treating the compounds of formula III with for example a Bronsted acid such as trifluoroacetic acid in an inert solvent such as dichloromethane (DCM). The reaction is preferably carried out at temperatures between 0° C. and 50° C. It may be advantageous to use also anisole or 1,3-dimethoxybenzene as a carbocation scavenger in the reaction mixture.

Scheme B

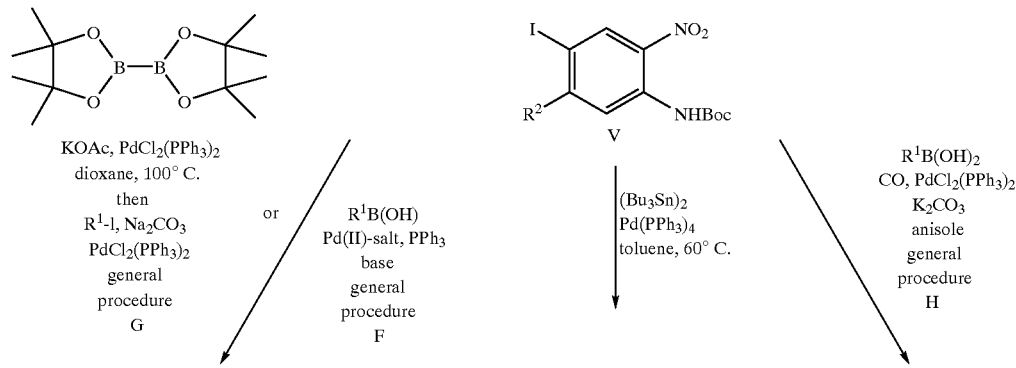

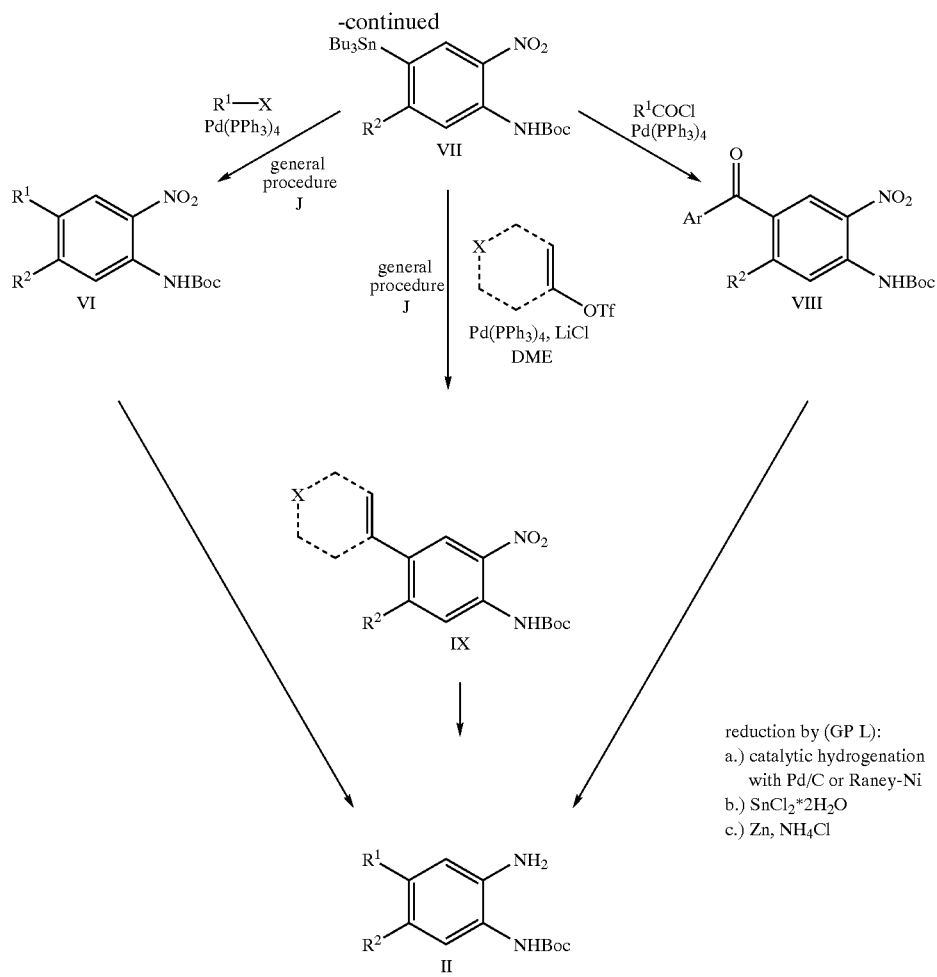

According to scheme B, compounds of formula II in which $R^1$ is as described above for compounds where X is a single bond and $R^2$ is as described above, can be prepared by different routes depending on the nature of $R^2$ from the iodo-compounds of formula V, in which $R^2$ is as described above. As shown in scheme B, the key steps are coupling reactions of Suzuki-and Stille-type in presence or absence of carbonmonoxide. The exact conditions for the respective compounds of formula II can be found in the experimental part.

Compounds of formula V, in which $R^2$ is as described above, can be prepared by different routes depending on the individual residue $R^2$:

Scheme C

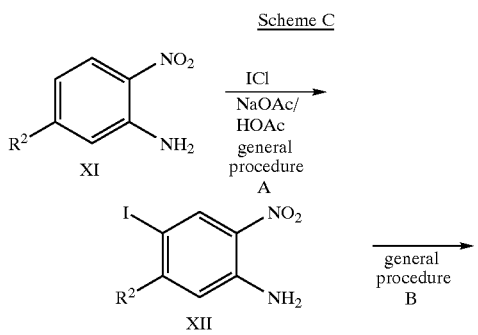

-continued

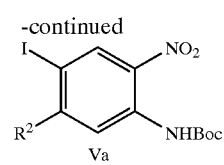

GP B, method a: diphosgene, EtOAc, 77° C.; then t-BuOH
GP B, method b: Boc$_2$O, Cs$_2$CO$_3$, 2-butanone, 52° C.
GP B, method c: i) Boc$_2$O, DMAP, THF; ii) TFA, DCM, 0° C.

As shown in scheme C, compounds of formula Va, in which $R^2$ is lower alkyl, halogen or alkoxycarbonyl, can be prepared from the known compounds of formula XI by iodination and subsequent protection of the synthetic intermediates with formula XII.

The iodination step can be carried out by for example using iodine monochloride in acetic acid in the presence of sodium acetate. The reaction can be for example carried out at temperatures between 20° C. and 80° C.

The protection of the amino function can be achieved by for example reacting compounds of formula XII with di-tert.-butyl-carbonate in the presence of a base such as cesium carbonate. The reaction can be carried out in polar solvents such as acetone or butanone and the like at temperatures between 20° C. and 60° C.

As shown in scheme D, compounds of formula Vb and Vc, in which $R^2$ is attached via a sulfur- or nitrogen-atom ($R^2$ represents for example morpholin-4-yl; thiomorpholino- 4-yl; dialkylamino; carboxymethylsulfanyl etc), respectively, can be prepared from the intermediate XIII by a nucleophilic substitution reaction with the respective amines or mercaptanes in the presence of a suitable base.

Scheme D

Nitrogen nucleophiles

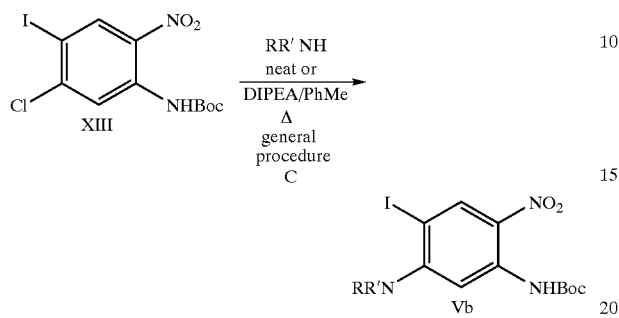

Sulfur nucleophiles

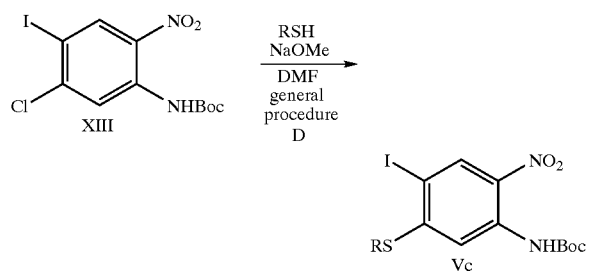

The reaction is preferably carried out in a polar, aprotic solvent such as dimethyl formamide, N-methyl-pyrrolidone or dimethyl sulfoxide and the like. The base can be selected from the sterically hindered amines such as Hünig's base, alkoxides such as sodium methoxide and tert.-butoxide, or hydrides such as sodium hydride. The reaction can be performed at temperatures between 20° C. and 110° C., depending on the individual compounds to be synthesized.

Compounds of formula Vd in which $R^2$ is attached via an oxygen atom ($R^2$ represents for example lower alkoxy, lower halo-alkoxy, lower cyclo-alkoxy, lower alkoxy-lower alkoxy; etc.) can be prepared as for example shown in scheme E:

Scheme E

Oxygen nucleophiles

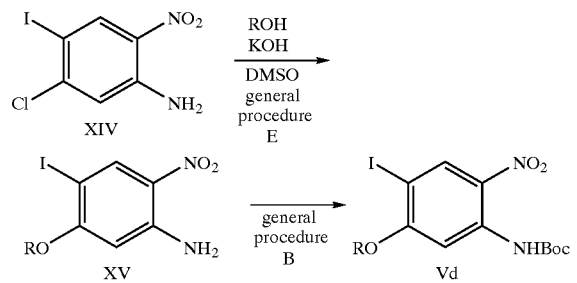

GP B, method a: diphosgene, EtOAc, 77° C.; then t-BuOH
GP B, method b: Boc₂O, Cs₂CO₃, 2-butanone, 52° C.
GP B, method c: i) Boc₂O, DMAP, THF; ii) TFA, DCM, 0° C.

Oxygen alkylation

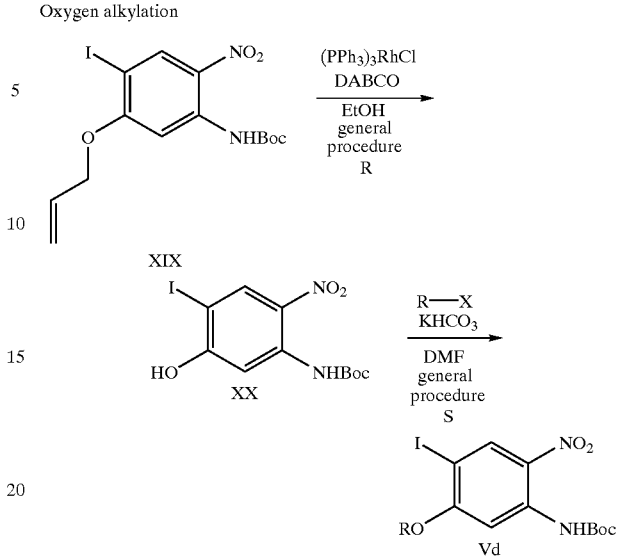

by a nucleophilic aromatic substitution reaction with the respective alcohol in the presence of a suitable base and subsequent protection of the amino function. The base can be selected from the class of Bronsted bases such as potassium hydroxide and the like. The reaction is preferably carried out in a polar, aprotic solvent such as dimethyl formamide, N-methyl-pyrrolidone or dimethyl sulfoxide and the like at temperatures between 20° C. and 100° C.

The protection of the amino function can be achieved by for example reacting compounds of formula XV with di-tert.-butoxy carbonate in the presence of a base such as cesium carbonate. The reaction can be carried out in polar solvents such as acetone or butanone and the like at temperatures between 20° C. and 60° C.

Another method to achieve this protection step is to transform first the amino function in a compound with formula XV into an isocyanate by reaction with phosgene or a phosgene equivalent in the presence of a suitable base, which is then treated with tert.-butyl-alcohol to give the desired compounds of formula Vd.

Another suitable method to achieve this protection step is to transform first the amino function in a compound with formula XV into the corresponding di-Boc compound by reaction with excess di-tert.-butoxy carbonate in the presence of 4-dimethylaminopyridine (DMAP), which is then treated with 2eq. TFA in dichloromethane to give the desired compounds of formula Vd.

This reversal of steps, i.e. performing first the nucleophilic aromatic substitution on the key intermediate XIV and second protection of the amino-function as shown in synthetic scheme E can also be applied to those compounds with the formula Vb and Vc (synthetic scheme D).

Yet another method of preparing compounds of the formula Vd is using the O-allyl compound XIX and perfoming a deallylation-alkylation sequence as outlined in scheme E. The deallylation is preferably carried out by transition-metal catalyzed isomerisation, e.g. in the presence of Rhodium(I)-salts like for example Wilkinson's catalyst [(PPh₃)₃RhCl] or Palladium(II)-salts such as [(PPh₃)₂PdCl₂], followed by aqueous acid hydrolysis of the resulting vinyl ether. An example for this procedure can be found in *J. Org. Chem.* 1973, 38, 3224. The alkylation of the phenol XX to the desired compound of the formula Vd can be carried out with electrophilic reagents of the formula R—X, in which R has the meaning of lower alkyl, lower alkenyl, alkyl acetate or benzyl and X represents a leaving group, for example iodide, bromide, methanesulfonate or tolylsulfonate, in a suitable solvent in the presence of a base. The reaction is preferably carried out in polar, aprotic solvents, for example chlorinated solvents such as dichloromethane, chloroform or dichloroethane, or amides, for example dimethylformamide, dimethylacetamide and N-methyl-pyrrolidone, or sulfoxides, for example dimethyl sulfoxide. The base can be selected from the sterically hindered amines such as Hünig's base, alkoxides such as sodium methoxide and tert.-butoxide, hydrides such as sodium hydride, hydroxides such as potassium hydroxide, carbonates such as potassium carbonate or hydrogen carbonates such as potassium hydrogen carbonate. The reaction can be performed at temperatures between −20° C. and 80° C., depending on the individual compounds to be synthesized. For the synthesis of an O-tert.-butyl compound with the formula Vd the phenol XX can be treated with DMF-di-tert.-butylacetal in toluene or benzene at 80° C. as described in *Synthesis* 1983, 135.

According to synthetic scheme F,

Scheme F

Carbon nucleophiles

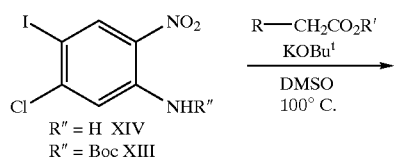

R'' = H XIV
R'' = Boc XIII

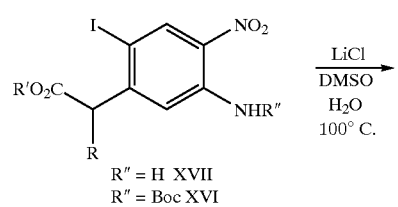

R'' = H XVII
R'' = Boc XVI

Cl moiety

Methyl 3-amino-
4-nitrobenzoate

-continued

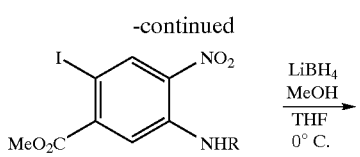

R = H XXI
R = Boc Vg ⎤ GP B

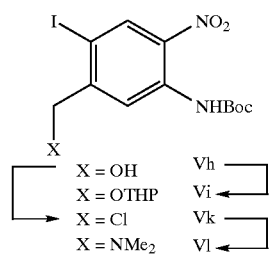

X = OH    Vh
X = OTHP  Vi
X = Cl    Vk
X = NMe₂  Vl compounds of formula Ve and Vf in which $R^2$ is attached via a carbon atom ($R^2$ represents for example lower alkyloxy-carbonyl-methyl; cyano-methyl, etc.) can be prepared from compound XIII or XIV by for example reaction with a malonic acid ester or -half-ester in the presence of a base followed by the removal of one of the alkyl carboxylates via decarboxylation. The exact reaction conditions vary with the identity of the individual compounds and are described in the examples.

The key intermediates XIII and XIV can be prepared as already described in scheme C.

For the one-carbon-moiety bearing compounds of the formula Vh to Vl, the synthesis starts from known methyl 3-amino-4-nitrobenzoate. Standard iodination as described in synthetic scheme C leads to the iodide XXI, which in turn can be protected with the Boc-group. The reduction of the methyl ester can for example be performed by treatment with lithium borohydride, sodium borohydride or diisobutylaluminumhydride in an aprotic solvent like for example THF, ether or toluene. The presence of an alcohol such as methanol, ethanol or isopropanol can be advantegous. The reduction is preferably carried out at temperatures between −20° C. and 0° C. Further functionalization, like for example conversion into a chloride (Vk), of the resulting benzylic alcohol Vh follows standard procedures known to someone skilled in the art. The exact reaction conditions vary with the identity of the individual compounds and are described in the examples.

Scheme G

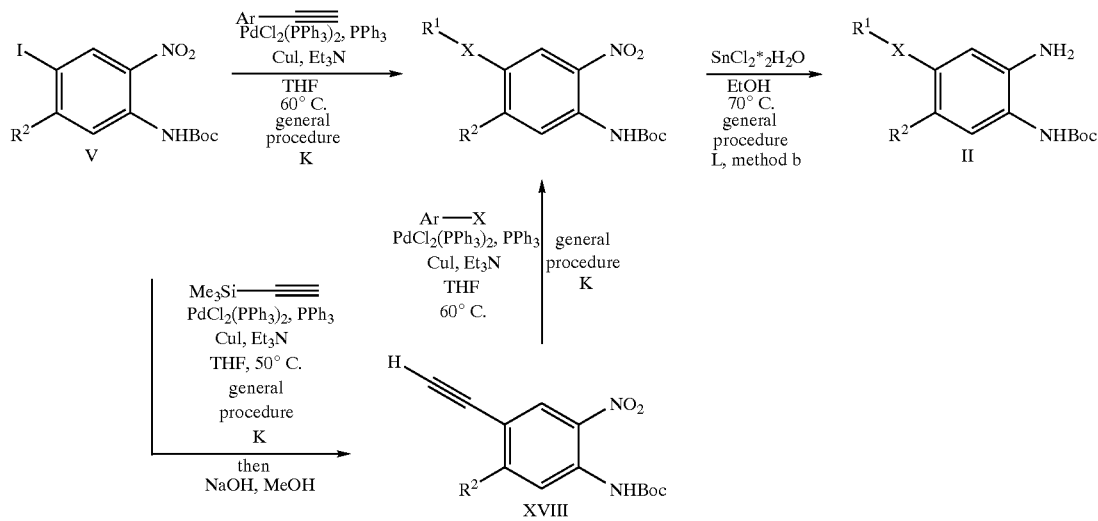

According to scheme G, compounds of formula II in which $R^1$ is as described above for compounds where X is an ethynediyl group can be prepared by different routes from the iodo-compounds V, depending on the nature of $R^1$ and $R^2$ As shown in scheme G, the transformation can for example be carried out a) by directly attaching the $R^1$-alkynediyl-substituent to a compound of formula V via a Sonogashira-type coupling followed by the reduction of the nitro group or b) by two stepwise Sonogashira-type couplings, in which first trimethylsilyl-acetylene is coupled to a compound of formula V to yield, after deprotection with sodium hydroxide in methanol, the intermediate XVIII which then can be transformed via a second Sonogashira-type coupling with the appropriate reactant $R^1$—I, $R^1$—Br or $R^1$—$OSO_2CF_3$ and reduction of the nitro group to the desired compounds of formula II.

The exact conditions for the respective compounds can be found in the experimental part.

Scheme H

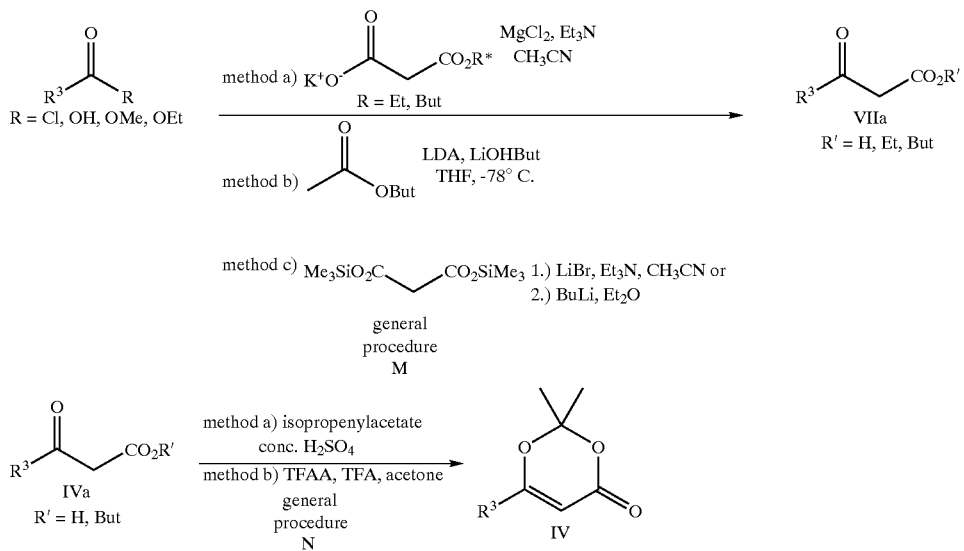

According to Scheme H, the dioxinones and β-keto esters building blocks with the formula IV and IVa can be prepared by methods known to someone skilled in the art from the corresponding carboxylic acid derivatives $R^3$—COR, i.e. free acids, methyl or ethyl esters and acid chlorides. The exact conditions for the corresponding compounds can be found in the experimental part.

Another synthetic route to prepare compounds of formula I in which $R^1$, $R^2$ and X have the meaning as described above and $R^3$ is a carbamide of formula $C(O)NR^4R^5$, in which $R^4$ and $R^5$ is hydrogen, lower alkyl or $R^4$ and $R^5$ together form a morpholino-residue or a N-methyl-piperazine, is outlined in scheme I:

Scheme I

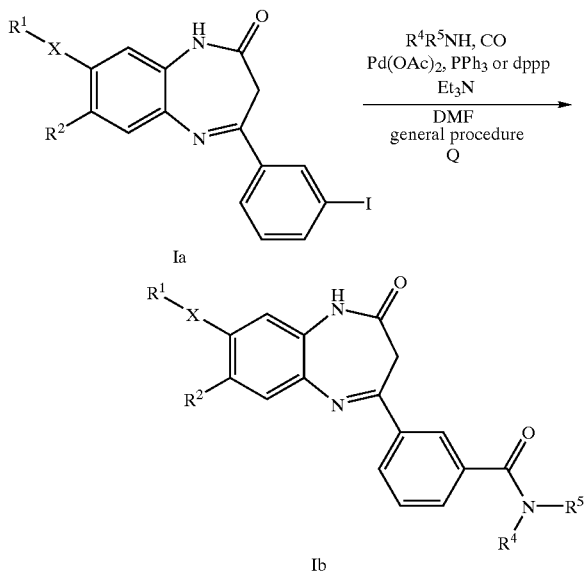

The exact conditions for the respective compounds can be found in the experimental part.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. The compounds of formula I and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The present invention relates also to the use of compounds of formula I and of pharmaceutically acceptable salts thereof for the production of medicaments, especially for the control or prevention of acute and/or chronic neurological disorders of the aforementioned kind.

The compounds of the present invention are group II mGlu receptor antagonists. The compounds show activities, as measured in the assay described below, of 50 $\mu$M or less, typically 3 $\mu$M or less, and ideally of 0.5 $\mu$M or less. In the table below are described some specific pKi values of preferred compounds.

| Compound | $K_i$ mGlu2 ($\mu$M) |
|---|---|
| 3-(8-Chloro-4-oxo-7-phenylethynyl-4,5-dihydro-3H-benzo[b][1,4]diazepin-2-yl)-benzonitrile | 0.028 |
| 3-[8-(4-Methyl-piperazin-1-yl)-4-oxo-7-phenylethynyl-4,5-dihydro-3H-benzo[b][1,4]diazepin-2-yl]-benzonitrile | 0.305 |
| 3-(8-Chloro-4-oxo-7-phenyl-4,5-dihydro-3H-benzo[b][1,4]diazepin-2-yl)-benzonitrile | 0.120 |
| [4-(3-Cyano-phenyl)-2-oxo-8-phenylethynyl-2,3-dihydro-1H-benzo[b][1,4]diazepin-7-ylsulfanyl]-acetic acid methyl ester | 0.051 |
| 2-[4-(3-Cyano-phenyl)-2-oxo-8-phenylethynyl-2,3-dihydro-1H-benzo[b][1,4]diazepin-7-yl]-acetamide | 0.037 |

-continued

| Compound | $K_i$ mGlu2 ($\mu$M) |
|---|---|
| 3-(8-Methoxy-4-oxo-7-phenylethynyl-4,5-dihydro-3H-benzo[b][1,4]diazepin-2-yl)-benzonitrile | 0.046 |
| 3-(8-Cyanomethyl-4-oxo-7-phenylethynyl-4,5-dihydro-3H-benzo[b][1,4]diazepin-2-yl)-benzonitrile | 0.016 |
| 4-(3-Iodo-phenyl)-7-(2-methoxy-ethoxy)-8-phenylethynyl-1,3-dihydro-benzo[b][1,4]diazepin-2-one | 0.021 |
| 4-(3-Imidazol-1-yl-phenyl)-7-(2-methoxy-ethoxy)-8-phenylethynyl-1,3-dihydro-benzo[b][1,4]diazepin-2-one | 0.012 |
| [RS]-3-[4-Oxo-8-(2-oxo-[1,3]dioxolan-4-ylmethoxy)-7-phenylethynyl-4,5-dihydro-3H-benzo[b][1,4]diazepin-2-yl]-benzonitrile | 0.035 |
| 7-Hydroxymethyl-4-(3-imidazol-1-yl-phenyl)-8-phenylethynyl-1,3-dihydro-benzo[b][1,4]diazepin-2-one | 0.018 |
| [4-(3-Imidazol-1-yl-phenyl)-2-oxo-8-phenylethynyl-2,3-dihydro-1H-benzo[b][1,4]diazepin-7-yloxy]-acetonitrile | 0.009 |
| 8-(4-Fluoro-phenylethynyl)-7-hydroxymethyl-4-(3-imidazol-1-yl-phenyl)-1,3-dihydro-benzo[b][1,4]diazepin-2-one | 0.009 |
| 7-(2-Hydroxy-ethoxy)-4-(3-imidazol-1-yl-phenyl)-8-phenylethynyl-1,3-dihydro-benzo[b][1,4]diazepin-2-one | 0.032 |
| 8-(4-Fluoro-phenyl)-7-[4-(2-hydroxy-ethoxy)-piperidin-1-yl]-4-(3-imidazol-1-yl-phenyl)-1,3-dihydro-benzo[b][1,4]diazepin-2-one | 0.100 |
| 8-(4-Fluoro-phenyl)-7-hydroxy-4-(3-imidazol-1-yl-phenyl)-1,3-dihydro-benzo[b][1,4]diazepin-2-one | 0.007 |
| 8-(2-Fluoro-phenyl)-7-methoxy-4-[3-(2-methyl-imidazol-1-yl)-phenyl]-1,3-dihydro-benzo[b][1,4]diazepin-2-one | 0.138 |
| 5-[7-(2-Fluoro-phenyl)-8-methoxy-4-oxo-4,5-dihydro-3H-benzo[b][1,4]diazepin-2-yl]-thiophene-2-carbonitrile | 0.168 |
| 4-[7-(2-Fluoro-phenyl)-8-methoxy-4-oxo-4,5-dihydro-3H-benzo[b][1,4]diazepin-2-yl]-pyridine-2-carbonitrile | 0.033 |
| 8-(2-Fluoro-phenyl)-7-hydroxy-4-(3-[1,2,3]triazol-1-yl-phenyl)-1,3-dihydro-benzo[b][1,4]diazepin-2-one | 0.028 |
| 8-(2-Fluoro-phenyl)-7-hydroxy-4-[3-(2-methyl-imidazol-1-yl)-phenyl]-1,3-dihydro-benzo[b][1,4]diazepin-2-one | 0.108 |
| 8-(2-Fluoro-phenyl)-7-hydroxy-4-[3-(2-methylsulfanyl-imidazol-1-yl)-phenyl]-1,3-dihydro-benzo[b][1,4]diazepin-2-one | 0.021 |
| 8-(2,5-Difluoro-phenyl)-7-methoxy-4-(3-[1,2,3]triazol-1-yl-phenyl)-1,3-dihydro-benzo[b][1,4]diazepin-2-one | 0.012 |
| 8-(2-Fluoro-phenyl)-7-hydroxy-4-[3-(3-methyl-isoxazol-5-yl)-phenyl]-1,3-dihydro-benzo[b][1,4]diazepin-2-one | 0.015 |
| 3-[7-(2,5-Difluoro-phenyl)-8-hydroxy-4-oxo-4,5-dihydro-3H-benzo[b][1,4]diazepin-2-yl]-benzonitrile | 0.006 |
| 8-(4-Fluoro-phenylethynyl)-7-hydroxy-4-(3-imidazol-1-yl-phenyl)-1,3-dihydro-benzo[b][1,4]diazepin-2-one | 0.013 |
| 8-(4-Fluoro-phenylethynyl)-7-hydroxy-4-(3-[1,2,3]triazol-1-yl-phenyl)-1,3-dihydro-benzo[b][1,4]diazepin-2-one | 0.010 |

[$^3$H]-LY354740 Binding on mGlu2 Transfected CHO Cell Membranes

Transfection and Cell Culture cDNA encoding the rat mGlu2 receptor protein in pBluescript II was obtained from Prof. S. Nakanishi (Kyoto, Japan), and subcloned into the eukaryotic expression vector pcDNA I-amp from Invitrogen (NV Leek, The Netherlands). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco BRL (Basel, Switzerland). Selection was made in the presence of G-418 (1000 ug/ml final). Clones were identified by reverse transcription of 5 $\mu$g total RNA, followed by PCR using mGlu2 receptor specific primers 5'-atcactgcttgggtttctggcactg-3' and 5'-agcatcactgtgggtggcataggagc-3' in 60 mM Tris HCl (pH 10), 15 mM $(NH_4)_2SO_4$, 2 mM $MgCl_2$, 25 units/ml Taq Polymerase with 30 cycles annealing at 60° C. for 1 min., extention at 72° C. for 30 s, and 1min. 95° C.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the Pierce method (Socochim, Lausanne, Switzerland) using bovine serum albumin as standard.

[$^3$H]-LY354740 Binding

After thawing, the membranes were resuspended in cold 50 mM Tris-HCl buffer containing 2 mM $MgCl_2$ and 2 mM $CaCl_2$, (pH 7) (binding buffer). The final concentration of the membranes in the assays was 25 $\mu$g protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/C glass fiber filters and washed 5 times with cold binding buffer. Non specific binding was measured in the presence of 10 $\mu$M DCG IV. After transfer of the filters into plastic vials containing 10 ml of Ultima-gold scintillation fluid (Packard, Zürich, Switzerland), the radioactivity was measured by liquid scintillation in a Tri-Carb 2500 TR counter (Packard, Zürich, Switzerland).

Data analysis

The inhibition curves were fitted with a four parameter logistic equation giving IC50 values, and Hill coefficients.

EXAMPLES

The following examples relate to the preparation of the (4-iodo-2-nitro-phenyl)-carbamic acid tert.-butyl esters (Synthetic Scheme C):

General Procedure A

Preparation of 4-iodo-2-nitroanilines by Iodination of 2-nitroanilines [According to Wilson, J. Gerald; Hunt, Frederick C. *Aust. J. Chem.* 1983, 36, 2317–25]

To a stirred solution of the 2-nitroaniline (1.0 mol) in HOAc (500 mL) containing anhydrous NaOAc (93–103 g, 1.125–1.25 mol), iodine monochloride (59–66 mL, 1.125–1.25 mol) in HOAc (300 mL) was added over 60 min. The reaction mixture was heated to the given temperature until thin layer chromatography (tlc) indicated complete conversion of the starting material, stirred for another 30 min at 23° C., then diluted slowly with $H_2O$ (1000 mL) which caused the separation of the crystalline product. Stirring was continued for 1 h and the product was filtered off, washed free of HOAc and dried in vacuum at 60° C.

Example A1

5-Chloro-4-iodo-2-nitro-phenylamine

Prepared from 5-chloro-2-nitroaniline by iodination with iodine monochloride in HOAc/NaOAc according to the general procedure A (80° C.). Obtained as an orange solid.

MS (EI) 298 (M$^+$) and 300 [(M+2)$^+$]; mp 202–203° C. (dec.).

Example A2

4-Iodo-5-methyl-2-nitro-phenylamine

Prepared from 5-methyl-2-nitroaniline by iodination with iodine monochloride in HOAc/NaOAc according to the general procedure A (80° C.). Obtained as a red solid.

MS (EI) 278 (M$^+$); mp 154° C. (dec.).

Example A3

5-Amino-2-iodo-4-nitrobenzoic acid methyl ester

Prepared from 3-amino-4-nitrobenzoic acid methyl ester (22.25 g, {CAS-No. [99512-09-1]; prepared in two steps as follows: 3-hydroxy-4-nitrobenzoic acid (30 g, 164 mmol), NH$_4$Cl (21.91 g, 410 mmol) in 25% aq. NH$_3$ (180 mL) was heated in a steel autoclave at 160° C. for 7 h (internal pressure: 23 bar). Cooled to 23° C. and evaporated to dryness. Taken up in H$_2$O (200 mL), adjusted pH with conc. H$_2$SO$_4$ to pH 1, saturated with NaCl and extracted with EtOAc (6×750 mL), dried combined organic layer over MgSO$_4$. Filtration and removal of the solvent in vacuum left the sufficiently pure 3-amino-4-nitrobenzoic acid (22.26 g, 75%) as an orange solid. This material was suspended in MeOH (500 mL), conc. H$_2$SO$_4$ (3 mL) was added and the mixture was heated to 65° C. for 2.5 days. The solvent was removed in vacuum, the solid residue taken up in EtOAc, washed with sat. NaHCO$_3$-sol. and brine, followed by drying over MgSO$_4$. Removal of the solvent left the sufficiently pure 3-amino-4-nitrobenzoic acid methyl ester (22.25 g, 93%) as an orange solid.} by iodination with iodine monochloride in HOAc/NaOAc according to the general procedure A (35° C.). Obtained as an orange solid (29.38 g, 80%).

MS (EI) 322 (M$^+$); mp 168° C. (dec.).

General Procedure B

Preparation of (2-nitro-phenyl)-carbamic acid tert.-butyl esters from 2-nitroanilines Method a: To a solution of diphosgene (4.1 mL, 34.1 mmol) in EtOAc (40 mL) at 0° C. was added a solution of the 4-iodo-2-nitroaniline (45.5 mmol) in EtOAc (200–500 mL), and the mixture was heated to reflux for 18 h. The solvent was removed in vacuum to leave a brown solid, which was triturated with hot hexane (200 mL). The solid material was filtered off and the filtrate was concentrated under reduced pressure to leave the pure 4-iodo-2-nitrophenylisocyanate as a yellow solid. This material was refluxed in a mixture of excess tert.-BuOH in CH$_2$Cl$_2$ for 2.5 h. Removal of the solvent left an orange solid which was purified by silica gel column chromatography with hexane/EtOAc to give the (4-iodo-2-nitro-phenyl)-carbamic acid tert.-butyl ester as a yellow solid.

Method b: To a mixture of the 4-iodo-2-nitroaniline (142 mmol) and cesium carbonate (55.5 g, 170 mmol) in 2-butanone (740 mL) was dropwise added a solution of Boc$_2$O (37.8 g, 173 mmol) in 2-butanone (170 mL) and the resulting mixture was stirred at 52° C. for 26 h. The solvent was removed in vacuum, the residue was treated with a mixture of H$_2$O (240 mL) and MeOH (240 mL) and extracted with hexane (3×500 mL). The combined hexane layer was washed with brine (200 mL) and all aqueous layers were reextracted with hexane (300 mL). All combined hexane layers were dried over MgSO$_4$, filtered and the solvent was removed in vacuum to give an orange solid, which was purified by silica gel column chromatography with hexane/EtOAc to give the (4-iodo-2-nitrophenyl)-carbamic acid tert.-butyl ester as a yellow solid.

Method c: To a solution of the 4-iodo-2-nitroaniline (550 mmol) and DMAP (1.22 g, 10 mmol) in THF (1000 mL) at 23° C. was dropwise added within 70 min a solution of Boc$_2$O (246 g, 1128 mmol) in THF (500 mL) and stirring was continued at 23° C. for 75 min. The entire mixture was evaporated to dryness and dried at HV to leave a dark brown solid (253.59 g). This material was dissolved in DCM (1100 mL), cooled to 0° C. and TFA (84 mL, 1100 mmol) was added dropwise. The mixture was stirred at 0° C. for 2 h, poured into icecold sat. NaHCO3-sol., extracted with DCM, washed with brine and dried over MgSO4. Removal of the solvent in vacuum left a dark brown solid (199.71 g) which was coated on silica gel and purified by silica gel column chromatography with hexane/EtOAc to give the (4-iodo-2-nitro-phenyl)-carbamic acid tert.-butyl ester as a yellow solid.

Example B1

(5-Chloro-4-iodo-2-nitro-phenyl)-carbamic acid tert.-butyl ester

Prepared the isocyanate from 5-chloro-4-iodo-2-nitrophenylamine (Example A1) (7.0 g, 23.45 mmol) with diphosgene (2.12 mL, 17.6 mmol) in EtOAc (30 mL), followed by treatment with tert.-BuOH (100 mL) in CH$_2$Cl$_2$ (100 mL) according to the general procedure B (method a). Obtained as a yellow solid (7.1 g, 76%).

MS (EI) 398 (M$^+$) and 400 [(M+2)$^+$]; mp 82–84° C.

Example B2

(4-Iodo-5-methyl-2-nitro-phenyl)-carbamic acid tert.-butyl ester

Prepared the isocyanate from 4-iodo-5-methyl-2-nitrophenylamine (Example A2) (13.51 g, 48.6 mmol) with diphosgene (4.4 mL, 36.4 mmol) in EtOAc (50 mL), followed by treatment with tert.-BuOH (150 mL) and CH$_2$Cl$_2$ (150 mL) according to the general procedure B (method a). Obtained as a yellow solid (14.1 g, 77%).

MS (EI) 378 (M$^+$); mp 99–100° C.

Example B3

5-tert.-Butoxycarbonylamino-2-iodo-4-nitro-benzoic acid methyl ester

Prepared the isocyanate from 5-amino-2-iodo-4-nitrobenzoic acid methyl ester (Example A3) (5.5 g, 17 mmol) with diphosgene (1.55 mL, 13 mmol) in EtOAc (135 mL), followed by treatment with tert.-BuOH (20 mL) and CH$_2$Cl$_2$ (70 mL) according to the general procedure B (method a). Obtained as a yellow solid (5.2 g, 72%).

MS (ISP) 440 [(M+NH$_4$)$^+$]; mp 126° C.

Example B4

(5-Allyloxy-4-iodo-2-nitro-phenyl)-carbamic acid tert.-butyl ester

Prepared the isocyanate from 5-allyloxy-4-iodo-2-nitrophenylamine (Example E1) (9.0 g, 28.2 mmol) with diphosgene (2.6 mL, 21.2 mmol) in EtOAc (150 mL), followed by treatment with tert.-BuOH (80 mL) and CH$_2$Cl$_2$ (80 mL)

according to the general procedure B (method a). Obtained as a yellow solid (9.16 g, 77%).

MS (ISP) 421 [(M+H)$^+$] and 438 [(M+NH$_4$)$^+$]; mp 93–95° C.

Example B5

(4-Iodo-5-methoxy-2-nitro-phenyl)-carbamic acid tert.-butyl ester

Prepared the isocyanate from 4-iodo-5-methoxy-2-nitro-phenylamine (Example E2) (2.85 g, 9.69 mmol) with diphosgene (0.88 mL, 7.27 mmol) in EtOAc (52 mL), followed by treatment with tert.-BuOH (25 mL) and CH$_2$Cl$_2$ (25 mL) according to the general procedure B (method a). Obtained as a yellow solid (3.0 g, 79%).

MS (EI) 394 (M$^+$); mp 171° C.

Example B6

[4-Iodo-5-(2-methoxy-ethoxy)-2-nitro-phenyl]-carbamic acid tert.-butyl ester

Prepared the isocyanate from 4-iodo-5-(2-methoxy-ethoxy)-2-nitro-phenylamine (Example E3) (2.73 g, 8.08 mmol) with diphosgene (0.8 mL, 6.06 mmol) in EtOAc (50 mL), followed by treatment with tert.-BuOH (25 mL) and CH$_2$Cl$_2$ (25 mL) according to the general procedure B (method a). Obtained as a yellow solid (3.0 g, 86%).

MS (ISP) 439 [(M+H)$^+$], 456 [(M+NH$_4$)$^+$] and 461 [(M+Na)$^+$]; mp 109–111° C.

Example B7

[4-Iodo-5-(2-{2-[2-(2-methoxy-ethoxy)-ethoxy]-ethoxy}-ethoxy)-2-nitro-phenyl]-carbamic acid tert.-butyl ester Prepared the isocyanate from 4-Iodo-5-(2-{2-[2-(2-methoxy-ethoxy)-ethoxy]-ethoxy}-ethoxy)-2-nitro-phenylamine (Example E4) (8.0 g, 17 mmol) with diphosgene (1.54 mL, 13 mmol) in EtOAc (100 mL), followed by treatment with tert.-BuOH (25 mL) and CH$_2$Cl$_2$ (25 mL) according to the general procedure B (method a). Obtained as a yellow oil (8.6 g, 89%).

MS (ISP) 588 [(M+NH$_4$)$^+$].

Example B8

(RS)-[5-(2,2-Dimethyl-[1,3]dioxolan-4-ylmethoxy)-2-nitro-4-phenylethynyl-phenyl]-carbamic acid tert.-butyl ester Prepared from (RS)-5-(2,2-dimethyl-[1,3]dioxolan-4-ylmethoxy)-2-nitro-4-phenylethynyl-phenylamine (Example K14) (2.678 g, 5.7 mmol), Cs$_2$CO$_3$ (2.23 g, 6.8 mmol) and Boc$_2$O (1.52 g, 7.0 mmol) in 2-butanone (36.5 mL) at 52° C. according to the general procedure B (method b). Obtained as a yellow foam (2.0 g, 75%).

MS (ISP) 469 [(M+H)$^+$] and 486 [(M+NH$_4$)$^+$]; mp 32° C.

Example B9

[Ve (R=CN; R"=Boc)]

(5-Cyanomethyl-4-iodo-2-nitro-phenyl)-carbamic acid tert.-butyl ester

Prepared the isocyanate from (5-amino-2-iodo-4-nitro-phenyl)-acetonitrile (Example Vf (R=CN; R"=H)) (5.15 g, 17 mmol) with diphosgene (2.05 mL, 17 mmol) in EtOAc (150 mL), followed by treatment with tert.-BuOH (25 mL) and CH$_2$Cl$_2$ (25 mL) according to the general procedure B (method a). Obtained as a yellow solid (4.0 g, 58%).

MS (ISN) 402 [(M–H)$^-$]; mp 124–126° C.

Example B10

[5-(2-tert.-Butoxy-ethoxy)-4-iodo-2-nitro-phenyl]-carbamic acid tert.-butyl ester Prepared the di-Boc-compound from 5-(2-tert.-butoxy-ethoxy)-4-iodo-2-nitro-phenylamine (Example E6) (13.9 g, 36.6 mmol) and Boc$_2$O (16.35 g, 75 mmol), followed by treatment with 2 eq. TFA in CH$_2$Cl$_2$ according to the general procedure B (method c). Obtained as a yellow solid (14.96 g, 85%).

MS (ISP) 481 [(M+H)$^+$]; mp 113–116° C.

Example B11

[4-Iodo-5-(4-methoxy-benzyloxy)-2-nitro-phenyl]-carbamic acid tert.-butyl ester

Prepared the di-Boc-compound from 4-iodo-5-(4-methoxy-benzyloxy)-2-nitro-phenylamine (Example E7) (2.88 g, 7.20 mmol) and Boc$_2$O (3.30 g, 15.12 mmol), followed by treatment with 2 eq. TFA in CH$_2$Cl$_2$ according to the general procedure B (method c). Obtained as a waxy yellow solid (1.74 g).

MS (ISN) 499 [(M–H)$^-$].

The following procedures relate to the preparation of those (4-iodo-2-nitro-phenyl)-carbamic acid tert.-butyl esters bearing nitrogen substituents in the 5-position (Scheme D).

General Procedure C

Preparation of 5-N-substituted-(4-iodo-2-nitro-phenyl)-carbamic acid tert.-butyl esters Method a: from (5-chloro-4-iodo-2-nitro-phenyl)-carbamic acid tert.-butyl ester (5-Chloro-4-iodo-2-nitro-phenyl)-carbamic acid tert.-butyl ester (Example B1) was stirred with the desired amine optionally with toluene or DMSO and/or DIPEA at temperature from 23° C. to 100–130° C. until tlc indicated complete disappearance of the chloride. The reaction was cooled to 23° C. poured into ice-water, the precipitate was filtered off, washed with water and dried in vacuum. In cases were the product did not precipitate, the mixture was extracted with EtOAc, washed with water and brine, dried over Na$_2$SO4. Filtration and removal of the solvent in vacuum left a crude product, which was purified by silica gel column chromatography with hexane/EtOAc to give the pure title compound.

Method b: from 5-chloro-4-iodo-2-nitro-phenylamine

A mixture of 5-chloro-4-iodo-2-nitro-phenylamine (Example A1) (1.49 g, 5.0 mmol), the desired amine (6–25 mmol) and an appropriate base, like for example NaHCO$_3$, K$_2$CO$_3$, Et$_3$N or DIPEA (10–15 mmol) was stirred in DMSO, DMF or toluene (20–50 mL) at 60–130° C. until tlc indicated complete disappearance of the chloride. The reaction was cooled to 23° C. poured into ice-water, neutralized with 1N HCl, the precipitate was filtered off, washed with water and dried in vacuum. In cases were the product did not precipitate, the mixture was extracted with EtOAc, washed with water and brine, dried over Na$_2$SO4. Filtration and removal of the solvent in vacuum left a crude product, which was purified by silica gel column chromatography with hexane/EtOAc to give the pure title compound. Protection of the amino-group was achieved by following the general procedure B.

Example C1

[4-Iodo-5-(4-methyl-piperazin-1-yl)-2-nitro-phenyl]-carbamic acid tert.-butyl ester Prepared from (5-chloro-4-iodo-2-nitro-phenyl)-carbamic acid tert.-butyl ester (Example B1) (2.39 g, 6.0 mmol) and 1-methylpiperazine (1.60 mL, 15 mmol) in toluene (4.5 mL) at 110° C. for 18 h according to the general procedure C (method a). Obtained as a yellow solid (2.2 g).

MS (ISP) 463 [(M+H)$^+$]; mp 134–136° C.

Example C2

(4-Iodo-2-nitro-5-thiomorpholin-4-yl-phenyl)-carbamic acid tert.-butyl ester

Prepared from (5-chloro-4-iodo-2-nitro-phenyl)-carbamic acid tert.-butyl ester (Example B1) (2.0 g, 5.0 mmol) and thiomorpholine (2.6 mL) in toluene (3.8 mL) DIPEA (1.7 mL) at 115° C. for 48 h according to the general procedure C (method a). Obtained as a yellow solid (1.1 g).

MS (ISP) 466 [(M+H)$^+$]; mp 132–134° C.

Example C3

(4-Iodo-5-morpholin-4-yl-2-nitro-phenyl)-carbamic acid tert.-butyl ester

Prepared from (5-chloro-4-iodo-2-nitro-phenyl)-carbamic acid tert.-butyl ester (Example B1) (2.0 g, 5.0 mmol) and morpholine (10 mL) at reflux for 3 h according to the general procedure C (method a). Obtained as a yellow solid (0.805 g).

MS (ISP) 450 [(M+H)$^+$]; mp 43–44° C.

Example C4

[5-(1,4-Dioxa-8-aza-spiro [4.5]dec-8-yl)-4-iodo-2-nitro-phenyl]-carbamic acid tert.-butyl ester Prepared from (5-chloro-4-iodo-2-nitro-phenyl)-carbamic acid tert.-butyl ester (Example B1) (3.0 g, 7.53 mmol), 1,4-dioxa-8-aza-spiro(4,5)decane (4.82 mL, 37.63 mmol) and DIPEA (2.58 mL, 15.0 mmol) in toluene (4 mL) at reflux for 6 h according to the general procedure C (method a). Obtained as an orange solid (4.0 g).

MS (ISP) 506 [(M+H)$^+$]; mp 132–134° C.

Example C5

[4-Iodo-5-(4-methoxy-piperidin-1-yl)-2-nitro-phenyl]-carbamic acid tert.-butyl ester Prepared from 5-chloro-4-iodo-2-nitro-phenylamine (Example A1) (6.91 g, 23.15 mmol), 4-methoxypiperidine (4.0 g, 34.73 mmol) and NaHCO$_3$ (5.83 g, 69.45 mmol) in DMSO (230 mL) at 100° C. according to the general procedure C (method b). The obtained brown solid (7.95 g) was converted to the title compound according to the general procedure B (method c). Obtained as a yellow solid (6.55 g).

MS (ISP) 478 [(M+H)$^+$]; mp 133–135° C.

Example C6

{5-[(2-Hydroxy-ethyl)-methyl-amino]-4-iodo-2-nitro-phenyl}-carbamic acid tert.-butyl ester Prepared from (5-chloro-4-iodo-2-nitro-phenyl)-carbamic acid tert.-butyl ester (Example B1) (1.99 g, 5.0 mmol) and 2-methylaminoethanol (2.00 mL, 25.0 mmol) in DMSO (2.5 mL) at 23° C. according to the general procedure C (method a). Obtained as a yellow gum (1.88 g).

MS (ISP) 438 [(M+H)$^+$].

Example C7

[5-(4-Hydroxy-piperidin-1-yl)-4-iodo-2-nitro-phenyl]-carbamic acid tert.-butyl ester Prepared from (5-chloro-4-iodo-2-nitro-phenyl)-carbamic acid tert.-butyl ester (Example B1) (1.99 g, 5 mmol) and 4-hydroxypiperidine (2.53 g, 25 mmol) in DMSO (2.5 mL) at 23° C. according to the general procedure C (method a). Obtained as a yellow solid (1.88 g).

MS (EI) 463 (M$^+$); mp 58–60° C.

Example C8

{5-[4-(2-Hydroxy-ethoxy)-piperidin-1-yl]-4-iodo-2-nitro-phenyl}-carbamic acid tert.-butyl ester Prepared from (5-chloro-4-iodo-2-nitro-phenyl)-carbamic acid tert.-butyl ester (Example B1) (2.2 g, 5.5 mmol), 4-(2-hydroxyethoxy)piperidine {CAS-No. [40256-14-2]} (800 mg, 5.5 mmol) and Et$_3$N (2.3 mL, 16.5 mmol) in DMSO (2.3 mL) at 23° C. according to the general procedure C (method a). Obtained as a yellow solid (1.65 g).

MS (EI) 507 (M$^+$); mp 64–65° C.

Example C9

[5-(cis-3,4-Dihydroxy-pyrrolidin-1-yl)-4-iodo-2-nitro-phenyl]-carbamic acid tert.-butyl ester Prepared in two steps as follows: (5-chloro-4-iodo-2-nitro-phenyl)-carbamic acid tert.-butyl ester (Example B1) (8.73 g, 21.9 mmol) was reacted with 3-pyrroline (2.0 mL, 26.3 mmol, 70% pure, contains 30% pyrrolidine), Et$_3$N (9.12 mL, 65.7 mmol) in DMSO (14 mL) and EtOH (5 mL) at 23° C. according to the general procedure C (method a) to give a 7:3 mixture of [5-(2,5-dihydro-pyrrol-1-yl)-4-iodo-2-nitro-phenyl]-carbamic acid tert.-butyl ester and (4-iodo-2-nitro-5-pyrrolidin-1-yl-phenyl)-carbamic acid tert.-butyl ester Obtained as a yellow solid (8.57 g). Part (4.31 g) of this material was dihydroxylated by reaction with NMO (1.28 g, 11.0 mmol), 2.5% OsO$_4$ in t-BuOH (1 mL, 0.1 mmol) and K$_2$OsO$_4$ (40 mg, 0.1 mmol) in acetone (250 mL) and H$_2$O (100 mL) at 23° C. for 6 days. Obtained the title compound as an amorphous yellow substance (2.50 g).

MS (ISP) 466 [(M+H)$^+$].

Example C10

[5-(2-Hydroxy-ethylamino)-4-iodo-2-nitro-phenyl]-carbamic acid tert.-butyl ester Prepared from (5-chloro-4-iodo-2-nitro-phenyl)-carbamic acid tert.-butyl ester (Example B1) (3.99 g, 10 mmol) and ethanolamine (3.01 mL, 50 mmol) in DMSO (20 mL) at 23° C. according to the general procedure C (method a). Obtained as a yellow solid (4.53 g).

MS (ISP) 424 [(M+H)$^+$]; mp 130–148° C.

Example C11

[5-((R)-3-Hydroxy-pyrrolidin-1-yl)-4-iodo-2-nitro-phenyl]-carbamic acid tert.-butyl ester Prepared from (5-chloro-4-iodo-2-nitro-phenyl)-carbamic acid tert.-butyl ester (Example B1), (R)-3-hydroxypyrrolidine hydrochloride and Et$_3$N in DMSO at 23° C. according to the general procedure C (method a). Obtained as a yellow solid (3.153 g).

MS (ISP) 450 [(M+H)$^+$]; mp 158° C. (dec.).

The following procedures relate to the preparation of those (4-iodo-2-nitro-phenyl)-carbamic acid tert.-butyl esters bearing sulfur substituents in the 5-position (Synthetic Scheme D):

General Procedure D

Preparation of 5-S-substituted-(4-iodo-2-nitro-phenyl)-carbamic acid tert.-butyl esters from (5-chloro-4-iodo-2-nitro-phenyl)-carbamic acid tert.-butyl ester To a solution of the thiol (2.2 mmol) in DMF was added NaOMe-sol. (5.4M in MeOH, 0.41 mL, 2.2 mmol) followed by (5-chloro-4-iodo-2-nitro-phenyl)-carbamic acid tert.-butyl ester (Example B1) (797 mg, 2.0 mmol) and stirring was continued at 23° C. until tlc indicated complete disappearance of the chloride. Poured into ice-cold 5% citric acid, extracted with EtOAc, washed with sat. NaHCO$_3$-sol., brine, dried over MgSO$_4$. Removal of the solvent left an orange oil, which was purified by silica gel column chromatography with hexane/EtOAc to give the pure title compound.

Example D1

[5-(2-Dimethylamino-ethylsulfanyl)-4-iodo-2-nitro-phenyl]-carbamic acid tert.-butyl ester Prepared from (5-chloro-4-iodo-2-nitro-phenyl)-carbamic acid tert.-butyl ester (Example B1) (399 mg, 1.0 mmol), 2-dimethylaminoethanolethiol hydrochloride (312 mg, 2.2 mmol) and NaOMe solution 5.4M in MeOH (0.8 mL, 8.8 mmol) in DMF (2 mL) according to the general procedure D. Obtained as a yellow solid (306 mg).

MS (ISP) 468 [(M+H)$^+$]; mp 144° C.

Example D2

(5-tert.-Butoxycarbonylamino-2-iodo-4-nitro-phenylsulfanyl)-acetic acid methyl ester Prepared from (5-chloro-4-iodo-2-nitro-phenyl)-carbamic acid tert.-butyl ester (Example B1) (797 mg, 2.0 mmol), methyl thioglycolate (0.2 mL, 2.2 mmol) and NaOMe solution 5.4M in MeOH (0.41 mL, 2.2 mmol) in DMF (2 mL) according to the general procedure D. Obtained as a yellow solid (847 mg).

MS (EI) 468 (M$^+$); mp 110–112° C.

The following procedures relate to the preparation of those (4-iodo-2-nitro-phenyl)-carbamic acid tert.-butyl esters bearing oxygen substituents in the 5-position (Scheme E)

General Procedure E:

Preparation of 5-O-substituted-4-iodo-2-nitro-phenylamines from 5-chloro-4-iodo-2-nitro-phenylamine To a suspension of KOH (85%, 3.62–7.96 g, 55–121 mmol) in DMSO (50 mL) was added the alcohol (125–500 mmol) and the mixture was stirred at 23° C. until all KOH had dissolved. 5-Chloro-4-iodo-2-nitro-phenylamine (Example A1) (15.0 g, 50 mmol) was added in small portions and the resulting dark red clear solution was stirred at 23–60° C. until tlc indicated complete disappearance of the chloride. Poured into ice-cold 1N HCl or ice-cold sat. NH$_4$Cl-sol., extracted with EtOAc or CHCl$_3$, washed with 1N HCl or sat. NH$_4$Cl-sol. and brine, dried over MgSO$_4$. Removal of the solvent left a dark red solid, which was purified by silica gel column chromatography to give the pure title compound.

Example E1

5-Allyloxy-4-iodo-2-nitro-phenylamine

Prepared from 5-chloro-4-iodo-2-nitro-phenylamine (Example A1) (15.0 g, 50 mmol), allyl alcohol (50 mL) and KOH (7.96 g, 121 mmol) in DMSO (50 mL) according to the general procedure E. Obtained as an orange solid (9.38 g).

MS (EI) 320 (M$^+$); mp 74° C.

Example E2

4-Iodo-5-methoxy-2-nitro-phenylamine

Prepared from 5-chloro-4-iodo-2-nitro-phenylamine (Example A1) (2.98 g, 10 mmol), methanol (10 mL) and KOH (1.45 g, 22 mmol) in DMSO (10 mL) according to the general procedure E. Obtained as an orange solid (2.9 g).

MS (ISP) 295 [(M+H)$^+$] and 312 [(M+NH$_4$)$^+$]; mp 189° C.

Example E3

4-Iodo-5-(2-methoxy-ethoxy)-2-nitro-phenylamine

Prepared from 5-chloro-4-iodo-2-nitro-phenylamine (Example A1) (2.98 g, 10 mmol), 2-methoxyethanol (7.9 mL, 100 mmol) and KOH (1.45 g, 22 mmol) in DMSO (8 mL) according to the general procedure E. Obtained as an orange solid (2.8 g).

MS (ISN) 337 [(M–H)$^-$]; mp 121–122° C.

Example E4

4-Iodo-5-(2-{2-[2-(2-methoxy-ethoxy)-ethoxy]-ethoxy}-ethoxy)-2-nitro-phenylamine Prepared from 5-chloro-4-iodo-2-nitro-phenylamine (Example A1) (9.48 g, 32 mmol), tetraethyleneglycol monomethyl ether (19 g, 91 mmol) and KOH (2.31 g, 35 mmol) in DMSO (25 mL) at 60° C. according to the general procedure E. Obtained as a red oil (8.4 g).

MS (ISP) 471 [(M+H)$^+$].

Example E5

(RS)-5-(2,2-Dimethyl-[1,3]dioxolan-4-ylmethoxy)-4-iodo-2-nitro-phenylamine

Prepared from 5-chloro-4-iodo-2-nitro-phenylamine (Example A1) (4.48 g, 15 mmol), D,L-α, β-isopropylidene-glycerol (10 mL, 81 mmol) and KOH (1.01 g, 18 mmol) in DMSO (10 mL) at 23° C. according to the general procedure E. Obtained as a yellow solid (4.9 g).

MS (ISN) 393 [(M–H)$^-$]; mp 151° C.

Example E6

5-(2-tert.-Butoxy-ethoxy)-4-iodo-2-nitro-phenylamine

Prepared from 5-chloro-4-iodo-2-nitro-phenylamine (Example A1) (14.9 g, 50 mmol), 2-tert.-butoxyethanol (29.5 g, 250 mmol) and KOH (3.99 g, 60 mmol) in DMSO (25 mL) at 23° C. according to the general procedure E. Obtained as a yellow solid (14.3 g).

MS (ISP) 381 [(M+H)+]; mp 144–146° C.

Example E7

4-Iodo-5-(4-methoxy-benzyloxy)-2-nitro-phenylamine

Prepared from 5-chloro-4-iodo-2-nitro-phenylamine (Example A1) (5.97 g, 20 mmol), 4-methoxybenzyl alcohol (4.98 mL, 40 mmol) and KOH (1.58 g, 24 mmol) in DMSO (30 mL) at 23° C. according to the general procedure E. Obtained as a yellow-brown solid (2.94 g).

MS (ISN) 399 [(M−H)−]; mp 183° C.

The following examples relate to the preparation of (5-tert.-butoxycarbonylamino-2-iodo-4-nitro-phenyl)-acetic acid methyl ester and (5-cyanomethyl-4-iodo-2-nitro-phenyl)-carbamic acid tert.-butyl ester (Synthetic Scheme F):

Example XVI
(R=CO₂Me: R'=Me: R"=Boc)

2-(5-tert.-Butoxycarbonylamino-2-iodo-4-nitro-phenyl)-malonic acid dimethyl ester To a solution of KOBut (0.56 g, 5.02 mmol) in DMSO (3 mL) was added dimethyl malonate (0.58 mL, 5.02 mmol) followed by (5-chloro-4-iodo-2-nitro-phenyl)-carbamic acid tert.-butyl ester (Example B1) (1.00 g, 2.51 mmol) and the resulting dark red clear solution was stirred at 100° C. until tlc indicated complete disappearance of the chloride. Poured into ice-cold 5% citric acid (100 mL), extracted with EtOAc (2×100 mL), washed with brine, dried over MgSO₄. Removal of the solvent left a yellow oil, which was purified by silica gel column chromatography with hexane/EtOAc 4:1 to give the pure title compound as a yellow gum (1.13 g, 91%)

MS (ISP) 512 [(M+NH₄)+] and 517 [(M+Na)+].

Example XVII
(R=CN; R'=Et; R"=H)

(RS)-(5-Amino-2-iodo-4-nitro-phenyl)-cyano-acetic acid ethyl ester

Prepared as described for example XVI from 5-chloro-4-iodo-2-nitro-phenylamine (Example A1) (14.9 g, 50 mmol), ethyl cyanoacetate (14.7 mL, 100 mmol) and KOBut (11.2 g, 100 mmol) in DMSO (60 mL) at 100° C. for 2 h. Obtained as a dark brown gum.

MS (EI) 375 (M+).

Example Ve
(R=CO₂Me; R"=Boc)

(5-tert.-Butoxycarbonylamino-2-iodo-4-nitro-phenyl)-acetic acid methyl ester A mixture of 2-(5-tert.-butoxycarbonylamino-2-iodo-4-nitro-phenyl)-malonic acid dimethyl ester (Example XVI (R=CO₂Me; R'=Me; R"=Boc)) (3.34 g, 6.76 mmol), LiCl (573 mg, 13.52 mmol) and H₂O (0.122 mL, 6.76 mmol) in DMSO (46 mL) was stirred at 100° C. for 7 h. Poured into ice-water, extracted twice with EtOAc, washed with brine, dried over MgSO₄.

Removal of the solvent left a yellow oil, which was purified by silica gel column chromatography with hexane/ EtOAc 9:1 to give the pure title compound as a yellow solid (1.37 g, 47%).

MS (EI) 436 (M+); mp 93° C.

Example Vf
(R=CN; R"=H)

(5-Amino-2-iodo-4-nitro-phenyl)-acetonitrile

Prepared as described for example Ve from (RS)-(5-amino-2-iodo-4-nitro-phenyl)-cyano-acetic acid ethyl ester (Example XVII (R=CN; R'=Et; R"=H)) (20.62 g, 55 mmol) and LiCl (9.33 g, 220 mmol) in DMSO (370 mL) and H₂O (4.4 mL) at 120° C. for 2.5 h. Obtained as a green-brown solid.

MS (EI) 303 (M+); mp 145–183° C.

The following examples relate to the preparation of (5-hydroxymethyl-4-iodo-2-nitro-phenyl)-carbamic acid tert.-butyl ester, the corresponding THP-ether, as well as the (5-dimethylaminomethyl-4-iodo-2-nitro-phenyl)-carbamic acid tert.-butyl ester via the intermediate chloride (Synthetic Scheme F):

Example Vh

(5-Hydroxymethyl-4-iodo-2-nitro-phenyl)-carbamic acid tert.-butyl ester

LiBH₄ (0.32 g, 14.78 mmol) was added to a solution of 5-tert.-butoxycarbonylamino-2-iodo-4-nitro-benzoic acid methyl ester (Example B3) (3.12 g, 7.39 mmol) and MeOH (0.6 mL, 14.78 mmol) in THF (44 mL) at 0° C. The reaction mixture was stirred at 0° C. for 15 min. Poured into 5% citric acid, extracted twice with EtOAc, washed with sat. NaHCO₃-sol. and brine, dried over MgSO₄. Removal of the solvent left a yellow oil, which was purified by silica gel column chromatography with cyclohexane/EtOAc 4:1 to give the pure title compound as a yellow solid (2.64 g, 91%).

MS (ISP) 412 [(M+NH₄)+]; mp>250° C.

Example Vi

(RS)-[4-Iodo-2-nitro-5-(tetrahydro-pyran-2-yloxymethyl)-phenyl]-carbamic acid tert.-butyl ester To a mixture of (5-hydroxymethyl-4-iodo-2-nitro-phenyl)-carbamic acid tert.-butyl ester (Example Vh) (394 mg, 1.0 mmol) and 3,4-dihydro-2H-pyran (0.11 mL, 1.2 mmol) in DCM (5 mL) at 0° C. was added p-TsOH.H₂O (ca. 5 mg) and the reaction was stirred at 0° C. for 1 Diluted with EtOAc, washed with sat. NaHCO₃-sol. and brine, dried over MgSO₄. Removal of the solvent in vacuum left a yellow oil, which was purified by silica gel column chromatography with hexane/EtOAc 9:1 to give the pure title compound as a yellow gum (470 mg, 98%).

MS (ISN) 477 [(M−H)−].

Example VI

(5-Dimethylaminomethyl-4-iodo-2-nitro-phenyl)-carbamic acid tert.-butyl ester To a mixture of (5-hydroxymethyl-4-iodo-2-nitro-phenyl)-carbamic acid tert.-butyl ester (Example Vh), LiCl (3 eq.) and pyridine (2 eq.) in DMF at 0° C. was added methanesulfonyl chloride (1.5 eq.) and the reaction was stirred at 23° C. for 24 h. Me₂NH in EtOH (10 eq.) was added and stirring was continued for 24 h. Diluted with EtOAc, washed with sat. NaHCO₃-sol. and brine, dried over MgSO₄. Removal of the solvent in vacuum left a yellow oil, which was purified by silica gel column chromatography with cyclohexane/EtOAc 3:1 to give the pure title compound as a yellow oil (421 mg).

MS (ISP) 422 [(M+H)$^+$].

The following examples relate to the preparation of (2-amino-4-aryl-phenyl)-carbamic acid tert.-butyl esters, [2-amino-4-(1-alkenyl)-phenyl]-carbamic acid tert.-butyl esters and (2-amino-4-aroyl-phenyl)-carbamic acid tert.-butyl esters in regioisomerically pure fashion (Synthetic Scheme B):

General Procedure F:

Preparation of (4-aryl-2-nitro-phenyl)-carbamic acid tert.-butyl esters by direct Suzuki-coupling of (4-iodo-2-nitro-phenyl)-carbamic acid tert.-butyl esters with arylboronic acids A mixture of the (4-iodo-2-nitro-phenyl)-carbamic acid tert.-butyl ester (3.0 mmol), the arylboronic acid (4.5 mmol) and PdCl$_2$(PPh$_3$)$_2$ (2 mol %) was refluxed in 1,4-dioxane (25 mL) and 2M Na$_2$CO$_3$-sol. (7.5 mL) [or alternatively with 1M NaHCO$_3$-sol. (7.5 mL), LiCl (6.0 mmol) and (Ph$_3$P)$_4$Pd (3 mol %) in DME (30 mL); also possible with Et$_3$N (9.0 mmol), Pd(OAc)$_2$ (3 mol %), PPh$_3$ (6 mol %) in DMF (10 mL) at 100° C.] until tlc indicated complete conversion of the iodide. The mixture was transferred into a separating funnel, H$_2$O (25 mL) was added and the product was extracted with ether or EtOAc (3×30 mL). The combined organic layers were washed with brine (50 mL) and dried over Na$_2$SO$_4$. Removal of the solvent left a brown residue, which was purified by silica gel column chromatography with cyclohexane/ether or cyclohexane/EtOAc to give the title compound.

Example F1

(2-Chloro-5-nitro-biphenyl-4-yl)-carbamic acid tert.-butyl ester

Prepared from (5-chloro-4-iodo-2-nitro-phenyl)-carbamic acid tert.-butyl ester (Example B1) (1.20 g, 3.00 mmol) and phenyl boronic acid (0.62 g, 3.30 mmol) according to the general procedure F. Obtained as a yellow oil (843 mg).

MS (EI) 348 (M$^+$) and 350 [(M+2)$^+$].

Example F2

(2-Methyl-5-nitro-biphenyl-4-yl)-carbamic acid tert.-butyl ester

Prepared from (4-iodo-5-methyl-2-nitro-phenyl)-carbamic acid tert.-butyl ester (Example B2) (1.135 g, 3 mmol) and phenylboronic acid (630 mg, 3.3 mmol) according to the general procedure F. Obtained as a yellow oil (971 mg).

MS (EI) 328 (M$^+$).

Example F3

(RS)-{4'-Fluoro-5-nitro-2-[4-(tetrahydro-pyran-2-yloxy)-piperidin-1-yl]-biphenyl-4-yl}-carbamic acid tert.-butyl ester Prepared from (RS)-{4-iodo-2-nitro-5-[4-(tetrahydro-pyran-2-yloxy)-piperidin-1-yl]-phenyl}-carbamic acid tert.-butyl ester [RO-69-4319/000, prepared from [5-(4-hydroxy-piperidin-1-yl)-4-iodo-2-nitro-phenyl]-carbamic acid tert.-butyl ester (Example C7) by treatment with 3,4-dihydro-2H-pyran and cat. TsOH.H$_2$O in DCM at 0° C.](1.09 g, 2.0 mmol) and 4-fluorophenylboronic acid according to the general procedure F. Obtained as an orange solid (894 mg).

MS (ISP) 516 [(M+H)$^+$]; mp 144–146° C.

Example F4

(RS)-(4'-Fluoro-5-nitro-2{4-[2-(tetrahydro-pyran-2-yloxy)-ethoxy]-piperidin-1-yl }-biphenyl-4-yl)-carbamic acid tert.-butyl ester Prepared from (RS)-(4-iodo-2-nitro-5-{4-[2-(tetrahydro-pyran-2-yloxy)-ethoxy]-piperidin-1yl}-phenyl)-carbamic acid tert.-butyl ester [RO-69-4355/000, prepared from {5-[4-(2-hydroxy-ethoxy)-piperidin-1-yl]-4-iodo-2-nitro-phenyl}-carbamic acid tert.-butyl ester (Example C8) by treatment with 3,4-dihydro-2H-pyran and cat. TsOH.H$_2$O in DCM at 0° C.] (950 mg, 1.87 mmol) and 4-fluorophenylboronic acid (314 mg, 2.25 mmol) according to the general procedure F. Obtained as a viscous orange oil (930 mg).

MS (ISP) 560 [(M+H)$^+$]; mp 144–146° C.

Example F5

(RS)-[4'-Fluoro-5-nitro-2-(tetrahydro-pyran-2-yloxymethyl)-biphenyl-4-yl -carbamic acid tert.-butyl ester Prepared from (RS)-[4-iodo-2-nitro-5-(tetrahydro-pyran-2-yloxymethyl)-phenyl ]-carbamic acid tert.-butyl ester (Example Vi) and 4-fluorophenylboronic acid according to the general procedure F. Obtained as an orange oil (1.24 g).

Example F6

(2-Cyanomethoxy-4'-fluoro-5-nitro-biphenyl-4-yl)-carbamic acid tert.-butyl ester Prepared from (5-cyanomethoxy-4-iodo-2-nitro-phenyl)-carbamic acid tert.-butyl ester (Example S2) (838 mg, 2.0 mmol) and 4-fluorophenylboronic acid (392 mg, 2.8 mmol) according to the general procedure F. Obtained as a yellow solid (333 mg).

MS (ISP) 405 [(M+NH$_4$)$^+$]; mp 148° C.

Example F7

(2-Dimethylaminomethyl-4'-fluoro-5-nitro-biphenyl-4-yl)-carbamic acid tert.-butyl ester Prepared from (5-dimethylaminomethyl-4-iodo-2-nitro-phenyl)-carbamic acid tert.-butyl ester (Example VI) and 4-fluorophenylboronic acid according to the general procedure F. Obtained as a yellow solid (1.01 g).

Example F8

[2-(2,2-Dimethyl-tetrahydro-[1,3]dioxolo [4,5-c] pyrrol-5-yl)-4'-fluoro-5-nitro-biphenyl-4-yl]-carbamic acid tert.-butyl ester Prepared from [5-(cis-2,2-dimethyl-tetrahydro-[1,3] dioxolo [4,5-c]pyrrol-5-yl)-4-iodo-2-nitro-phenyl]-carbamic acid tert-butyl ester [RO-69–4741/000, prepared from [5-(cis-3,4-dihydroxy-pyrrolidin-1-yl)-4-iodo-2-nitro-phenyl]-carbamic acid tert.-butyl ester (Example C9) by treatment with 2,2-dimethoxypropane and cat. TsOH.H$_2$O in DMF at 23° C.](845 mg, 1.67 mmol) and 4-fluorophenylboronic acid (327 mg, 2.34 mmol) according to the general procedure F. Obtained as a yellow solid (643 mg).

MS (ISP) 474 [(M+H)$^+$]; mp 119° C.

Example F9

(4'-Fluoro-2-methoxy-5-nitro-biphenyl-4-yl)-carbamic acid tert.-butyl ester

Prepared from (4-iodo-5-methoxy-2-nitro-phenyl)-carbamic acid tert.-butyl ester (Example B5) (3.68 g, 9.34 mmol) and 4-fluorophenylboronic acid (3.61 g, 25.8 mmol) according to the general procedure F. Obtained as a yellow solid (2.69 g).

MS (ISN) 361 [(M–H)$^{31}$ ]; mp 250° C.

Example F10

[2-(1,4-Dioxa-8-aza-spiro[4.5]dec-8-yl)-4'-fluoro-5-nitro-biphenyl-4-yl]-carbamic acid tert.-butyl ester Prepared from [5-(1,4-dioxa-8-aza-spiro[4.5]dec-8-yl)-4-iodo-2-nitro-phenyl]-carbamic acid tert.-butyl ester (Example C4) (4.0 g, 7.02 mmol) and 4-fluorophenylboronic acid (1.33 g, 9.5 mmol) according to the general procedure F. Obtained as a yellow solid (2.43 g).

mp 213° C. (dec.).

Example F11

(4'-Fluoro-2-methyl-5-nitro-biphenyl-4-yl)-carbamic acid tert.-butyl ester

Prepared from (4-iodo-5-methyl-2-nitro-phenyl)-carbamic acid tert.-butyl ester (Example B2) (756 mg, 2.0 mmol) and 4-fluorophenylboronic acid (420 mg, 3.0 mmol) according to the general procedure F. Obtained as an amorphous yellow substance (611 mg).

MS (ISN) 345 [(M–H)$^-$].

Example F12

(4-tert.-Butoxycarbonylamino-4'-fluoro-5-nitro-biphenyl-2-yloxy)-acetic acid tert.-butyl ester Prepared from (5-tert.-butoxycarbonylamino-2-iodo-4-nitro-phenoxy)-acetic acid tert.-butyl ester (Example S1) (2.14 g, 4.33 mmol) and 4-fluorophenylboronic acid (728 mg, 5.2 mmol) according to the general procedure F. Obtained as an orange solid (1.80 g).

MS (ISN) 461 [(M–H)$^-$]; mp 92–93° C.

Example F13

(2-Chloro-4'-fluoro-5-nitro-biphenyl-4-yl)-carbamic acid tert.-butyl ester

Prepared from (5-chloro-4-iodo-2-nitro-phenyl)-carbamic acid tert.-butyl ester (Example B1) and 4-fluorophenylboronic acid according to the general procedure F. Obtained as a yellow solid (625 mg).

MS (EI) 366 (M$^+$).

Example F14

[4'-Fluoro-2-(2-methoxy-ethoxy)-5-nitro-biphenyl-4-yl]-carbamic acid tert.-butyl ester Prepared from [4-iodo-5-(2-methoxy-ethoxy)-2-nitro-phenyl-carbamic acid tert.-butyl ester (Example B6) and 4-fluorophenylboronic acid according to the general procedure F. Obtained as a yellow solid (1.833 g).

MS (EI) 406 (Me).

Example F15

[2-(2-tert.-Butoxy-ethoxy)-4'-fluoro-5-nitro-biphenyl-4-yl -carbamic acid tert.-butyl ester Prepared from [5-(2-tert.-butoxy-ethoxy)-4-iodo-2-nitro-phenyl]-carbamic acid tert.-butyl ester (Example B10) and 4-fluorophenylboronic acid according to the general procedure F. Obtained as a yellow solid (735 mg).

MS (ISP) 449 [(M+H)$^+$].

Example F16

[4'-Fluoro-5-nitro-2-(2-oxo-oxazolidin-3-yl)-biphenyl-4-yl]-carbamic acid tert.-butyl ester Prepared from [4-iodo-2-nitro-5-(2-oxo-oxazolidin-3-yl)-phenyl]-carbamic acid tert-butyl ester [RO-69-6758/000, prepared from [5-(2-hydroxy-ethylamino)-4-iodo-2-nitro-phenyl]-carbamic acid tert.-butyl ester (Example C10) by treatment with 1,1'-carbonyldiimidazole in dioxane and then in pyridine with cat. DMAP each at 100° C.](503 mg, 1.12 mmol) and 4-fluorophenylboronic acid (235 mg, 1.68 mmol) according to the general procedure F. Obtained as a yellow solid (310 mg).

MS (ISN) 416 [(M–H)$^-$]; mp 201° C.

Example F17

(4'-Fluoro-2-methoxy-2'-methyl-5-nitro-biphenyl-4-yl)-carbamic acid tert.-butyl ester Prepared from (4-iodo-5-methoxy-2-nitro-phenyl)-carbamic acid tert.-butyl ester (Example B5) and 4-fluoro-2-methyl-phenylboronic acid according to the general procedure F. Obtained as a yellow solid (699 mg).

MS (EI) 376 (M$^+$).

Example F18

(2-tert.-Butoxy-4'-fluoro-5-nitro-biphenyl-4-yl)-carbamic acid tert.-butyl ester Prepared from (5-tert.-butoxy-4-iodo-2-nitro-phenyl)-carbamic acid tert.-butyl ester (Example S4) (1.4 g, 3.21 mmol) and 4-fluorophenylboronic acid (0.67 g, 4.42 mmol) according to the general procedure F. Obtained as an amorphous yellow substance (1.2 g).

MS (EI) 404 (M$^+$).

Example F19

(2-tert.-Butoxy-2'-fluoro-5-nitro-biphenyl-4-yl)-carbamic acid tert.-butyl ester Prepared from (5-tert.-butoxy-4-iodo-2-nitro-phenyl)-carbamic acid tert.-butyl ester (Example S4) (1.4 g, 3.21 mmol) and 2-fluorophenylboronic acid (0.67 g, 4.83 mmol) according to the general procedure F. Obtained as an amorphous yellow substance (960 mg).

MS (EI) 404 (M$^+$).

Example F20

(RS)-{4'-Fluoro-5-nitro-2-[(R)-3-(tetrahydro-pyran-2-yloxy)-pyrrolidin-]-yl]-biphenyl-4yl}-carbamic acid tert.-butyl ester Prepared from (RS)-{4-iodo-2-nitro-5-[(R)-3-(tetrahydro-pyran-2-yloxy)-pyrrolidin-1-yl]-phenyl}-carbamic acid tert-butyl ester [RO-69-6376/000, prepared from 15-((R)-3-hydroxy-pyrrolidin-1-yl)-4-iodo-2-nitro-phenyl]-carbamic acid tert.-butyl ester (Example C11) by treatment with 3,4-dihydro-2H-pyran and cat. TsOH.H$_2$O in DCM at 0° C.] and 4-fluorophenylboronic acid according to the general procedure F. Obtained as a yellow solid (1.053 g).

MS (ISP) 502 [(M+H)⁺].

Example F21

(2'-Fluoro-2-methoxy-5-nitro-biphenyl-4-yl)-carbamic acid tert.-butyl ester

Prepared from (4-iodo-5-methoxy-2-nitro-phenyl)-carbamic acid tert.-butyl ester (Example B5) (1.00 g, 2.54 mmol) and 2-fluorophenylboronic acid (0.60 g, 4.32 mmol) according to the general procedure F. Obtained as an amorphous yellow substance (687 mg).

MS (EI) 362 (M⁺).

Example F22

[2-(1,4-Dioxa-8-aza-spiro[4.5]dec-8-yl)-2'-fluoro-5-nitro-biphenyl-4-yl]-carbamic acid tert.-butyl ester Prepared from [5-(1,4-dioxa-8-aza-spiro[4.5]dec-8-yl)-4-iodo-2-nitro-phenyl]-carbamic acid tert.-butyl ester (Example C4) (1.89 g, 3.47 mmol) and 2-fluorophenylboronic acid (0.63 g, 4.49 mmol) according to the general procedure F. Obtained as a yellow solid (1.46 g).

MS (ISP) 474 [(M+H)⁺]; mp 164° C.

Example F23

(2',5'-Difluoro-2-methoxy-5-nitro-biphenyl-4-yl)-carbamic acid tert.-butyl ester Prepared from (4-iodo-5-methoxy-2-nitro-phenyl)-carbamic acid tert.-butyl ester (Example B5) (3.94 g, 10 mmol) and 2,5-difluorophenylboronic acid (2.21 g, 14 mmol) according to the general procedure F. Obtained as an amorphous yellow substance (1.05 g).

MS (ISN) 379 [(M−H)⁻].

Example F24

[2'-Fluoro-2-(2-methoxy-ethoxy)-5-nitro-biphenyl-4-yl]-carbamic acid tert.-butyl ester Prepared from [4-iodo-5-(2-methoxy-ethoxy)-2-nitro-phenyl]-carbamic acid tert.-butyl ester (Example B6) and 2-fluorophenylboronic acid according to the general procedure F. Obtained as a yellow solid (3.63 g).

MS (ISN) 405 [(M−H)⁻].

Example F25

(RS)-[2'-Fluoro-5-nitro-2-(tetrahydro-pyran-2-yloxymethyl)-biphenyl-4-yl]-carbamic acid tert.-butyl ester Prepared from (RS)-[4-iodo-2-nitro-5-(tetrahydro-pyran-2-yloxymethyl)-phenyl]-carbamic acid tert.-butyl ester (Example Vi) and 2-fluorophenylboronic acid according to the general procedure F. Obtained as a yellow liquid (2.606 g).

MS (ISN) 445 [(M−H)⁻].

Example F26

[2'-Fluoro-2-(4-methoxy-benzyloxy)-5-nitro-biphenyl-4-yl]-carbamic acid tert.-butyl ester Prepared from [4-iodo-5-(4-methoxy-benzyloxy)-2-nitro-phenyl]-carbamic acid tert.-butyl ester (Example B11) (1.69 g, 3.38 mmol) and 2-fluorophenylboronic acid (0.61 g, 4.39 mmol) according to the general procedure F. Obtained as a yellow foam (940 mg).

MS (ISP) 469 [(M+H)⁺].

Example F27

(2-tert.-Butoxy-2',5'-difluoro-5-nitro-biphenyl-4-yl)-carbamic acid tert.-butyl ester Prepared from (5-tert.-butoxy-4-iodo-2-nitro-phenyl)-carbamic acid tert.-butyl ester (Example S4) (3.00 g, 6.88 mmol) and 2,5-difluorophenylboronic acid (2.23 g, 14.1 mmol) according to the general procedure F. Obtained as an amorphous yellow substance (2.30 g).

MS (ISN) 421 [(M−H)⁻].

General Procedure G

Preparation of (4-aryl-2-nitro-phenyl)-carbamic acid tert.-butyl esters by Suzuki-coupling of (4-iodo-2-nitro-phenyl)-carbamic acid tert.-butyl esters with bis(pinacolato)diboron and subsequent reaction with aryl halides A mixture of the (4-iodo-2-nitro-phenyl)-carbamic acid tert.-butyl ester (2.0 mmol), bis(pinacolato)diboron (2.2 mmol), KOAc (6.0 mmol) and PdCl₂(PPh₃)₂ (3 mol %) in 1,4-dioxane (25 mL) was stirred at 100° C. until tlc indicated complete conversion of the iodide [cf. Tetr. Lett. 1997, 38, 3841–3844]. After addition of the aryl halide (4.0 mmol), PdCl₂(PPh₃)₂ (3 mol %) and 2M Na₂CO₃-sol. (7.5 mL) the mixture was stirred at 100° C. until tlc indicated complete conversion of the intermediate boronic ester. The mixture was transferred into a separating funnel, H₂O (30 mL) was added and the product was extracted with ether or EtOAc (3×50 mL). The combined organic layers were washed with brine (100 mL) and dried over Na₂SO₄. Removal of the solvent left a brown residue, which was purified by silica gel column chromatography with cyclohexane/ether or cyclohexane/EtOAc to give the title compound.

General Procedure H

Preparation of (4-aroyl-2-nitro-phenyl)-carbamic acid tert.-butyl esters by carbonylative Suzuki-coupling of (4-iodo-2-nitro-phenyl)-carbamic acid tert.-butyl esters with aryl boronic acids A mixture of the (4-iodo-2-nitro-phenyl)-carbamic acid tert.-butyl ester (1.0 mmol), aryl boronic acid (1.1 mmol), K₂CO₃ (3.0 mmol) and PdCl₂(PPh₃)₂ (3 mol %) in anisole (6 mL was stirred at 80° C. under a CO-atmosphere until thin layer chromatography indicated complete conversion of the iodide [cf. Tetr. Lett. 1993, 34, 7595–7598]. The mixture was transferred into a separating funnel, H₂O (30 mL) was added and the product was extracted with EtOAc (2×100 mL). The combined organic layers were washed with brine (50 mL) and dried over Na₂SO₄. Removal of the solvent left a yellow residue, which was purified by silica gel column chromatography with or hexane/EtOAc to give the title compound.

General Procedure I

Preparation of (4-aryl-2-nitro-phenyl)-carbamic acid tert.-butyl esters or (4-{alkenyl-, cycloalkenyl- or heterocycloalkenyl}-2-nitro-phenyl)-carbamic acid tert.-butyl esters by Stille-coupling of (2-nitro-4-tributylstannanyl-phenyl)-carbamic acid tert.-butyl ester with aryl halides or vinyl triflates or Stille-coupling of (4-iodo-2-nitrophenyl)-carbamic acid tert.-butyl ester with trialkylarylstannanes A mixture of (2-nitro-4-tributylstannanyl-phenyl)-carbamic acid tert.-butyl ester (525 mg, 1.0 mmol; prepared from the corresponding (4-iodo-2-nitro-phenyl)-carbamic acid tert.-butyl ester (Examples B) (10 mmol) by reaction with hexabutyldistannane (7.5 mL, 15 mmol) and Pd(PPh$_3$)$_4$ (116 mg, 0.1 mmol) in toluene (20 mL) at 60° C. for 5 days according to *Bull. Chem. Soc. Jpn.* 1983, 56, 3855–3856), aryl halide or vinyl triflate (0.95–6.0 mmol), anhydrous LiCl (126 mg, 3.0 mmol) and Pd(PPh$_3$)$_4$ (5 mol %) in DME (3 mL) was stirred at 100° C. under argon atmosphere until tlc indicated complete consumption of the stannane. The reaction was cooled to 23° C., stirred with sat. aqueous KF-sol. (5 mL) for 45 min, filtered through celite, washed with ether and the filtrate was dried over MgSO$_4$. Removal of the solvent in vacuum left a brown oil, which was purified by silica gel column chromatography with hexane/EtOAc to give the title compound.

The following examples relate to the preparation of (2-amino-4-arylethynyl-phenyl)-carbamic acid tert.-butyl esters in regioisomerically pure fashion (Synthetic Scheme G):

General Procedure K

Preparation of (4-alkynyl-2-nitro-phenyl)-carbamic acid tert.-butyl esters by Sonogashira-coupling of (4-iodo-2-nitro-phenyl)-carbamic acid tert.-butyl esters with acetylenic compounds also Sonogashira-coupling of (4-ethynyl-2-nitro-phenyl)-carbamic acid tert.-butyl esters with aryl halides and Sonogashira-coupling of 8-iodo-4-aryl-1,3-dihydro-benzo[b][1,4]diazepin-2-ones with acetylenic compounds A mixture of the halide (3.0–4.5 mmol), acetylenic compound (3.0–4.5 mmol), Et$_3$N (13.5 mmol), PdCl$_2$(PPh$_3$)$_2$ (5 mol %) and PPh$_3$ (2.5 mol %) in THF (12 mL) [with very insoluble material DMF (up to 12 mL) could be added] was stirred for 20 min at 23° C. while being purged with Argon. CuI (1.2 mol %) was added and stirring was continued at 60° C. under Argon atmosphere until tlc indicated complete conversion of the minor component [cf. *J. Org. Chem.* 1998, 63, 8551]. The mixture was transferred into a separating funnel, 5% citric acid (50 mL) was added and the product was extracted with EtOAc (2×100 mL). The combined organic layers were washed with sat. NaHCO$_3$-sol. (50 mL) and brine (50 mL), followed by drying over MgSO$_4$. Removal of the solvent left a yellow residue, which was purified by silica gel column chromatography with hexane/EtOAc and/or triturated with hexane or aqueous EtOH to give the title compound.

Example K1

(5-Chloro-2-nitro-4-phenylethynyl-phenyl)-carbamic acid tert.-butyl ester

Prepared from (5-chloro-4-iodo-2-nitro-phenyl)-carbamic acid tert.-butyl ester (Example B1) (1.2 g, 3.0 mmol) and phenylacetylene (0.5 mL, 4.5 mmol) according to the general procedure K. Obtained as a yellow solid (944 mg).

MS (ISN) 371 [(M−H)$^-$] and 373 [(M−H+2)$^-$]; mp 166–167° C.

Example K2

(5-Methyl-2-nitro-4-phenylethynyl-phenyl)-carbamic acid tert.-butyl ester

Prepared from (4-iodo-5-methyl-2-nitro-phenyl)-carbamic acid tert.-butyl ester (Example B2) (1.13 g, 3.0 mmol) and phenylacetylene (0.5 mL, 4.5 mmol) according to the general procedure K. Obtained as a green-yellow solid (794 mg).

MS (EI) 352 (M$^+$); mp 161–164° C.

Example K3

[5-(4-Methyl-piperazin-1-yl)-2-nitro-4-phenylethynyl-phenyl]-carbamic acid tert.-butyl ester Prepared from [4-iodo-5-(4-methyl-piperazin-1-yl)-2-nitro-phenyl]-carbamic acid tert.-butyl ester (Example C1) (1.34 g, 3.0 mmol) and phenylacetylene (0.5 mL, 4.5 mmol) according to the general procedure K. Obtained as a green-yellow solid (1.1 g).

MS (ISP) 437 [(M+H)$^+$]; mp 170° C.

Example K4

(5-Morpholin-4-yl-2-nitro-4-phenylethynyl-phenyl)-carbamic acid tert.-butyl ester Prepared from (4-iodo-5-morpholin-4-yl-2-nitro-phenyl)-carbamic acid tert.-butyl ester (Example C3) (890 mg, 2.0 mmol) and phenylacetylene (0.33 mL, 3.0 mmol) according to the general procedure K. Obtained as an orange solid (580 mg).

MS (ISP) 424 [(M+H)$^+$]; mp 190–191° C.

Example K5

(2-Nitro-4-phenylethynyl-5-thiomorpholin-4-yl-phenyl)-carbamic acid tert.-butyl ester Prepared from (4-iodo-2-nitro-5-thiomorpholin-4-yl-phenyl)-carbamic acid tert.-butyl ester (Example C2) (1.0 g, 2.15 mmol) and phenylacetylene (0.36 mL, 3.22 mmol) according to the general procedure K. Obtained as an orange solid (620 mg).

MS (ISP) 440 [(M+H)$^+$] and 462 [(M+Na)$^+$]; mp 201° C. (dec.).

Example K6

[5-(1,1-Dioxo-thiomorpholin-4-yl)-2-nitro-4-phenylethynyl-phenyl]-carbamic acid tert.-butyl ester Prepared in two steps as followed:

To a solution of (4-iodo-2-nitro-5-thiomorpholin-4-yl-phenyl)-carbamic acid tert.-butyl ester (Example C2) (465 mg, 1 mmol) in acetone (25 mL) and H2O (1 mL) 0.3M ammoniummolybdate sol. (0.3 mL) and 33% H$_2$O$_2$ (2.3 mL) were added at 0° C. and mixture was stirred for 1 h at 23° C. Obtained the [5-(1,1-dioxo-thiomorpholin-4-yl)-4-iodo-2-nitro-phenyl]-carbamic acid tert.-butyl ester (497 mg, 1.0 mmol) as an amorphous yellow material, which was reacted with phenylacetylene (0.17 mL, 1.5 mmol) according to the general procedure K. Obtained as a yellow solid (245 mg).

MS (ISP) 472 [(M+H)$^+$]; mp 217–221° C.

Example K7

[5-(1,4-Dioxa-8-aza-spiro[4.5]dec-8-yl)-2-nitro-4-phenylethynyl-phenyl]-carbamic acid tert.-butyl ester Prepared from [5-(1,4-dioxa-8-aza-spiro[4.5]dec-8-yl)-4-iodo-2-nitro-phenyl]-carbamic acid tert.-butyl ester (Example C4) (3.80 g, 7.53 mmol) and phenylacetylene (1.24 mL, 11.3 mmol) according to the general procedure K. Obtained as a orange solid (1.8 g).

MS (ISN) 478 [(M−H)⁻]; mp 179–180° C.

Example K8

[5-(2-Dimethylamino-ethylsulfanyl)-2-nitro-4-phenylethynyl-phenyl]-carbamic acid tert.-butyl ester Prepared from (5-(2-dimethylamino-ethylsulfanyl)-4-iodo-2-nitro-phenyl]-carbamic acid tert.-butyl ester (Example D1) (721 mg, 1.54 mmol) and phenylacetylene (0.25 mL, 2.31 mmol) according to the general procedure K. Obtained as an amorphous yellow material (595 mg).

MS (ISP) 442 [(M+H)⁺]; mp 179–180° C.

Example K9

(5-tert.-Butoxycarbonylamino-4-nitro-2-phenylethynyl-phenylsulfanyl)-acetic acid methyl ester Prepared from (5-tert.-butoxycarbonylamino-2-iodo-4-nitro-phenylsulfanyl)-acetic acid methyl ester (Example D2) (780 mg, 1.67 mmol) and phenylacetylene (0.27 mL, 2.5 mmol) according to the general procedure K. Obtained as an orange solid (700 mg).

MS (ISP) 460 [(M+NH₄)⁺]; mp 125–127° C.

Example K10

[5-(2-Methoxy-ethoxy)-2-nitro-4-phenylethynyl-phenyl]-carbamic acid tert.-butyl ester Prepared from [4-iodo-5-(2-methoxy-ethoxy)-2-nitro-phenyl-carbamic acid tert.-butyl ester (Example B6) (876 mg, 2 mmol) and phenylacetylene (0.33 mL, 3 mmol) according to the general procedure K. Obtained as a yellow solid (569 mg).

MS (ISP) 413 [(M+H)⁺] and 430 [(M+NH₄)⁺]; mp 118–119° C.

Example K11

(5-Methoxy-2-nitro-4-phenylethynyl-phenyl)-carbamic acid tert.-butyl ester

Prepared from (4-iodo-5-methoxy-2-nitro-phenyl)-carbamic acid tert.-butyl ester (Example B5) (1.18 g, 3.00 mmol) and phenylacetylene (0.58 mL, 4.5 mmol) according to the general procedure K. Obtained as a yellow solid (1.1 g).

MS (EI) 368 (M⁺); mp 129° C.

Example K12

[5-(2-{2-[2-(2-Methoxy-ethoxy)-ethoxy]-ethoxy}-ethoxy)-2-nitro-4-phenylethynyl-phenyl]-carbamic acid tert.-butyl ester Prepared from (4-iodo-5-(2-{2-[2-(2-methoxy-ethoxy)-ethoxy]-ethoxy}-ethoxy)-2-nitro-phenyl]-carbamic acid tert.-butyl ester (Example B7) (5.7 g, 10.0 mmol) and phenylacetylene (1.65 mL, 15 mmol) according to the general procedure K. Obtained as a yellow oil (5.2 g).

MS (ISN) 543 [(M−H)⁻].

Example K13

(5-tert.-Butoxycarbonylamino-4-nitro-2-phenylethynyl-phenoxy)-acetic acid tert.-butyl ester Prepared from (5-tert.-butoxycarbonylamino-2-iodo-4-nitro-phenoxy)-acetic acid tert.-butyl ester (Example S1) (1.46 g, 2.99 mmol) and phenylacetylene (0.49 mL, 4.49 mmol) according to the general procedure K. Obtained as a yellow solid (1.4 g).

MS (ISP) 486 [(M+NH₄)⁺]; mp 130° C.

Example K14

(RS)-5-(2,2-Dimethyl-[1,3]dioxolan-4-ylmethoxy)-2-nitro-4-phenylethynyl-phenylamine Prepared from (RS)-5-(2,2-dimethyl-[1,3]dioxolan-4-ylmethoxy)-4-iodo-2-nitro-phenylamine (Example E5) (4.5 g, 11.4 mmol) and phenylacetylene (1.88 mL, 17.1 mmol) according to the general procedure K. Obtained as an orange solid (5.4 g).

MS (ISN) 367 [(M−H)⁻]; mp 147–149 C.

Example K15

(5-tert.-Butoxycarbonylamino-4-nitro-2-phenylethynyl-benzoic acid methyl ester

Prepared from 5-tert.-butoxycarbonylamino-2-iodo-4-nitro-benzoic acid methyl ester (Example B3) (1.22 g, 2.89 mmol) and phenylacetylene (0.48 mL, 4.34 mmol) according to the general procedure K. Obtained as a yellow solid (793 mg).

MS (ISP) 397 [(M+H)⁺] and 414 [(M+NH₄)⁺]; mp 173° C.

Example K16

(5-tert.-Butoxycarbonylamino-4-nitro-2-phenylethynyl-phenyl)-acetic acid methyl ester Prepared from (5-tert.-butoxycarbonylamino-2-iodo-4-nitro-phenyl)-acetic acid methyl ester (Example Ve (R=CO₂Me; R″=Boc)) (1.32 g, 3.03 mmol) and phenylacetylene (0.5 mL, 4.55 mmol) according to the general procedure K. Obtained as a yellow solid (1.1 g).

MS (ISP) 411 [(M+H)⁺], 428 [(M+NH₄)⁺] and 433 [(M+Na)⁺]; mp 134° C.

Example K17

(5-Cyanomethyl-2-nitro-4-phenylethynyl-phenyl)-carbamic acid tert.-butyl ester

Prepared from (5-cyanomethyl-4-iodo-2-nitro-phenyl)-carbamic acid tert.-butyl ester (Example B9 [Ve (R=CN; R″=Boc)]) (3.97 g, 9.85 mmol) and phenylacetylene (3.24 mL, 29.56 mmol) according to the general procedure K. Obtained as an olive solid (1.6 g).

MS (ISP) 395 [(M+NH₄)⁺]; mp 166° C.

Example K18

(RS)-[5-(2,3-Dihydroxy-propoxy)-2-nitro-4-phenylethynyl-phenyl]-carbamic acid tert.-butyl ester Prepared from (RS)-[5-(2,3-dihydroxy-propoxy)-4-iodo-2-nitro-phenyl]-carbamic acid tert.-butyl ester (RO-68-5451/000 (3.23 g, 7.11 mmol); prepared from (5-allyloxy-4-iodo-2-nitro-phenyl)-carbamic acid tert.-butyl ester (Example B4) (4.20 g, 10.0 mmol) by reaction with NMO (1.28 g, 11.0 mmol), OSO₄ 2.5% in t-BuOH (1 mL, 0.1 mmol) and K₂OsO₄ (40 mg, 0.1 mmol) in acetone (250 mL) and H₂O (100 mL) at 23° C. for 6 days) and phenylacetylene (1.17 mL, 10.67 mmol) according to the general procedure K. Obtained as a yellow solid (2.74 g).

MS (ISP) 429 [(M+H)+]; mp 157° C. (dec.).

Example K19

(5-Hydroxymethyl-2-nitro-4-phenylethynyl-phenyl)-carbamic acid tert.-butyl ester Prepared from (5-hydroxymethyl-4-iodo-2-nitro-phenyl)-carbamic acid tert.-butyl ester (Example Vh) (2.61 g, 6.62 mmol) and phenylacetylene (1.10 mL, 9.93 mmol) according to the general procedure K. Obtained as a yellow solid (1.76 g).

MS (ISP) 386 [(M+NH$_4$)+]; mp 177° C. (dec.).

Example K20

[5-(4-Methoxy-piperidin-1-yl)-2-nitro-4-phenylethynyl-phenyl]-carbamic acid tert.-butyl ester Prepared from [4-iodo-5-(4-methoxy-piperidin-1-yl)-2-nitro-phenyl)-carbamic acid tert.-butyl ester (Example C5) (1.0 g, 2.1 mmol) and phenylacetylene (0.35 mL, 3.15 mmol) according to the general procedure K. Obtained as a yellow solid (799 mg).

mp 147–150° C.

Example K21

(5-Cyanomethoxy-2-nitro-4-phenylethynyl-phenyl)-carbamic acid tert.-butyl ester

Prepared from (5-cyanomethoxy-4-iodo-2-nitro-phenyl)-carbamic acid tert.-butyl ester (Example S2) (605 mg, 1.44 mmol) and phenylacetylene (0.24 mL, 2.16 mmol) according to the general procedure K. Obtained as a yellow solid (508 mg).

MS (EI) 393 (M+); mp 170° C.

Example K22

[4-(4-Fluoro-phenylethynyl)-5-hydroxymethyl-2-nitro-phenyl]-carbamic acid tert.-butyl ester Prepared from (5-hydroxymethyl-4-iodo-2-nitro-phenyl)-carbamic acid tert.-butyl ester (Example Vh) (2.00 g, 5.07 mmol) and 4-fluorophenylacetylene (0.91 g, 7.61 mmol) according to the general procedure K. Obtained as a yellow solid (1.55 g).

MS (ISN) 385 [(M–H)−]; mp 198° C.

Example K23

(RS)-(4-(4-Fluoro-phenylethynyl)-5-{methyl-[2-(tetrahydro-pyran-2-yloxy)-ethyl]-amino}-2-nitro-phenyl)-carbamic acid tert.-butyl ester Prepared from (RS)-(4-iodo-5-{methyl-[2-(tetrahydro-pyran-2-yloxy)-ethyl]-amino}-2-nitro-phenyl)-carbamic acid tert-butyl ester [RO-69-3820/000, prepared from {5-[(2-hydroxy-ethyl)-methyl-amino]-4-iodo-2-nitro-phenyl}-carbamic acid tert.-butyl ester (Example C6) by treatment with 3,4-dihydro-2H-pyran and cat. TsOH.H$_2$O in DCM at 0° C.](2.09 g, 4.01 mmol) and 4-fluorophenylacetylene (0.72 g, 6.02 mmol) according to the general procedure K. Obtained as a yellow-brown solid (1.84 g).

MS (ISP) 514 [(M+H)+]; mp 134° C.

Example K24

(RS)-{2-Nitro-4-phenylethynyl-5-[2-(tetrahydro-pyran-2-yloxy)-ethoxy]-phenyl}-carbamic acid tert.-butyl ester Prepared from (RS)-{4-iodo-2-nitro-5-[2-(tetrahydro-pyran-2-yloxy)-ethoxy]-phenyl}-carbamic acid tert.-butyl ester (Example S3) (743 mg, 1.46 mmol) and phenylacetylene (0.24 mL, 2.19 mmol) according to the general procedure K. Obtained as a yellow-brown viscous oil (429 mg).

MS (EI) 393 (M+).

Example K25

Prepared from [5-(2-tert.-butoxy-ethoxy)-4-iodo-2-nitro-phenyl]-carbamic acid tert.-butyl ester (Example B10) (1.44 g, 3.0 mmol) and 4-fluorophenylacetylene (541 mg, 4.5 mmol) according to the general procedure K. Obtained as a yellow solid (777 mg).

MS (EI) 472 (M+); mp 96–98° C.

Example K26

[5-tert.-Butoxy-4-(4-fluoro-phenylethynyl)-2-nitro-phenyl]-carbamic acid tert.-butyl ester Prepared from (5-tert.-butoxy-4-iodo-2-nitro-phenyl)-carbamic acid tert.-butyl ester (Example S4) (1.40 g, 3.21 mmol) and 4-fluorophenylacetylene (0.66 g, 5.46 mmol) according to the general procedure K. Obtained as a brown solid (520 mg).

MS (EI) 428 (M+); mp 201° C.

General Procedure L

Preparation of the (2-amino-phenyl)-carbamic acid tert.-butyl esters by reduction of (2-nitro-phenyl)-carbamic acid tert.-butyl esters Also preparation of 4-aryl-1,3-dihydro-benzo[b][1,4]diazepin-2-ones by reduction and concomitant cyclization of 3-aryl-N-(2-nitro-phenyl)-3-oxo-propionamides Method a: Catalytic hydrogenation A mixture of the nitro compound (1.0 mmol) in MeOH or EtOH and THF (1:1 ca. 20 mL) and 10% Palladium on carbon (20 mg) or Raney-Ni (20 mg) was stirred vigorously at 23° C. under hydrogen atmosphere until tlc indicated complete conversion. The catalyst was filtered off, washed thoroughly with MeOH or EtOH and THF (1:1), the solvent was removed in vacuum to give the title compound, which was generally pure enough for further transformations.

Method b: Reduction with SnCl$_2$.2H$_2$O

A mixture of the nitro compound (1.0 mmol) and SnCl$_2$.2H$_2$O (5.0 mmol) was either stirred in EtOH (30 mL) at 70–80° C. or alternatively in pyridine (3 mL) and DMF (12 mL) at 23° C. under Argon atmosphere until tlc indicated complete conversion [cf. *Tetr. Lett.* 1984, 25, 839]. The reaction mixture was brought to pH 8 by addition of sat. NaHCO$_3$-sol. and extracted with EtOAc (2×100 mL). The combined organic layer were washed with brine and dried over Na$_2$SO$_4$. Removal of the solvent left a yellow solid, which—if necessary—can be purified by silica gel column chromatography.

Method c: Reduction with Zn and NH$_4$Cl

To a mixture of the nitro compound (1.0 mmol) in EtOH/THF/sat. NH$_4$Cl-sol. (1:1:1, 30 mL) was added Zinc dust (3.0 mmol) and the mixture was stirred at 70° C. under Argon atmosphere until tlc indicated complete conversion. Aqueous workup as described in method b.

Method d: Reduction with Fe and HOAc

To a mixture of the nitro compound (1.0 mmol) in THF/$H_2O$ (4:1, 10–50 mL) was added Fe powder (6.0 mmol) and the mixture was stirred at 70° C. under Argon atmosphere until tlc indicated complete conversion. Aqueous workup as described in method b.

Example L1

(2-Amino-4-iodo-5-thiomorpholin-4-yl-phenyl)-carbamic acid tert.-butyl ester

Prepared from (4-iodo-2-nitro-5-thiomorpholin-4-yl-phenyl)-carbamic acid tert.-butyl ester (Example C2) (1.05 g, 2.25 mmol) by reduction with $SnCl_2.2H_2O$ (2.54 g, 11.3 mmol) according to the general procedure L (method b). Obtained as a light yellow solid (993 mg).

MS (ISP) 436 [(M+H)$^+$]; mp 125–127° C.

Example L2

(2-Amino-4-iodo-5-morpholin-4-yl-phenyl)-carbamic acid tert.-butyl ester

Prepared from (4-iodo-5-morpholin-4-yl-2-nitro-phenyl)-carbamic acid tert.-butyl ester (Example C3) (753 g, 1.65 mmol) by reduction with $SnCl_2.2H_2O$ (1.9 g, 8.27mmol) according to the general procedure L (method b). Obtained as a yellow solid (696 mg).

MS (ISP) 420 [(M+H)$^+$]; mp 139–143° C.

Example L3

(2-Amino-5-chloro-4-phenylethynyl-phenyl)-carbamic acid tert.-butyl ester

Prepared from (5-chloro-2-nitro-4-phenylethynyl-phenyl)-carbamic acid tert.-butyl ester (Example K1) (742 mg, 2.0 mmol) by reduction with $SnCl_2.2 H_2O$ (2.245 g, 10 mmol) according to the general procedure L (method b). Obtained as an orange solid (483 mg).

MS (ISP) 343 [(M+H)$^+$] and 345 [(M+2+H)$^+$].

Example L4

(2-Amino-5-methyl-4-phenylethynyl-phenyl)-carbamic acid tert.-butyl ester

Prepared from (5-methyl-2-nitro-4-phenylethynyl-phenyl)-carbamic acid tert.-butyl ester (Example K2) (741 mg, 2.1 mmol) by reduction with $SnCl_2.2H_2O$ (2.37 g, 10.3 mmol) according to the general procedure L (method b). Obtained as a light-brown solid (419 mg).

MS (ISP) 323 [(M+H)$^+$]; mp 172–173° C.

Example L5

[2-Amino-5-(4-methyl-piperazin-1-yl)-4-phenylethynyl-phenyl]-carbamic acid tert.-butyl ester Prepared from [5-(4-methyl-piperazin-1-yl)-2-nitro-4-phenylethynyl-phenyl]-carbamic acid tert.-butyl ester (Example K3) (1.08 g, 2.48 mmol) by reduction with $SnCl_2.2H_2O$ (2.8 g, 12.4 mmol) according to the general procedure L (method b). Obtained as an orange solid (1.0 g).

MS (ISP) 407 [(M+H)$^+$]; mp 81–85° C.

Example L6

(5-Amino-2-chloro-biphenyl-4-yl)-carbamic acid tert.-butyl ester

Prepared from (2-chloro-5-nitro-biphenyl-4-yl)-carbamic acid tert.-butyl ester (Example F1) (783 mg, 2.24 mmol) by reduction with $SnCl_2.2H_2O$ (2.53 g, 11.2 mmol) according to the general procedure L (method b). Obtained as a yellow solid (684 mg).

MS (EI) 318 (M$^+$) and 320 [(M+2)$^+$]; mp 109–111° C.

Example L7

(5-Amino-2-methyl-biphenyl-4-yl)-carbamic acid tert.-butyl ester

Prepared from (2-methyl-5-nitro-biphenyl-4-yl)-carbamic acid tert.-butyl ester (Example F2) (921 mg, 2.8 mmol) by catalytic hydrogenation with Pd/C according to the general procedure L (method a). Obtained as a white solid (796 mg).

MS (EI) 298 (M$^+$); mp 122° C.

Example L8

[2-Amino-5-(2-dimethylamino-ethylsulfanyl)-4-phenylethynyl-phenyl]-carbamic acid tert.-butyl ester Prepared from [5-(2-dimethylamino-ethylsulfanyl)-2-nitro-4-phenylethynyl -phenyl]-carbamic acid tert.-butyl ester (Example K8) (551 mg, 1.25 mmol) by reduction with $SnCl_2.2H_2O$ (1.41 g, 6.25 mmol) according to the general procedure L (method b). Obtained as an orange foam (510 mg).

MS (ISP) 412 [(M+H)$^+$]; mp 115–117° C.

Example L9

(4-Amino-5-tert.-butoxycarbonylamino-2-phenylethynyl-phenylsulfanyl)-acetic acid methyl ester Prepared from (5-tert.-butoxycarbonylamino-4-nitro-2-phenylethynyl-phenylsulfanyl)-acetic acid methyl ester (Example K9) (634 mg, 1.43 mmol) by reduction with $SnCl_2.2H_2O$ (1.62 g, 7.16 mmol) according to the general procedure L (method b). Obtained as an orange gum (590 mg).

MS (ISP) 413 [(M+H)$^+$], 435 [(M+Na)$^+$] and 451 [(M+K)$^+$].

Example L10

(4-Amino-5-tert.-butoxycarbonylamino-2-phenylethynyl-phenyl)-acetic acid methyl ester Prepared from (5-tert.-butoxycarbonylamino-4-nitro-2-phenylethynyl-phenyl)-acetic acid methyl ester (Example K16) (1.09 g, 2.66 mmol) by reduction with $SnCl_2.2H_2O$ (3.00 g, 13.28 mmol) according to the general procedure L (method b). Obtained as a light yellow solid (900 mg).

MS (ISP) 381 [(M+H)$^+$] and 403 [(M+Na)$^+$]; mp 130° C.

Example L11

[2-Amino-5-(2-methoxy-ethoxy)-4-phenylethynyl-phenyl]-carbamic acid tert.-butyl ester Prepared from [5-(2-methoxy-ethoxy)-2-nitro-4-phenylethynyl-phenyl]-carbamic acid tert.-butyl ester (Example K10) (1.417 g, 3.44 mmol) by reduction with $SnCl_2.2H_2O$ (3.88 g, 17.2 mmol) according to the general procedure L (method b). Obtained as an off-white solid (1.04 g).

MS (EI) 382 (M$^+$); mp 105–107° C.

Example L12

(2-Amino-5-morpholin-4-yl-4-phenylethynyl-phenyl)-carbamic acid tert.-butyl ester Prepared from (5-morpholin-4-yl-2-nitro-4-phenylethynyl-phenyl)-carbamic acid tert.-butyl ester (Example K4) (563 mg, 1.329 mmol) by reduction with $SnCl_2.2H_2O$ (1.5 g, 6.65 mmol) according to the general procedure L (method b). Obtained as a red-brown solid (488 mg).

MS (ISP) 394 [(M+H)$^+$]; mp 174–176° C.

Example L13

(2-Amino-5-methoxy-4-phenylethynyl-phenyl)-carbamic acid tert.-butyl ester

Prepared from (5-methoxy-2-nitro-4-phenylethynyl-phenyl)-carbamic acid tert.-butyl ester Example K11 (1.00 g, 2.71 mmol) by reduction with $SnCl_2.2H_2O$ (3.06 g, 13.57 mmol) according to the general procedure L (method b). Obtained as a yellow solid (870 mg).

MS (EI) 338 (M$^+$); mp 158° C.

Example L14

4-Amino-5-tert.-butoxycarbonylamino-2-phenylethynyl-benzoic acid methyl ester

Prepared from (5-tert.-butoxycarbonylamino-4-nitro-2-phenylethynyl-benzoic acid methyl ester (Example K15) (754 mg, 1.90 mmol) by reduction with $SnCl_2.2H_2O$ (2.15 g, 9.51 mmol) according to the general procedure L (method b). Obtained as a pink solid (431 mg).

MS (EI) 366 (M$^+$); mp 164° C.

Example L15

[2-Amino-5-(2-{2-[2-(2-methoxy-ethoxy)-ethoxy]-ethoxy}-ethoxy)-4-phenylethynyl-phenyl]-carbamic acid tert.-butyl ester Prepared from [5-(2-{2-[2-(2-methoxy-ethoxy)-ethoxy]-ethoxy}-ethoxy)-2-nitro-4-phenylethynyl-phenyl]-carbamic acid tert.-butyl ester (Example K12) (3.0 g, 5.51 mmol) by reduction with $SnCl_2.2H_2O$ (6.2 g, 27.54 mmol) according to the general procedure L (method b). Obtained as a brown oil (2.9 g).

MS (ISP) 515 [(M+H)$^+$].

Example L16

(4-Amino-5-tert.-butoxycarbonylamino-2-phenylethynyl-phenoxy)-acetic acid tert.-butyl ester Prepared from (5-tert.-butoxycarbonylamino-4-nitro-2-phenylethynyl-phenoxy)-acetic acid tert.-butyl ester (Example K13) (1.32 g, 2.82 mmol) by reduction with $SnCl_2.2H_2O$ (3.18 g, 14.10 mmol) according to the general procedure L (method b). Obtained as an amorphous orange material (1.2 g).

MS (ISP) 439 [(M+H)$^+$] and 461 [(M+Na)$^+$].

Example L17

(2-Amino-5-cyanomethyl-4-phenylethynyl-phenyl)-carbamic acid tert.-butyl ester

Prepared from (5-cyanomethyl-2-nitro-4-phenylethynyl-phenyl)-carbamic acid tert.-butyl ester (Example K17) (377 mg, 1.0 mmol) by reduction with $SnCl_2.2H_2O$ (1.13 g, 5.0 mmol) according to the general procedure L (method b). Obtained as an orange solid (338 mg).

MS (ISP) 348 [(M+H)$^+$] and 370 [(M+Na)$^+$]; mp 143° C.

Example L18

[2-Amino-5-(1,4-dioxa-8-aza-spiro [4.5]dec-8-yl)-4-phenylethynyl-phenyl]-carbamic acid tert.-butyl ester and [2-Amino-5-(4,4-diethoxy-piperidin-1-yl)-4-phenylethynyl-phenyl]-carbamic acid tert.-butyl ester Prepared from [5-(1,4-dioxa-8-aza-spiro[4.5]dec-8-yl)-2-nitro-4-phenylethynyl-phenyl]-carbamic acid tert.-butyl ester (Example K7) (1.73 g, 3.6 mmol) by reduction with $SnCl_2.2H_2O$ (4.0 g, 18.0 mmol) in EtOH according to the general procedure L (method b). Obtained as a brown solid (418 mg) and as dark brown solid (379 mg), respectively.

MS (ISP) 450 [(M+H)$^+$]; mp 79–82° C.; MS (ISP) 480 [(M+H)$^+$].

Example L19

[2-Amino-5-(1,1-dioxo-6-thiomorpholin-4-yl)-4-phenylethynyl-phenyl]-carbamic acid tert.-butyl ester Prepared from [5-(1,1-dioxo-thiomorpholin-4-yl)-2-nitro-4-phenylethynyl-phenyl]-carbamic acid tert.-butyl ester (Example K6) (235 mg, 0.5 mmol) by reduction with $SnCl_2.2H_2O$ (564 mg, 2.5 mmol) according to the general procedure L (method b). Obtained as a brown solid (418 mg, impure material, used directly in Example 6 without purification and characterization).

Example L20

[2-Amino-5-(2,2-dimethyl-[1,3]dioxolan-4-ylmethoxy)-4-phenylethynyl-phenyl]-carbamic acid tert.-butyl ester Prepared from (RS)-[5-(2,2-dimethyl-[1,3]dioxolan-4-ylmethoxy)-2-nitro-4-phenylethynyl-phenyl]-carbamic acid tert.-butyl ester (Example B8) (1.90 g, 4.06 mmol) by reduction with $SnCl_2.2H_2O$ (4.6 g, 20.32 mmol) according to the general procedure L (method b). The crude product was reprotected by stirring with 2,2-dimethoxypropane (5 mL) and p-TsOH.$H_2O$ (1.1 eq) in DMF (5 mL) at 23° C. for 4 h. Obtained as a brown solid (1.1 g).

MS (ISP) 439 [(M+H)$^+$], 461 [(M+Na)$^+$] and 477 [(M+K)$^+$].

Example L21

4-Amino-5-tert.-butoxycarbonylamino-2-iodo-benzoic acid methyl ester

Prepared from 5-tert.-butoxycarbonylamino-2-iodo-4-nitro-benzoic acid methyl ester (Example B3) (3.00 g, 7.11 mmol) by reduction with $SnCl_2.2H_2O$ (8.02 g, 35.55 mmol) according to the general procedure L (method b). Obtained as a light red foam (1.9 g).

MS (ISP) 393 [(M+H)$^+$]; mp 60–78° C.

Example L22

[RS]-[2-Amino-5-(2-oxo-[1,3]dioxolan-4-ylmethoxy)-4-phenylethynyl-phenyl]-carbamic acid tert.-butyl ester Prepared from [RS]-[2-Nitro-5-(2-oxo-[1,3]dioxolan-4-ylmethoxy)-4-phenylethynyl-phenyl]-carbamic acid tert.- butyl ester [RO-68-8108/000 (411 mg, 0.9 mmol), prepared from (RS)-[5-(2,3-dihydroxy-propoxy)-2-nitro-4-phenylethynyl-phenyl]-carbamic acid tert.-butyl ester (Example K18) by treatment with 1,1'-carbonyldiimidazole in THF at 0 to 23° C.] by reduction with $SnCl_2.2H_2O$ (1.02 g, 4.5 mmol) according to the general procedure L (method b). Obtained as an apricot solid (370 mg).

MS (ISP) 425 [(M+H)$^+$]; mp 140° C.

Example L23

(2-Amino-5-ethoxymethyl-4-phenylethynyl-phenyl)-carbamic acid tert.-butyl ester

Prepared from carbonic acid 5-tert.-butoxycarbonylamino-4-nitro-2-phenylethynyl-benzyl ester methyl ester [RO-68-8481/000, prepared from (5-hydroxymethyl-2-nitro-4-phenylethynyl-phenyl)-carbamic acid tert.-butyl ester (Example K19) by treatment with methyl chloroformate and $Et_3N$ in THF at 0° C.] by reduction with $SnC_2.2H_2O$ according to the general procedure L (method b). Obtained as an amorphous brown substance (139 mg).

MS (ISP) 367 [(M+H)$^+$].

Example L24

2,2-Dimethyl-propionic acid 4-amino-5-tert.-butoxycarbonylamino-2-phenylethynyl-benzyl ester Prepared from 2,2-dimethyl-propionic acid 5-tert-butoxycarbonylamino-4-nitro-2-phenylethynyl-benzyl ester [RO-68-9779/000, prepared from (5-hydroxymethyl-2-nitro-4-phenylethynyl-phenyl)-carbamic acid tert.-butyl ester (Example K19) by treatment with pivaloyl chloride and cat. DMAP in pyridine at 0 to 23° C.] by reduction with $SnCl_2.2H_2O$ according to the general procedure L (method b). Obtained as an amorphous yellow substance (182 mg).

MS (ISN) 421 [(M–H)$^-$].

Example L25

(RS)-2-Amino-4-phenylethynyl-5-(tetrahydro-pyran-2-yloxymethyl)-phenyl]-carbamic acid tert.-butyl ester Prepared from (RS)-[2-nitro-4-phenylethynyl-5-(tetrahydro-pyran-2-yloxymethyl)-phenyl]-carbamic acid tert.-butyl ester [RO-69-2829/000, prepared from (5-hydroxymethyl-2-nitro-4-phenylethynyl-phenyl)-carbamic acid tert.-butyl ester (Example K19) by treatment with 3,4-dihydro-2 H-pyran and cat. $TsOH.H_2O$ in DCM at 0° C.] by reduction with $SnCl_2.2H_2O$ according to the general procedure L (method b). Obtained as a yellow solid (1.78 g).

MS (ISN) 421 [(M–H)$^-$]; mp 158° C.

Example L26

[2-Amino-5-(4-methoxy-piperidin-1-yl)-4-phenylethynyl-phenyl]-carbamic acid tert.-butyl ester Prepared from [5-(4-methoxy-piperidin-1-yl)-2-nitro-4-phenylethynyl-phenyl-carbamic acid tert.-butyl ester (Example K20) (727 mg, 1.61 mmol) by reduction with $SnC_2.2H_2O$ according to the general procedure L (method b). Obtained as a yellow solid (489 mg).

MS (ISP) 422 [(M+H)$^+$]; mp 173–176° C.

Example L27

(2-Amino-5-cyanomethoxy-4-phenylethynyl-phenyl)-carbamic acid tert.-butyl ester

Prepared from (5-cyanomethoxy-2-nitro-4-phenylethynyl-phenyl)-carbamic acid tert.-butyl ester (Example K21) (395 mg, 0.91 mmol) by reduction with $SnCl_2.2H_2O$ according to the general procedure L (method b). Obtained as an amorphous yellow substance (219 mg).

MS (ISP) 364 [(M+H)$^+$].

Example L28

(RS)-[2-Amino-4-(4-fluoro-phenylethynyl)-5-(tetrahydro-pyran-2-yloxymethyl)-phenyl]-carbamic acid tert.-butyl ester Prepared from (RS)-[4-(4-fluoro-phenylethynyl)-2-nitro-5-(tetrahydro-pyran-2-yloxymethyl)-phenyl]-carbamic acid tert.-butyl ester [RO-69-3877/000, prepared from [4-(4-fluoro-phenylethynyl)-5-hydroxymethyl-2-nitro-phenyl]-carbamic acid tert.-butyl ester (Example K22) by treatment with 3,4-dihydro-2 H-pyran and cat. $TsOH.H_2O$ in DCM at 0° C.] by reduction with $SnC_2.2H_2O$ according to the general procedure L (method b). Obtained as an amorphous light brown substance (990 mg).

MS (ISP) 441 [(M+H)$^+$].

Example L29

(RS)-(2-Amino-4-(4-fluoro-phenylethynyl)-5-{methyl-[2-(tetrahydro-pyran-2-yloxy)-ethyl]-amino}-phenyl)-carbamic acid tert.-butyl ester Prepared from (RS)-(4-(4-fluoro-phenylethynyl)-5-{methyl-[2-(tetrahydro-pyran-2-yloxy)-ethyl]-amino}-2-nitro-phenyl)-carbamic acid tert.-butyl ester (Example K23) (1.79 g, 3.49 mmol) by reduction with $SnCl_2.2H_2O$ according to the general procedure L (method b). Obtained as an amorphous light brown substance (1.20 g).

MS (ISP) 484 [(M+H)$^+$].

Example L30

(RS)-{2-Amino-4-phenylethynyl-5-[2-(tetrahydro-pyran-2-yloxy)-ethoxy]-phenyl }-carbamic acid tert.-butyl ester Prepared from (RS)-{2-nitro-4-phenylethynyl-5-[2-(tetrahydro-pyran-2-yloxy)-ethoxy]-phenyl}-carbamic acid tert.-butyl ester (Example K24) (420 mg, 0.87 mmol) by reduction with $SnCl_2.2H_2O$ according to the general procedure L (method b). Obtained as a light brown solid (346 mg).

MS (ISP) 453 [(M+H)$^+$].

Example L31

(RS)-{5-Amino-4'-fluoro-2-[4-(tetrahydro-pyran-2-yloxy)-piperidin-1-yl]-biphenyl-4-yl}carbamic acid tert.-butyl ester Prepared from (RS)-{4'-fluoro-5-nitro-2-4-(tetrahydro-pyran-2-yloxy)-piperidin-1-yl]-biphenyl-4-yl}-carbamic acid tert.-butyl ester (Example F3) (845 mg, 1.64 mmol) by catalytic hydrogenation with Pd/C according to the general procedure L (method a). Obtained as a light green solid (758 mg).

MS (ISP) 486 [(M+H)$^+$]; mp 157–161° C.

Example L32

[2-Amino-5-(2-tert.-butoxy-ethoxy)-4-(4-fluoro-phenylethynyl)-phenyl]-carbamic acid tert.-butyl ester Prepared from [5-(2-tert.-butoxy-ethoxy)-4-(4-fluoro-phenylethynyl)-2-nitro-phenyl]-carbamic acid tert.-butyl ester (Example K25) (744 mg, 1.57 mmol) by reduction with $SnCl_2.2H_2O$ according to the general procedure L (method b). Obtained as a light yellow solid (575 mg).

MS (ISP) 443 [(M+H)$^+$]; mp 149–150 C.

Example L33

(RS)-(5-Amino-4'-fluoro-2-{4-[2-(tetrahydro-pyran-2-yloxy)-ethoxy]-piperidin-1-yl}-biphenyl-4-yl)-carbamic acid tert.-butyl ester Prepared from (RS)-(4'-fluoro--nitro-2-{4-[2-(tetrahydro-pyran-2-yloxy)-ethoxy]-piperidin-1-yl}-biphenyl-4-yl)-carbamic acid tert.-butyl ester (Example F4) (900 mg, 1.61 mmol) by catalytic hydrogenation with Pd/C according to the general procedure L (method a). Obtained as a light brown foam (779 mg).

MS (ISP) 530 [(M+H)$^+$]; mp 56–58° C.

Example L34

(RS)-[5-Amino-4'-fluoro-2-(tetrahydro-pyran-2-yloxymethyl)-biphenyl-4-yl -carbamic acid tert-butyl ester Prepared from (RS)-[4'-fluoro-5-nitro-2-(tetrahydro-pyran-2-yloxymethyl)-biphenyl-4-yl]-carbamic acid tert.-butyl ester (Example F5) by reduction with $SnCl_2.2H_2O$ according to the general procedure L (method b). Obtained as an orange solid (1.15 g).

mp 139–142° C.

Example L35

(5-Amino-2-cyanomethoxy-4'-fluoro-biphenyl-4-yl)-carbamic acid tert.-butyl ester Prepared from (2-cyanomethoxy-4'-fluoro-5-nitro-biphenyl-4-yl)-carbamic acid tert.-butyl ester (Example F6) (310 mg, 0.8 mmol) by reduction with $SnCl_2.2H_2O$ according to the general procedure L (method b). Obtained as a light brown solid (220 mg).

MS (ISN) 356 [(M–H)$^-$]; mp 118–119° C.

Example L36

(5-Amino-2-dimethylaminomethyl-4'-fluoro-biphenyl-4-yl)-carbamic acid tert.-butyl ester Prepared from (2-dimethylaminomethyl-4'-fluoro-5-nitro-biphenyl-4-yl)-carbamic acid tert.-butyl ester (Example F7) by reduction with $SnCl_2.2H_2O$ according to the general procedure L (method b). Obtained as a yellow solid (908 mg).

mp 97–125° C.

Example L37

[5-Amino-2-(2,2-dimethyl-tetrahydro-[1,3]dioxolo[4,5-c]pyrrol-5-yl)-4'-fluoro-biphenyl-4-yl]-carbamic acid tert.-butyl ester Prepared from [2-(2,2-dimethyl-tetrahydro-(1,3]dioxolo[4,5-c]pyrrol-5-yl)-4'-fluoro-5-nitro-biphenyl-4-yl]-carbamic acid tert.-butyl ester (Example F8) (610 mg, 1.29 mmol) by catalytic hydrogenation with Pd/C according to the general procedure L (method a). Obtained as an off-white foam (578 mg).

MS (ISP) 444 [(M+H)$^+$].

Example L38

(5-Amino-4'-fluoro-2-methoxy-biphenyl-4-yl)-carbamic acid tert.-butyl ester

Prepared from (4'-fluoro-2-methoxy-5-nitro-biphenyl-4-yl)-carbamic acid tert.-butyl ester (Example F9) (2.64 g, 7.29 mmol) by catalytic hydrogenation with Pd/C according to the general procedure L (method a). Obtained as an off-white solid (2.36 g).

MS (ISP) 333 [(M+H)$^+$]; mp 155° C. (dec.).

Example L39

[5-Amino-2-(1,4-dioxa-8-aza-spiro[4.5]dec-8-yl)-4'-fluoro-biphenyl-4-yl]-carbamic acid tert.-butyl ester Prepared from [2-(1,4-dioxa-8-aza-spiro[4.5]dec-8-yl)-4'-fluoro-5-nitro-biphenyl-4-yl]-carbamic acid tert.-butyl ester (Example F10) (2.4 g, 5.0 mmol) by catalytic hydrogenation with Pd/C according to the general procedure L (method a). Obtained as a green solid (2.37 g).

MS (ISP) 444 [(M+H)$^+$].

Example L40

(5-Amino-4'-fluoro-2-methyl-biphenyl-4-yl)-carbamic acid tert.-butyl ester

Prepared from (4'-fluoro-2-methyl-5-nitro-biphenyl-4-yl)-carbamic acid tert.-butyl ester (Example F11) (560 mg, 1.62 mmol) by catalytic hydrogenation with Pd/C according to the general procedure L (method a). Obtained as a light brown solid (512 mg).

MS (ISP) 317 [(M+H)$^+$]; mp 112° C.

Example L41

(5-Amino-4-tert.-butoxycarbonylamino-4'-fluoro-biphenyl-2-yloxy)-acetic acid tert.-butyl ester Prepared from (4-tert.-butoxycarbonylamino-4'-fluoro-5-nitro-biphenyl-2-yloxy)-acetic acid tert.-butyl ester (Example F12) (2.29 g, 4.95 mmol) by catalytic hydrogenation with Pd/C according to the general procedure L (method a). Obtained as a dark blue solid (2.14 g).

MS (ISP) 433 [(M+H)$^+$]; mp 30–33° C.

Example L42

(5-Amino-2-chloro-4'-fluoro-biphenyl-4-yl)-carbamic acid tert.-butyl ester

Prepared from (2-chloro-4'-fluoro-5-nitro-biphenyl-4-yl)-carbamic acid tert.-butyl ester (Example F13) by reduction with $SnCl_2.2H_2O$ according to the general procedure L (method b). Obtained as a light red solid (544 mg).

MS (ISP) 337 [(M+H)$^+$].

Example L43

[5-Amino-4'-fluoro-2-(2-methoxy-ethoxy)-biphenyl-4-yl]-carbamic acid tert.-butyl ester Prepared from [4'-fluoro-2-(2-methoxy-ethoxy)-5-nitro-biphenyl-4-yl]-carbamic acid tert.-butyl ester (Example F14) by catalytic hydrogenation with Pd/C according to the general procedure L (method a). Obtained as a light brown solid (1.652 g).

MS (ISP) 377 [(M+H)+].

Example L44

[5-Amino-2-(2-tert.-butoxy-ethoxy)-4'-fluoro-biphenyl-4-yl]-carbamic acid tert.-butyl ester Prepared from [2-(2-tert.-butoxy-ethoxy)-4'-fluoro-5-nitro-biphenyl-4-yl]-carbamic acid tert.-butyl ester (Example F15) by catalytic hydrogenation with Pd/C according to the general procedure L (method a). Obtained as a purple solid (547 mg).

MS (ISP) 419 [(M+H)$^{30}$ ]; mp 133° C. (dec.).

Example L45

[5-Amino-4'-fluoro-2-(2-oxo-oxazolidin-3-yl)-biphenyl-4-yl]-carbamic acid tert.-butyl ester Prepared from [4'-fluoro-5-nitro-2-(2-oxo-oxazolidin-3-yl)-biphenyl-4-yl]-carbamic acid tert.-butyl ester (Example F16) (280 mg, 0.67 mmol) by catalytic hydrogenation with Pd/C according to the general procedure L (method a). Obtained as a yellow solid (277 mg).

MS (ISP) 388 [(M+H)+]; mp 210° C.

Example L46

(5-Amino-4'-fluoro-2-methoxy-2'-methyl-biphenyl-4-y)-carbamic acid tert.-butyl ester Prepared from (4'-fluoro-2-methoxy-2'-methyl-5-nitro-biphenyl-4-yl)-carbamic acid tert.-butyl ester (Example F17) by catalytic hydrogenation with Pd/C according to the general procedure L (method a). Obtained as a brown solid (588 mg).

MS (ISP) 347 [(M+H)+].

Example L47

(5-Amino-2-tert.-butoxy-4'-fluoro-biphenyl-4-yl)-carbamic acid tert.-butyl ester Prepared from (2-tert.-butoxy-4'-fluoro-5-nitro-biphenyl-4-yl)-carbamic acid tert.-butyl ester (Example F18) (1.15 g, 2.84 mmol) by catalytic hydrogenation with Pd/C according to the general procedure L (method a). Obtained as a pink solid (747 mg).

MS (ISP) 375 [(M+H)+]; mp 139° C.

Example L48

(5-Amino-2-tert.-butoxy-2'-fluoro-biphenyl-4-yl)-carbamic acid tert.-butyl ester Prepared from (2-tert.-butoxy-2'-fluoro-5-nitro-biphenyl-4-yl)-carbamic acid tert.-butyl ester (Example F19) (930 mg, 2.3 mmol) by catalytic hydrogenation with Pd/C according to the general procedure L (method a). Obtained as a pink solid (649 mg).

MS (ISP) 375 [(M+H)+]; mp 130° C.

Example L49

(RS)-{5-Amino-4'-fluoro-2-[(R)-3-(tetrahydro-pyran-2-yloxy)-pyrrolidin-1-yl]-biphenyl -4-yl}-carbamic acid tert.-butyl ester Prepared from (RS)-{4'-fluoro-5-nitro-2-[(R)-3-(tetrahydro-pyran-2-yloxy)-pyrrolidin-1-yl]-biphenyl-4-yl}-carbamic acid tert.-butyl ester (Example F20) by catalytic hydrogenation with Pd/C according to the general procedure L (method a). Obtained as a dark green solid (852 mg).

MS (ISP) 472 [(M+H)+].

Example L50

(5-Amino-2'-fluoro-2-methoxy-biphenyl-4-yl)-carbamic acid tert.-butyl ester

Prepared from (2'-fluoro-2-methoxy-5-nitro-biphenyl-4-yl)-carbamic acid tert.-butyl ester (Example F21) (649 mg, 1.79 mmol) by catalytic hydrogenation with Pd/C according to the general procedure L (method a). Obtained as a light brown solid (352 mg).

MS (ISP) 333 [(M+H)+]; mp 161° C.

Example L51

[5-Amino-2-(1,4-dioxa-8-aza-spiro[4.5]dec-8-yl)-2'-fluoro-biphenyl-4-yl]-carbamic acid tert.-butyl ester Prepared from [2-(1,4-dioxa-8-aza-spiro[4.5]dec-8-yl)-2'-fluoro-5-nitro-biphenyl-4-yl]-carbamic acid tert.-butyl ester (Example F22) (1.39 g, 2.94 mmol) by catalytic hydrogenation with Pd/C according to the general procedure L (method a). Obtained as a light beige solid (1.01 g).

MS (ISP) 444 [(M+H)+]; mp 198° C.

Example L52

(5-Amino-2',5'-difluoro-2-methoxy-biphenyl-4-yl)-carbamic acid tert.-butyl ester Prepared from (2',5'-difluoro-2-methoxy-5-nitro-biphenyl-4-yl)-carbamic acid tert.-butyl ester (Example F23) (1.05 g, 2.76 mmol) by catalytic hydrogenation with Pd/C according to the general procedure L (method a). Obtained as a beige solid (618 mg).

MS (ISN) 349 [(M−H)−]; mp 144° C.

Example L53

[5-Amino-2'-fluoro-2-(2-methoxy-ethoxy)-biphenyl-4-yl]-carbamic acid tert.-butyl ester Prepared from [2'-fluoro-2-(2-methoxy-ethoxy)-5-nitro-biphenyl-4-yl]carbamic acid tert.-butyl ester (Example F24) by catalytic hydrogenation with Pd/C according to the general procedure L (method a). Obtained as a purple solid (2.581 g).

Example L54

(RS)-[5-Amino-2'-fluoro-2-(tetrahydro-pyran-2-yloxymethyl)-biphenyl-4-yl]-carbamic acid tert.-butyl ester Prepared from (RS)-[2'-fluoro-5-nitro-2-(tetrahydro-pyran-2-yloxymethyl)-biphenyl-4-yl]-carbamic acid tert.-butyl ester (Example F25) by reduction with $SnCl_2.2H_2O$ according to the general procedure L (method b). Obtained as a yellow liquid (2.676 g).

MS (ISP) 439 [(M+Na)+].

Example L55

[5-Amino-2'-fluoro-2-(4-methoxy-benzyloxy)-biphenyl-4-yl]-carbamic acid tert.-butyl ester Prepared from [2'-fluoro-2-(4-methoxy-benzyloxy)-5-nitro-biphenyl-4-yl]-carbamic acid tert.-butyl ester (Example F25) (0.90 g, 1.92 mmol) by reduction with SnCl$_2$.2H$_2$O according to the general procedure L (method b). Obtained as a beige solid (719 mg).

MS (ISP) 439 [(M+H)$^+$].

Example L56

(5-Amino-2-tert.-butoxy-2',5'-difluoro-biphenyl-4-yl)-carbamic acid tert.-butyl ester Prepared from (2-tert.-butoxy-2',5'-difluoro-5-nitro-biphenyl-4-yl)-carbamic acid tert.-butyl ester (Example F27) by catalytic hydrogenation with Pd/C according to the general procedure L (method a). Obtained as an amorphous grey-blue substance (2.37 g).

MS (ISP) 393 [(M+H)$^+$].

Example L57

[2-Amino-5-tert.-butoxy-4-(4-fluoro-phenylethynyl)-phenyl]-carbamic acid tert.-butyl ester Prepared from [5-tert.-butoxy-4-(4-fluoro-phenylethynyl)-2-nitro-phenyl]-carbamic acid tert.-butyl ester (Example K26) (649 mg, 1.51 mmol) by reduction with SnCl$_2$.2H$_2$O according to the general procedure L (method b). Obtained as a light yellow solid (410 mg).

MS (ISP) 399 [(M+H)$^+$]; mp 183° C.

The following examples relate to the preparation of the ethyl or tert.-butyl 3-aryl-3-oxo-propionates (formula VIIa), which serve as building blocks in the synthesis of the target compounds (Synthetic Scheme H):

General Procedure M

Method a) Preparation of ethyl or tert.-butyl 3-aryl-3-oxo-propionates

The ethyl or tert.-butyl 3-aryl-3-oxo-propionates were prepared from the aryl acid chlorides and ethyl or tert.-butyl malonate potassium salt [CAS-no. 6148-64-7 and 75486-33-8] with Et$_3$N and MgCl$_2$ in CH$_3$CN at 0° C. to 23° C. according to *Synthesis* 1993, 290. If the carboxylic acid was employed in this reaction, it was activated by treatment with ethyl chloroformate and Et$_3$N in THF/CH$_3$CN at 0° C. prior to reaction with the malonate salt.

Method b) Preparation of tert.-butyl 3-aryl-3-oxo-propionates

The tert.-butyl 3-aryl-3-oxo-propionates were alternatively prepared from the methyl or ethyl aryl esters by treatment with lithium tert.-butyl acetate [prepared by treatment of tert.-butyl acetate with lithium diisopropylamide in THF at −78° C.] in the presence of lithium tert.-butoxide according to *Synthesis* 1985, 45. If the product contained residual starting material after workup, thus could be removed by selective saponification with LiOH in THF/MeOH/H$_2$O at 23° C.

Method c) Preparation of 3-aryl-3-oxo-propionic acids

The 3-aryl-3-oxo-propionic acids were prepared from the aryl acid chlorides and bis(trimethylsilyl)malonate with Et$_3$N and LiBr in CH$_3$CN at 0° C. according to *Synth. Commun.* 1985, 15, 1039 (method c1) or with n-BuLi in ether at −60° C. to 0° C. according to *Synthesis* 1979, 787 (method c2).

Example M1

3-Oxo-3-(3-[1,2,4]triazol-4-yl-phenyl)-propionic acid ethyl ester

RO-71-2790/000

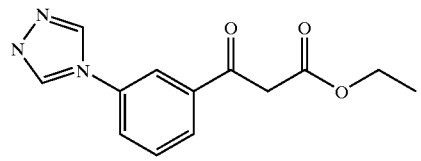

Prepared from 3-[1,2,4]triazol-4-yl-benzoic acid [RO-71-1432/000, prepared by reaction of 3-aminobenzoic acid with hydrazine hydrate and triethyl orthoformate in acetic acid at 120° C.] by activation with ethyl chloroformate/Et$_3$N and reaction with ethyl malonate potassium salt with Et$_3$N and MgCl$_2$ in CH$_3$CN according to general procedure M (method a). Obtained as a white solid (5.74 g).

MS (EI) 259 (M$^+$).

Example M2

3-Oxo-3-(3-[1,2,3]triazol-1-yl-phenyl)-propionic acid ethyl ester

Prepared from 3-[1,2,3]triazol-1-yl-benzoic acid [RO-71-3703/000, prepared by refluxing of methyl 3-azidobenzoate [CAS-No. 93066-93-4] in trimethylsilylacetylene, followed by saponification with aqueous NaOH in refluxing EtOH] by activation with ethyl chloroformate/Et$_3$N and reaction with ethyl malonate potassium salt with Et$_3$N and MgCl$_2$ in CH$_3$CN according to general procedure M (method a). Obtained as a light yellow solid (2.22 g).

MS (EI) 259 (M$^+$); mp 72–74° C.

Example M3

3-(3-Cyano-phenyl)-3-oxo-propionic acid tert.-butyl ester

Prepared from methyl 3-cyanobenzoate [CAS-No. 13531-48-1] by treatment with lithium tert.-butyl acetate according to general procedure M (method b). Obtained as a light brown oily semisolid.

MS (EI) 245 (M$^+$).

Example M4

3-(3-Imidazol-1-yl-phenyl)-3-oxo-propionic acid tert.-butyl ester

Prepared from methyl 3-(1H-imidazol-1-yl)benzoate [prepared from 3-(1H-imidazol-1-yl)benzoic acid (*J. Med. Chem.* 1987, 30, 1342; CAS-No. [108035-47-8] by refluxing in conc. H$_2$SO$_4$/MeOH] by treatment with lithium tert.-butyl acetate according to general procedure M (method b). Obtained as an orange-brown oil.

MS (ISP) 287 [(M+H)$^+$].

Example M5

3-(2-Imidazol-1-yl-pyridin-4-yl)-3-oxo-propionic acid tert.-butyl ester

Prepared from 2-imidazol-1-yl-isonicotinoyl chloride hydrochloride [prepared by reaction of tert.-butyl 2-chloroisonicotinoate with imidazole and NaH in DMF at 80° C., treatment with formic acid at 50° C. and reaction with thionylchloride in toluene at 100° C.] and tert.-butyl malonate potassium salt with Et$_3$N and MgCl$_2$ in CH$_3$CN according to general procedure M (method a). Obtained as a brown solid (10.8 g).

MS (EI) 287 (M$^+$); mp 80° C. (dec.).

Example M6

3-Oxo-3-(3-[1,2,4]triazol-1-yl-phenyl)-propionic acid tert.-butyl ester

Prepared from methyl 3-[1,2,4]triazol-1-yl-benzoate [CAS-No. 167626-27-9] by treatment with lithium tert.-butyl acetate according to general procedure M (method b). Obtained as an orange liquid (2.41 g).

MS (EI) 287 (M$^+$).

Example M7

3-[3-(4-Methyl-imidazol-1-yl)-phenyl]-3-oxo-propionic acid tert.-butyl ester

Prepared from methyl 3-(4-methyl-imidazol-1-yl)-benzoate [RO-69-6483/000, prepared the corresponding acid from 3-isothiocyanatobenzoic acid and 2-aminopropionaldehyde dimethyl acetal according to *J. Med. Chem.* 1987, 30, 1342, followed by refluxing in conc. H$_2$SO$_4$/MeOH] by treatment with lithium tert.-butyl acetate according to general procedure M (method b). Obtained as a yellow-brown oil (10.69 g).

MS (EI) 300 (M$^+$).

Example M8

3-[3-(2-Methyl-imidazol-1-yl)-phenyl]-3-oxo-propionic acid tert.-butyl ester

Prepared from ethyl 3-(2-methyl-imidazol-1-yl)-benzoate [RO-69-7480/000, prepared by reaction of ethyl 3-aminobenzoate with ethyl acetimidate hydrochloride in EtOH at 0° C., direct treatment with aminoacetaldehyde diethyl acetal in EtOH at 23° C., follwed by addition of conc. H$_2$SO$_4$ and refluxing.] by treatment with lithium tert.-butyl acetate according to general procedure M (method b). Obtained as a brown oil (9.66 g).

MS (ISN) 299 [(M–H)$^-$].

Example M9

3-[3-(2,4-Dimethyl-imidazol-1-yl)-phenyl]-3-oxo-propionic acid tert.-butyl ester Prepared from ethyl 3-(2,4-dimethyl-imidazol-1-yl)-benzoate [RO-71-0583/000, prepared by reaction of ethyl 3-aminobenzoate with ethyl acetimidate hydrochloride in EtOH at 0° C., direct treatment with 2-aminopropionaldehyde dimethyl acetal in EtOH at 23° C., follwed by addition of conc. H$_2$SO$_4$ and refluxing.] by treatment with lithium tert.-butyl acetate according to general procedure M (method b). Obtained as a yellow-brown oil (6.00 g).

MS (ISN) 313 [(M–H)$^-$].

Example M10

3-(2-Cyano-pyridin-4-yl)-3-oxo-propionic acid tert.-butyl ester

Prepared from 2-cyano-isonicotinic acid ethyl ester [CAS-No. 58481-14-4] by treatment with lithium tert.-butyl acetate according to general procedure M (method b). Obtained as a light brown solid (7.70 g).

MS (ISN) 245 [(M–H)$^-$].

Example M11

3-Oxo-3-(3-[1,2,4]triazol-4-yl-phenyl)-propionic acid tert.-butyl ester

Prepared from methyl 3-[1,2,4]triazol-4-yl-benzoate [prepared by reaction of 3-aminobenzoic acid with hydrazine hydrate and triethyl orthoformate in acetic acid at 120° C., followed by esterification with conc. H$_2$SO$_4$ in refluxing MeOH] by treatment with lithium tert.-butyl acetate according to general procedure M (method b). Obtained as a light yellow gum (870 mg).

MS (ISN) 286 [(M–H)$^-$].

Example M12

3-[3-(2-Methoxymethylsulfanyl-imidazol-1-yl)-phenyl]-3-oxo-propionic acid tert.-butyl ester Prepared from ethyl 3-(2-methoxymethylsulfanyl-imidazol-1-yl)-benzoate [prepared by esterification of 3-(2-methoxymethylsulfanyl-imidazol-1-yl)-benzoic acid [CAS-No. 108035-46-7] with conc. H$_2$SO$_4$ in EtOH, followed by treatment with chloromethylmethyl ether and NaH in THF/DMF] by treatment with lithium tert.-butyl acetate according to general procedure M (method b). Obtained as an orange oil (1.82 g).

MS (EI) 362 (M$^+$).

Example M13

3-[3-(2-Methylsulfanyl-imidazol-1-yl)-phenyl]-3-oxo-propionic acid tert.-butyl ester Prepared from ethyl 3-(2-methylsulfanyl-imidazol-1-yl)-benzoate [prepared by esterification of 3-(2-methoxymethylsulfanyl-imidazol-1-yl)-benzoic acid [CAS-No. 108035-46-7] with conc. H$_2$SO$_4$ in EtOH, followed by treatment methyl iodide and NaH in THF/DMF] by treatment with lithium tert.-butyl acetate according to general procedure M (method b). Obtained as a light brown oil (4.41 g).

MS (ISP) 333 [(M+H)$^+$].

Example M 14

3-[3-(3-Methyl-isoxazol-5-yl)-phenyl]-3-oxo-propionic acid tert.-butyl ester

Prepared from ethyl 3-(3-methyl-isoxazol-5-yl)-benzoate [prepared by reaction of ethyl 3-ethynylbenzoate [CAS-No. 178742-95-5] with a mixture of NCS, acetaldoxime, Et$_3$N and cat. amount of pyridine in CHCl$_3$ at 50° C. according to *Tetrahedron* 1984, 40, 2985–2988] by treatment with lithium tert.-butyl acetate according to general procedure M (method b). Obtained as a yellow solid (2.54 g).

MS (ISP) 302 [(M+H)$^+$]; mp 50–56° C.

Example M15

3-Oxo-3-(3-tetrazol-1-yl-phenyl)-propionic acid ethyl ester

Prepared from 3-tetrazol-1-yl-benzoic acid [CAS-No. 204196-80-5] by activation with ethyl chloroformate/Et$_3$N and reaction with ethyl malonate potassium salt with Et₃N and MgCl₂ in CH₃CN according to general procedure M (method a). Obtained as a light yellow solid (211 mg).

MS (EI) 260 (M⁺).

Example M16

3-(3-Chloro-thiophen-2-yl)-3-oxo-propionic acid ethyl ester

Prepared from 3-chloro-2-thiophenecarbonyl chloride [CAS-No. 86427-02-3] by reaction with ethyl malonate potassium salt with Et₃N and MgCl₂ in CH₃CN according to general procedure M (method a). Obtained as a brown oil (6.84 g).

MS (EI) 232 (M⁺) and 234 [(M+2)⁺].

Example M17

3-(5-Cyano-thiophen-2-yl)-3-oxo-propionic acid tert.-butyl ester

Prepared from ethyl 5-cyano-2-thiophenecarboxylate [CAS-No. 67808-35-9] by treatment with lithium tert.-butyl acetate according to general procedure M (method b). Obtained as a yellow solid (6.66 g).

MS (EI) 251 (M⁺); mp 78° C.

Example M18

3-(5-Cyano-2-fluoro-phenyl)-3-oxo-propionic acid ethyl ester

Prepared from 5-cyano-2-fluoro-benzoyl chloride [prepared from the corresponding acid [CAS-No. 146328-87-2] by treatment with SOCl₂, cat. DMF in toluene at 80° C.] by reaction with ethyl malonate potassium salt with Et₃N and MgCl₂ in CH₃CN according to general procedure M (method a). Obtained as a light yellow solid (3.85 g).

MS (EI) 235 (M⁺); mp 55–60° C.

Example M19

3-(2-Imidazol-1-yl-thiazol-4-yl)-3-oxo-propionic acid tert.-butyl ester

Prepared from ethyl 2-imidazol-1-yl-thiazole-4-carboxylate [CAS-No. 256420-32-3] by treatment with lithium tert.-butyl acetate according to general procedure M (method b). Obtained as an orange oil (12.0 g).

Example M20

3-[2-(4-Methyl-imidazol-1-yl)-thiazol-4-yl]-3-oxo-propionic acid tert.-butyl ester Prepared from ethyl 2-(4-methyl-imidazol-1-yl)-thiazole-4-carboxylate [prepared from ethyl 2-amino-4-thiazolecarboxylate (CAS-No. [256420-32-3]) by the following synthetic sequence: 1.) NaH, 2-isothiocyanato-1,1-dimethoxy-propane, DMF, 23° C.; 2.) aq. H₂SO₄, reflux; 3.) EtOH, conc. H₂SO₄, 23° C.; 4.) 30% H₂O₂, HOAc, 23° C.] by treatment with lithium tert.-butyl acetate according to general procedure M (method b). Obtained as a brown oil (8.73 g).

MS (EI) 307 (M⁺).

Example M21

3-[3-(1-Methyl-1H-imidazol-2-yl)-phenyl]-3-oxo-propionic acid tert.-butyl ester

Prepared from ethyl 3-(1-methyl-1H-imidazol-2-yl) benzoate [CAS-No. 168422-44-4] by treatment with lithium tert.-butyl acetate according to general procedure M (method b). Obtained as a light yellow liquid (1.26 g).

MS (ISP) 301.3 [(M+H)⁺].

The following examples relate to the preparation of the 6-aryl-2,2-dimethyl-[1,3]dioxin-4-ones (formula VII), which serve as building blocks in the synthesis of the target compounds (Synthetic Scheme H):

General Procedure N

Preparation of 6-aryl-2,2-dimethyl-[1,3]dioxin-4-ones
Method a)

The 6-aryl-2,2-dimethyl-[1,3]dioxin-4-ones were prepared from 3-aryl-3-oxo-propionic acids and catalytic amount of conc. H₂SO₄ or trifluoroacetic acid (TFA) in isopropenyl acetate at 23° C. according to *Chem. Pharm. Bull.* 1983, 31, 1896. The final products were purified by silica gel column chromatography with hexane/EtOAc.
Method b)

The 6-aryl-2,2-dimethyl-[1,3]dioxin-4-ones were prepared from the tert.-butyl 3-aryl-3-oxo-propionates by treatment with trifluoroacetic anhydride (TFAA) in a mixture of TFA and acetone at 23° C. according to *Tetrahedron Lett.* 1998, 39, 2253. The final products were if necessary purified by silica gel column chromatography with hexane/EtOAc.

Example N1

2,2-Dimethyl-6-thiophen-2-yl-[1,3]dioxin-4-one

The 3-oxo-3-thiophen-2-yl-propionic acid was prepared from thiophene-2-carbonyl chloride (5.3 mL, 50 mmol) and bis(trimethylsilyl)malonate (25.6 mL, 100 mmol) with n-BuLi (1.6M in hexane, 62.5 mL) in ether at −60° C. to 0° C. according to the general procedure M (method c2). The crude material (7.88 g) was transformed into the title compound by stirring in isopropenyl acetate and TFA according to the general procedure N (method a). Obtained as a yellow solid (4.09 g).

MS (EI) 210 (M⁺); mp 42° C. (dec.).

Example N2

6-(3-Chloro-thiophen-2-yl)-2,2-dimethyl-[1,3]dioxin-4-one

The 3-(3-chloro-thiophen-2-yl)-3-oxo-propionic acid was prepared from 3-chloro-thiophene-2-carbonyl chloride (7.82 g, 43.2 mmol) and bis(trimethylsilyl)malonate (11.6 mL, 45.4 mmol) with Et₃N (12.65 mL, 90.7 mmol) and LiBr (3.53 g, 47.5 mmol) in CH₃CN at 0° C. according to general procedure M (method c1). The crude material (5.69 g) was transformed into the title compound by stirring in isopropenyl acetate and conc. H₂SO₄ according to general procedure N (method a). Obtained as an orange solid (2.3 g).

MS (EI) 244 (M⁺) and 246 [(M+2)⁺]; mp 88–89° C. (dec.).

Example N3

6-(3-Cyano-thiophen-2-yl)-2,2-dimethyl-[1,3]dioxin-4-one

The 3-(3-cyano-thiophen-2-yl)-3-oxo-propionic acid was prepared from 3-cyano-thiophene-2-carbonyl chloride (24.33 g, 140.6 mmol) and bis(trimethylsilyl)malonate (38.0 mL, 147.7 mmol) with Et₃N (41 mL, 295.4 mmol) and LiBr (13.5 g, 154.7 mmol) in CH₃CN at 0° C. according to general procedure M (method c1). The crude material (24.8 g) was transformed into the title compound by stirring in isopropenyl acetate and conc. H$_2$SO$_4$ according to general procedure N (method a). Obtained as an orange solid (5.6 g).

MS (EI) 235 (M$^+$); mp 116–120° C. (dec.).

Example N4

3-(2,2-Dimethyl-6-oxo-6H-[1,3]dioxin-4-yl)-benzonitrile

The 3-(3-cyano-phenyl)-3-oxo-propionic acid was prepared from 3-cyanobenzoyl chloride (828 mg, 5 mmol) and bis(trimethylsilyl)malonate (2.56 mL, 10 mmol) with n-BuLi (1.6M in hexane, 6.25 mL) in ether at –60° C. to 0° C. according to general procedure M (method c2). The crude material (1.04 g) was transformed into the title compound by stirring in isopropenyl acetate and TFA according to general procedure N (method a). Obtained as a light yellow solid (0.8 g).

MS (EI) 229 (M$^+$); mp 138° C. (dec.).

Example N5

2,2-Dimethyl-6-(3-trifluoromethyl-phenyl)-[1,3]dioxin-4-one

The 3-oxo-3-(3-trifluoromethyl-phenyl)-propionic acid was prepared from 3-trifluoromethylbenzoyl chloride (10 mL, 67.6 mmol) and bis(trimethylsilyl)malonate (18.2 mL, 71 mmol) with Et$_3$N (20 mL, 142 mmol) and LiBr (6.46 g, 74.4 mmol) in CH$_3$CN at 0° C. according to general procedure M (method c1). The crude material (7.0 g of the obtained 15.4 g) was transformed into the title compound by stirring in isopropenyl acetate and conc. H$_2$SO$_4$ according to general procedure N (method a). Obtained as a light yellow solid (5.3 g).

MS (EI) 272 (M$^+$); mp 77–78° C. (dec.).

Example N6

6-(3-Chloro-phenyl)-2,2-dimethyl-[1,3]dioxin-4-one

The 3-(3-chloro-phenyl)-3-oxo-propionic acid was prepared from 3-chlorobenzoyl chloride (11 mL, 85.7 mmol) and bis(trimethylsilyl)malonate (23.0 mL, 90.0 mmol) with Et$_3$N (25 mL, 180 mmol) and LiBr (8.19 g, 94.3 mmol) in CH$_3$CN at 0° C. according to general procedure M (method c1). The crude material (17.1 g) was transformed into the title compound by stirring in isopropenyl acetate and conc. H$_2$SO$_4$ according to general procedure N (method a). Obtained as a yellow-brown solid (8.0 g).

MS (EI) 238 (M$^+$) and 240 [(M+2)$^+$]; mp 87–88° C. (dec.).

Example N7

6-(3-Iodo-phenyl)-2,2-dimethyl-[1,3]dioxin-4-one

The 3-(3-iodo-phenyl)-3-oxo-propionic acid was prepared from 3-iodobenzoyl chloride (21.0 g, 78.8 mmol) and bis(trimethylsilyl)malonate (21.0 mL, 82.8 mmol) with Et$_3$N (23 mL, 165.5 mmol) and LiBr (7.54 g, 86.7 mmol) in CH$_3$CN at 0° C. according to general procedure M (method c1). The crude material (21.9 g) was transformed into the title compound by stirring in isopropenyl acetate and conc. H$_2$SO$_4$ according to general procedure N (method a). Obtained as a yellow solid (9.6 g).

MS (EI) 330 (M$^+$); mp 79–80° C. (dec.).

Example N8

2,2-Dimethyl-6-(3-trifluoromethoxy-phenyl)-[1,3]dioxin-4-one

The 3-oxo-3-(3-trifluoromethoxy-phenyl)-propionic acid was prepared from 3-trifluoromethoxybenzoyl chloride and bis(trimethylsilyl)malonate with Et$_3$N and LiBr in CH$_3$CN at 0° C. according to general procedure M (method c1). The crude material was transformed into the title compound by stirring in isopropenyl acetate and conc. H$_2$SO$_4$ according to general procedure N (method a). Obtained as an orange solid (2.27 g).

MS (EI) 288 (M$^+$); mp 49–54° C. (dec.).

Example N9

2,2-Dimethyl-6-pyridin-4-yl-[1,3]dioxin-4-one

Prepared from 3-oxo-3-pyridin-4-yl-propionic acid [prepared from 4-acetylpyridine, magnesium methylcarbonate and CO$_2$ in DMF at 120° C. according to *Journal of Antibiotics* 1978, 31, 1245] by treatment with acetone, TFA and TFAA according to general procedure N (method b). Obtained as a white solid (1.3 g).

MS (EI) 205 (M$^+$)

Example N10

6-(3-Imidazol-1-yl-phenyl)-2,2-dimethyl-[1,3]dioxin-4-one

The 3-(3-imidazol-1-yl-phenyl)-3-oxo-propionic acid was prepared from 3-(1H-imidazol-1-yl)benzoyl chloride hydrochloride [prepared by treatment of 3-(1H-imidazol-1-yl)benzoic acid (*J. Med. Chem.* 1987, 30, 1342; CAS-No. [108035-47-8] with SOCl$_2$) and bis(trimethylsilyl)malonate with Et$_3$N and LiBr in CH$_3$CN at 0° C. according to general procedure M (method c1). The crude material was transformed into the title compound by stirring in isopropenyl acetate and conc. H$_2$SO$_4$ according to general procedure N (method a). Obtained as an orange semisolid (617 mg).

MS (EI) 270 (M$^+$).

Example N11

2,2-Dimethyl-6-(3-methoxy-phenyl)-[1,3]dioxin-4-one

The 3-(3-methoxy-phenyl)-3-oxo-propionic acid was prepared from 3-methoxybenzoyl chloride (10.3 g, 60.4 mmol) and bis(trimethylsilyl)malonate (16.2 mL, 63.4 mmol) with Et$_3$N (17.7 mL, 127 mmol) and LiBr (5.77 g, 66.4 mmol) in CH$_3$CN at 0° C. according to general procedure M (method c1). The crude material (6.38 g) was transformed into the title compound by stirring in isopropenyl acetate and conc. H$_2$SO$_4$ according to general procedure N (method a). Obtained as a yellow oil (640 mg).

MS (ISP) 235 [(M+H)$^+$] and 252 [(M+NH$_4$)$^+$].

Example N12

2,2-Dimethyl-6-(3-nitro-phenyl)-[1,3]dioxin-4-one

The 3-(3-nitro-phenyl)-3-oxo-propionic acid tert.-butyl ester was prepared from 3-nitrobenzoyl chloride (2.71 g, 14.6 mmol) and tert.-butyl malonate potassium salt (6.0 g, 30.0 mmol) with Et$_3$N (4.5 mL, 32.2 mmol) and MgCl$_2$ (3.48 g, 36.52 mmol) in CH$_3$CN according to general procedure M (method a). The crude material (3.88 g) was transformed into the title compound by stirring in TFA/acetone with TFAA according to general procedure N (method b). Obtained as a yellow solid (2.76 g).

MS (EI) 249 (M$^+$); mp 110–117° C.

Example N13

2,2-Dimethyl-6-(3-[1,2,4]triazol-1-yl-phenyl)-[1,3]dioxin-4-one

The 3-oxo-3-(3-[1,2,4]triazol-1-yl-phenyl)-propionic acid tert.-butyl ester [RO-69-3506/000] was prepared from 3-[1, 2,4]triazol-1-yl-benzoic acid methyl ester [CAS-No. 167626-27-9] by treatment with lithium tert.-butyl acetate according to general procedure M (method b). Prepared from (Example M6) by stirring in TFA/acetone with TFAA according to general procedure N (method b). Obtained as a yellow solid (539 mg).

MS (EI) 271 (M$^+$).

Example N14

6-(2-Imidazol-1-yl-pyridin-4-yl)-2,2-dimethyl-[1,3] dioxin-4-one

Prepared from 3-(2-imidazol-1-yl-pyridin-4-yl)-3-oxo-propionic acid tert.-butyl ester (Example M5) by stirring in TFA/acetone with TFAA according to general procedure N (method b). Obtained as a brown solid (10.8 g).

MS (EI) 271 (M$^+$); mp 151° C. (dec.).

Example N15

2,2-Dimethyl-6-[3-(2-methyl-imidazol-1-yl)-phenyl]-[1,3]dioxin-4-one

Prepared from 3-[3-(2-methyl-imidazol-1-yl)-phenyl]-3-oxo-propionic acid tert.-butyl ester (Example M8) by stirring in TFA/acetone with TFAA according to general procedure N (method b). Obtained as a beige solid (2.13 g).

MS (EI) 284 (M$^+$); mp 122° C.

Example N16

4-(2,2-Dimethyl-6-oxo-6H-[1,3]dioxin-4-yl)-pyridine-2-carbonitrile

Prepared from 3-(2-cyano-pyridin-4-yl)-3-oxo-propionic acid tert.-butyl ester (Example M10) by stirring in TFA/acetone with TFAA according to general procedure N (method b). Obtained as a brown solid (3.30 g).

MS (EI) 230 (M$^+$); mp 132° C. (dec.).

The following examples relate to the preparation of the 4,8-diaryl-1,3-dihydro-benzo[b][1,4]diazepin-2-ones, respectively the 4-aryl-8-arylethynyl-1,3-dihydro-benzo[b][1,4]diazepin-2-ones and the 8-aroyl-4-aryl-1,3-dihydro-benzo[b][1,4]diazepin-2-ones in regioisomerically pure fashion (Synthetic Scheme A):

General Procedure O

Preparation of {2-[3-aryl-3-oxo-propionylamino]-4-aryl-phenyl}-carbamic acid tert.-butyl ester by reaction of (2-amino-4-aryl-phenyl)-carbamic acid tert.-butyl esters with ethyl 3-aryl-3-oxo-propionates or 6-aryl-2,2-dimethyl-[1,3]dioxin-4-ones also 3-aryl-N-(2-nitro-4-aryl-phenyl)-3-oxo-propionamides by reaction of 2-nitro-4-aryl-phenylamines with 6-aryl-2,2-dimethyl-[1,3]dioxin-4-ones A mixture of the (2-amino-4-aryl-phenyl)-carbamic acid tert.-butyl ester or 2-nitro-4-aryl-phenylamine (1.0 mmol) and excess (1.2–1.5 mmol) of the ethyl 3-aryl-3-oxo-propionate [prepared from the aryl acid chloride and ethyl malonate potassium salt with Et$_3$N and MgCl$_2$ in CH$_3$CN at 23° C. according to *Synthesis* 1993, 290] or 6-aryl-2,2-dimethyl-[1,3]dioxin-4-one was refluxed in toluene (8 mL) until tlc indicated complete consumption of the amine. The solution was allowed to cool to 23° C., whereupon the product generally crystallized (in cases where crystallization failed to appear it was induced by addition of hexane). The solid was filtered off, washed with ether or mixtures of ether/hexane and dried in vacuum to give the {2-[3-aryl-3-oxo-propionylamino]-4-aryl-phenyl}-carbamic acid tert.-butyl esters or 3-aryl-N-(2-nitro-4-aryl-phenyl)-3-oxo-propionamides, which was used directly in the following step or —if necessary —was purified by recrystallization or by silica gel column chromatography.

Example O1

{2-[3-(3-Cyano-phenyl)-3-oxo-propionylamino]-4-iodo-5-thiomorpholin-4-yl-phenyl}-carbamic acid tert.-butyl ester Prepared from (2-amino-4-iodo-5-thiomorpholin-4-yl-phenyl)-carbamic acid tert.-butyl ester (Example L1) (653 mg, 1.5 mmol) and 3-(2,2-dimethyl-6-oxo-6H-[1,3]dioxin-4-yl)-benzonitrile (Example N4) (690 mg, 2.25 mmol) according to the general procedure O. Obtained as a yellow solid (629 mg).

MS (ISP) 607 [(M+H)$^+$].

Example O2

{2-[3-(3-Cyano-phenyl)-3-oxo-propionylamino]-4-iodo-5-morpholin-4-yl-phenyl}-carbamic acid tert.-butyl ester Prepared from (2-amino-4-iodo-5-morpholin-4-yl-phenyl)-carbamic acid tert.-butyl ester (Example L2) (690 mg, 1.65 mmol) and 3-(2,2-dimethyl-6-oxo-6H-[1,3]dioxin-4-yl)-benzonitrile (Example N4) (566 mg, 2.47 mmol) according to the general procedure O. Obtained as an orange solid (523 mg).

MS (ISP) 591 [(M+H)$^+$] and 613 [(M+Na)$^+$].

Example O3

{2-Chloro-5-[3-(3-cyano-phenyl)-3-oxo-propionylamino]-biphenyl-4-yl}-carbamic acid tert.-butyl ester Prepared from (5-amino-2-chloro-biphenyl-4-yl)-carbamic acid tert.-butyl ester (Example L6) (652 mg, 2.05 mmol) and 3-(2,2-dimethyl-6-oxo-6H-[1,3]dioxin-4-yl)-benzonitrile (Example N4) (564 mg, 2.46 mmol) according to the general procedure O. Obtained as an off-white solid (725 mg).

MS (ISN) 488 [(M−H)$^-$].

Example O4

[2-[3-(3-Cyano-phenyl)-3-oxo-propionylamino]-5-(2-dimethylamino-ethylsulfanyl)-4-phenylethynyl-phenyl]-carbamic acid tert.-butyl ester Prepared from [2-amino-5-(2-dimethylamino-ethylsulfanyl)-4-phenylethynyl-phenyl]-carbamic acid tert.-butyl ester (Example L8) (206 mg, 0.5 mmol) and 3-(2,2-dimethyl-6-oxo-6 H-[1,3]dioxin-4-yl)-benzonitrile (Example N4) (138 mg, 0.6 mmol) according to the general procedure O. Obtained as a yellow solid (210 mg).

MS (ISP) 583 [(M+H)$^+$]; mp 88° C.

Example O5

{5-tert.-Butoxycarbonylamino-4-[3-(3-cyano-phenyl)-3-oxo-propionylamino]-2-phenylethynyl-phenylsulfanyl}-acetic acid methyl ester Prepared from (4-amino-5-tert.-butoxycarbonylamino-2-phenylethynyl-phenylsulfanyl)-acetic acid methyl ester (Example L9) (534 mg, 1.3 mmol) and 3-(2,2-dimethyl-6-oxo-6H-[1,3]dioxin-4-yl)-benzonitrile (Example N4) (358 mg, 1.56 mmol) according to the general procedure O. Obtained as a yellow foam (457 mg).

MS (ISP) 584 [(M+H)$^+$], 601 [(M+NH$_4$)$^+$] and 605 [(M+Na)$^+$]; mp 69–73° C.

Example O6

{5-tert.-Butoxycarbonylamino-4-[3-(3-cyano-phenyl)-3-oxo-propionylamino]-2-phenylethynyl-phenyl}-acetic acid methyl ester Prepared from (4-amino-5-tert.-butoxycarbonylamino-2-phenylethynyl-phenyl)-acetic acid methyl ester (Example L10) (721 mg, 2.0 mmol) and 3-(2,2-dimethyl-6-oxo-6H-[1,3]dioxin-4-yl)-benzonitrile (Example N4) (550 mg, 2.4 mmol) according to the general procedure O. Obtained as a light yellow solid (886 mg).

MS (ISP) 552 [(M+H)$^+$] and 569 [(M+NH$_4$)$^+$]; mp 138° C.

Example O7

[2-[3-(3-Cyano-phenyl)-3-oxo-propionylamino]-5-(2-methoxy-ethoxy)-4-phenylethynyl-phenyl]-carbamic acid tert.-butyl ester Prepared from [2-amino-5-(2-methoxy-ethoxy)-4-phenylethynyl-phenyl]-carbamic acid tert.-butyl ester (Example L11) (415 mg, 1.09 mmol) and 3-(2,2-dimethyl-6-oxo-6H-[1,3]dioxin-4-yl)-benzonitrile (Example N4) (373 mg, 1.63 mmol) according to the general procedure O. Obtained as a light yellow solid (137 mg).

MS (ISP) 554 [(M+H)$^+$], 571 [(M+NH$_4$)$^+$] and 576 [(M+Na)$^+$]; mp 175–176° C.

Example O8

{2-[3-(3-Cyano-phenyl)-3-oxo-propionylamino]-5-methoxy-4-phenylethynyl-phenyl}-carbamic acid tert.-butyl ester Prepared from (2-amino-5-methoxy-4-phenylethynyl-phenyl)-carbamic acid tert.-butyl ester (Example L12) (338 mg, 1.0 mmol) and 3-(2,2-dimethyl-6-oxo-6H-[1,3]dioxin-4-yl)-benzonitrile (Example N4) (252 mg, 1.1 mmol) according to the general procedure O. Obtained as a yellow solid (388 mg).

MS (ISP) 510 [(M+H)$^+$], 527 [(M+NH$_4$)$^+$] and 532 [(M+Na)$^+$]; mp 169° C.

Example O9

5-tert.-Butoxycarbonylamino-4-[3-(3-cyano-phenyl)-3-oxo-propionylamino]-2-phenylethynyl-benzoic acid methyl ester Prepared from 4-amino-5-tert.-butoxycarbonylamino-2-phenylethynyl-benzoic acid methyl ester (Example L14) (396 mg, 1.08 mmol) and 3-(2,2-dimethyl-6-oxo-6H-[1,3]dioxin-4-yl)-benzonitrile (Example N4) (273 mg, 1.19 mmol) according to the general procedure O. Obtained as an off-white solid (540 mg).

MS (ISP) 538 [(M+H)$^+$], 555 [(M+NH$_4$)$^+$] and 560 [(M+Na)$^+$]; mp 158° C. (dec.).

Example O10

{2-[3-(3-Cyano-phenyl)-3-oxo-propionylamino]-5-morpholin-4-yl-4-phenylethynyl-phenyl}-carbamic acid tert.-butyl ester Prepared from (2-amino-5-morpholin-4-yl-4-phenylethynyl-phenyl)-carbamic acid tert.-butyl ester (Example L12) (483 mg, 1.23 mmol) and 3-(2,2-dimethyl-6-oxo-6H-[1,3]dioxin-4-yl)-benzonitrile (Example N4) (422 mg, 1.84 mmol) according to the general procedure O. Obtained as an amorphous orange material (375 mg).

MS (ISP) 565 [(M+H)$^+$] and 587 [(M+Na)$^+$].

Example O11

[2-[3-(3-Cyano-phenyl)-3-oxo-propionylamino]-5-(2-{2-[2-(2-methoxy-ethoxy)-ethoxy]-ethoxy}-ethoxy)-4-phenylethynyl-phenyl]-carbamic acid tert.-butyl ester Prepared from [2-amino-5-(2-{2-[2-(2-methoxy-ethoxy)-ethoxy]-ethoxy}-ethoxy)-4-phenylethynyl-phenyl]-carbamic acid tert.-butyl ester (Example L15) (514 mg, 1.0 mmol) and 3-(2,2-dimethyl-6-oxo-6H-[1,3]dioxin-4-yl)-benzonitrile (Example N4) (344 mg, 1.5 mmol) according to the general procedure O. Obtained as a light yellow solid (353 mg).

MS (ISP) 686 [(M+H)$^+$] and 703 [(M+NH$_4$)$^+$]; mp 135–136° C.

Example O12

{5-tert.-Butoxycarbonylamino-4-[3-(3-cyano-phenyl)-3-oxo-propionylamino]-2-phenylethynyl-phenoxy}-acetic acid tert.-butyl ester Prepared from (4-amino-5-tert.-butoxycarbonylamino-2-phenylethynyl-phenoxy)-acetic acid tert.-butyl ester (Example L16) (877 mg, 2.0 mmol) and 3-(2,2-dimethyl-6-oxo-6H-[1,3]dioxin-4-yl)-benzonitrile (Example N4) (504 mg, 2.2 mmol) according to the general procedure O. Obtained as a yellow solid (723 mg).

MS (ISP) 610 [(M+H)$^+$], 627 [(M+NH$_4$)$^+$] and 632 [(M+Na)$^+$]; mp 95° C.

Example O13

{5-Cyanomethyl-2-[3-(3-cyano-phenyl)-3-oxo-propionylamino]-4-phenylethynyl-phenyl}-carbamic acid tert.-butyl ester Prepared from (2-amino-5-cyanomethyl-4-phenylethynyl-phenyl)-carbamic acid tert.-butyl ester (Example L17) (298 mg, 0.86 mmol) and 3-(2,2-dimethyl-6-oxo-6H-[1,3]dioxin-4-yl)-benzonitrile (Example N4) (218 mg, 0.95 mmol) according to the general procedure O. Obtained as a yellow solid (299 mg).

MS (ISP) 519 [(M+H)$^+$], 536 [(M+NH$_4$)$^+$] and 541 [(M+Na)$^+$]; mp 98° C.

Example O14

[2-[3-(3-Cyano-phenyl)-3-oxo-propionylamino]-5-(1,4-dioxa-8-aza-spiro[4.5]dec-8-yl)-4-phenylethynyl-phenyl]-carbamic acid tert.-butyl ester Prepared from [2-amino-5-(1,4-dioxa-8-aza-spiro[4.5]dec-8-yl)-4-phenylethynyl-phenyl]-carbamic acid tert.-butyl ester (Example L18) (393 mg, 0.87 mmol) and 3-(2,2-dimethyl-6-oxo-6H-[1,3]dioxin-4-yl)-benzonitrile (Example N4) (301 mg, 1.31 mmol) according to the general procedure O. Obtained as an amorphous orange material (268 mg).

MS (ISP) 621 [(M+H)$^+$].

Example O15

[2-[3-(3-Iodo-phenyl)-3-oxo-propionylamino]-5-(2-methoxy-ethoxy)-4-phenylethynyl-phenyl]-carbamic acid tert.-butyl ester Prepared from [2-amino-5-(2-methoxy-ethoxy)-4-phenylethynyl-phenyl]-carbamic acid tert.-butyl ester (Example L11) (840 mg, 2.2 mmol) and 6-(3-iodo-phenyl)-2,2-dimethyl-[1,3]dioxin-4-one (Example N7) (780 mg, 2.36 mmol) according to the general procedure O. Obtained as a white solid (1.3 g).

MS (ISP) 655 [(M+H)$^+$], 672 [(M+NH4)$^+$], 677 [(M+Na)$^+$] and 693 [(M+K)$^+$]; mp 172° C.

Example O16

[2-[3-(3-Cyano-phenyl)-3-oxo-propionylamino]-5-(2,2-dimethyl-[1,3]dioxolan-4-ylmethoxy)-4-phenylethynyl-phenyl]-carbamic acid tert.-butyl ester Prepared from [2-amino-5-(2,2-dimethyl-[1,3]dioxolan-4-ylmethoxy)-4-phenylethynyl-phenyl]-carbamic acid tert.-butyl ester (Example L20) (439 mg, 1.0 mmol) and 3-(2,2-dimethyl-6-oxo-6H-[1,3]dioxin-4-yl)-benzonitrile (Example N4) (345 mg, 1.5 mmol) according to the general procedure O. Obtained as a yellow solid (275 mg).

MS (ISP) 610 [(M+H)$^+$], 627 [(M+NH$_4$)$^+$] and 632 [(M+Na)$^+$]; mp 132–134° C.

Example O17

5-tert.-Butoxycarbonylamino-4-[3-(3-cyano-phenyl)-3-oxo-propionylamino]-2-iodo-benzoic acid methyl ester Prepared from 4-amino-5-tert.-butoxycarbonylamino-2-iodo-benzoic acid methyl ester (Example L21) (395 mg, 1.0 mmol) and 3-(2,2-dimethyl-6-oxo-6H-[1,3]dioxin-4-yl)-benzonitrile (Example N4) (254 mg, 1.1 mmol) according to the general procedure O. Obtained as an apricot solid (435 mg).

MS (ISP) 564 [(M+H)$^+$], 581 [(M+NH$_4$)$^+$] and 586 [(M+Na)$^+$]; mp 162–166° C.

Example O18

[[2-[3-(3-Imidazol-1-yl-phenyl)-3-oxo-propionylamino]-5-(2-methoxy-ethoxy)-4-phenylethynyl-phenyl]-carbamic acid tert.-butyl ester Prepared from [2-amino-5-(2-methoxy-ethoxy)-4-phenylethynyl-phenyl]-carbamic acid tert.-butyl ester (Example L11) (191 mg, 0.5 mmol) and 6-(3-imidazol-1-yl-phenyl)-2,2-dimethyl-[1,3]dioxin-4-one (Example N10) (135 mg, 0.5 mmol) according to the general procedure O. Obtained as a light brown waxy solid (206 mg).

MS (ISN) 593 [(M−H)$^−$]; mp 122–129° C.

Example O19

[RS]-[2-[3-(3-Cyano-phenyl)-3-oxo-propionylamino]-5-(2-oxo-[1,3]dioxolan-4-ylmethoxy)-4-phenylethynyl-phenyl]-carbamic acid tert.-butyl ester Prepared from [RS]-[2-amino-5-(2-oxo-[1,3]dioxolan-4-ylmethoxy)-4-phenylethynyl-phenyl]-carbamic acid tert.-butyl ester (Example L22) (346 mg, 0.82 mmol) and 3-(2,2-dimethyl-6-oxo-6H-[1,3]dioxin-4-yl)-benzonitrile (Example N4) (206 mg, 0.9 mmol) according to the general procedure K. Obtained as a light yellow solid (433 mg).

MS (ISP) 594 [(M−H)$^+$]; mp 181° C.

Example O20

{2-[3-(3-Cyano-phenyl)-3-oxo-propionylamino]-5-ethoxymethyl-4-phenylethynyl-phenyl}-carbamic acid tert.-butyl ester Prepared from (2-amino-5-ethoxymethyl-4-phenylethynyl-phenyl)-carbamic acid tert.-butyl ester (Example L23) (130 mg, 0.35 mmol) and 3-(2,2-dimethyl-6-oxo-6H-[1,3]dioxin-4-yl)-benzonitrile (Example N4) (80 mg, 0.35 mmol) according to the general procedure K. Obtained as an amorphous yellow substance (148 mg).

MS (ISP) 538 [(M−H)$^+$].

Example O21

2,2-Dimethyl-propionic acid 5-tert.-butoxycarbonylamino-4-[3-(3-cyano-phenyl)-3-oxo-propionylamino]-2-phenylethynyl-benzyl ester Prepared from 2,2-dimethyl-propionic acid 4-amino-5-tert.-butoxycarbonylamino-2-phenylethynyl-benzyl ester (Example L24) (155 mg, 0.37 mmol) and 3-(2,2-dimethyl-6-oxo-6H-[1,3]dioxin-4-yl)-benzonitrile (Example N4) (94 mg, 0.41 mmol) according to the general procedure K. Obtained as an amorphous light orange substance (184 mg).

MS (ISP) 611 [(M+NH$_4$)$^+$].

Example O22

(RS)-[2-[3-(3-Imidazol-1-yl-phenyl)-3-oxo-propionylamino]-4-phenylethynyl-5-(tetrahydro-pyran-2-yloxymethyl)-phenyl]-carbamic acid tert.-butyl ester Prepared from (RS)-[2-amino-4-phenylethynyl-5-(tetrahydro-pyran-2-yloxymethyl)-phenyl]-carbamic acid tert.-butyl ester (Example L25) and 6-(3-imidazol-1-yl-phenyl)-2,2-dimethyl-[1,3]dioxin-4-one (Example N10) according to the general procedure O. Obtained as an amorphous yellow substance (267 mg).

MS (ISP) 635 [(M+H)$^+$].

Example O23

[2-[3-(3-Imidazol-1-yl-phenyl)-3-oxo-propionylamino]-5-(4-methoxy-piperidin-1-yl)-4-phenylethynyl-phenyl]-carbamic acid tert.-butyl ester Prepared from [2-amino-5-(4-methoxy-piperidin-1-yl)-4-phenylethynyl-phenyl]-carbamic acid tert.-butyl ester (Example L26) (236 mg, 0.56 mmol) and 6-(3-imidazol-1-yl-phenyl)-2,2-dimethyl-[1,3]dioxin-4-one (Example N10) (151 mg, 0.56 mmol) according to the general procedure O. Obtained as an amorphous yellow substance (253 mg).

MS (ISP) 634 [(M+H)$^+$].

Example O24

[2-[3-(3-Cyano-phenyl)-3-oxo-propionylamino]-5-(4-methoxy-piperidin-1-yl)-4-phenylethynyl-phenyl]-carbamic acid tert.-butyl ester Prepared from [2-amino-5-(4-methoxy-piperidin-1-yl)-4-phenylethynyl-phenyl]-carbamic acid tert.-butyl ester (Example L26) (224 mg, 0.53 mmol) and 3-(2,2-dimethyl-6-oxo-6H-[1,3]dioxin-4-yl)-benzonitrile (Example N4) (125 mg, 0.53 mmol) according to the general procedure O. Obtained as a yellow foam (274 mg).

MS (ISN) 591 [(M−H)$^−$]; mp 97–100° C.

Example O25

{5-Cyanomethoxy-2-[3-(3-imidazol-1-yl-phenyl)-3-oxo-propionylamino]-4-phenylethynyl-phenyl}-carbamic acid tert.-butyl ester Prepared from (2-amino-5-cyanomethoxy-4-phenylethynyl-phenyl)-carbamic acid tert.-butyl ester (Example L27) and 6-(3-imidazol-1-yl-phenyl)-2,2-dimethyl-[1,3]dioxin-4-one (Example N10) according to the general procedure O. Obtained as an amorphous yellow substance (169 mg).

MS (ISP) 576 [(M+H)⁺].

Example O26

{5-Cyanomethoxy-2-[3-(3-cyano-phenyl)-3-oxo-propionylamino]-4-phenylethynyl-phenyl}-carbamic acid tert.-butyl ester Prepared from (2-amino-5-cyanomethoxy-4-phenylethynyl-phenyl)-carbamic acid tert.-butyl ester (Example L27) (80 mg, 0.22 mmol) and 3-(2,2-dimethyl-6-oxo-6H-[1,3]dioxin-4-yl)-benzonitrile (Example N4) (55 mg, 0.24 mmol) according to the general procedure O. Obtained as an amorphous yellow substance (96 mg).

MS (ISN) 533 [(M−H)⁻].

Example O27

(RS)-[4-(4-Fluoro-phenylethynyl)-2-[3-(3-imidazol-1-yl-phenyl)-3-oxo-propionylamino]-5-(tetrahydro-pyran-2-yloxymethyl)-phenyl]-carbamic acid tert.-butyl ester Prepared from (RS)-2-amino-4-(4-fluoro-phenylethynyl)-5-(tetrahydro-pyran-2-yloxymethyl)-phenyl]-carbamic acid tert.-butyl ester (Example L28) and 6-(3-imidazol-1-yl-phenyl)-2,2-dimethyl-[1,3]dioxin-4-one (Example N10) according to the general procedure O. Obtained as an amorphous yellow substance (990 mg).

MS (ISN) 651 [(M−H)⁻].

Example O28

(RS)-(4-(4-Fluoro-phenylethynyl)-2-[3-(3-imidazol-1-yl-phenyl)-3-oxo-propionylamino]-5-{methyl-[2-(tetrahydro-pyran-2-yloxy)-ethyl]-amino}-phenyl)-carbamic acid tert.-butyl ester Prepared from (RS)-(2-amino-4-(4-fluoro-phenylethynyl)-5-{methyl-[2-(tetrahydro-pyran-2-yloxy)-ethyl]-amino}-phenyl)-carbamic acid tert.-butyl ester (Example L29) (242 mg, 0.5 mmol) and 6-(3-imidazol-1-yl-phenyl)-2,2-dimethyl-[1,3]dioxin-4-one (Example N10) (135 mg, 0.5 mmol) according to the general procedure O. Obtained as an amorphous yellow substance (198 mg).

MS (ISN) 694 [(M−H)⁻].

Example O29

{5-(4,4-Diethoxy-piperidin-1-yl)-2-[3-(3-imidazol-1-yl-phenyl)-3-oxo-propionylamino]-4-phenylethynyl-phenyl}-carbamic acid tert.-butyl ester Prepared from [2-amino-5-(4,4-diethoxy-piperidin-1-yl)-4-phenylethynyl-phenyl]-carbamic acid tert.-butyl ester (Example L18) (321 mg, 0.67 mmol) and 6-(3-imidazol-1-yl-phenyl)-2,2-dimethyl-[1,3]dioxin-4-one (Example N10) (240 mg, 0.89 mmol) according to the general procedure O. Obtained as an orange foam (295 mg).

MS (ISP) 692 [(M+H)⁺].

Example O30

(RS)-{2-[3-(3-Imidazol-1-yl-phenyl)-3-oxo-propionylamino]-4-phenylethynyl-5-[2-(tetrahydro-pyran-2-yloxy)-ethoxy]-phenyl}-carbamic acid tert.-butyl ester Prepared from (RS)-{2-amino-4-phenylethynyl-5-[2-(tetrahydro-pyran-2-yloxy)-ethoxy]-phenyl}-carbamic acid tert.-butyl ester (Example L30) (346 mg, 0.76 mmol) and 6-(3-imidazol-1-yl-phenyl)-2,2-dimethyl-[1,3]dioxin-4-one (Example N10) (300 mg, 1.11 mmol) according to the general procedure O. Obtained as a yellow foam (196 mg).

MS (ISP) 665 [(M+H)⁺].

Example O31

(RS)-{4'-Fluoro-5-[3-(3-imidazol-1-yl-phenyl)-3-oxo-propionylamino]-2-[4-(tetrahydro-pyran-2-yloxy)-piperidin-1-yl]-biphenyl-4-yl}-carbamic acid tert.-butyl ester Prepared from (RS)-[2-amino-4-(4-fluoro-phenylethynyl)-5-(tetrahydro-pyran-2-yloxymethyl)-phenyl]-carbamic acid tert.-butyl ester (Example L28) and 6-(3-imidazol-1-yl-phenyl)-2,2-dimethyl-[1,3]dioxin-4-one (Example N10) according to the general procedure O. Obtained as a yellow solid (282 mg).

MS (ISP) 698 [(M+H)⁺]; mp 129–132° C.

Example O32

{5-(2-tert.-Butoxy-ethoxy)-4-(4-fluoro-phenylethynyl)-2-[3-(3-imidazol-1-yl-phenyl)-3-oxo-propionylamino]-phenyl}-carbamic acid tert.-butyl ester Prepared from [2-amino-5-(2-tert.-butoxy-ethoxy)-4-(4-fluoro-phenylethynyl)-phenyl]-carbamic acid tert.-butyl ester (Example L32) (560 mg, 1.27 mmol) and 6-(3-imidazol-1-yl-phenyl)-2,2-dimethyl-[1,3]dioxin-4-one (Example N10O) (413 mg, 1.53 mmol) according to the general procedure O. Obtained as a yellow solid (507 mg).

MS (ISP) 655 [(M+H)⁺]; mp 62–65° C.

Example O33

(RS)-(4'-Fluoro-5-[3-(3-imidazol-1-yl-phenyl)-3-oxo-propionylamino]-2-{4-[2-(tetrahydro-pyran-2-yloxy)-ethoxy]-piperidin-1-yl}-biphenyl-4-yl)-carbamic acid tert.-butyl ester Prepared from (RS)-(5-amino-4'-fluoro-2-{4-[2-(tetrahydro-pyran-2-yloxy)-ethoxy]-piperidin-1-yl}-biphenyl-4-yl)-carbamic acid tert.-butyl ester (Example L33) and 6-(3-imidazol-1-yl-phenyl)-2,2-dimethyl-[1,3]dioxin-4-one (Example N10) according to the general procedure O. Obtained as a yellow solid (473 mg).

MS (ISP) 742 [(M+H)⁺]; mp 57–58° C.

Example O34

(RS)-[4'-Fluoro-5-[3-(3-imidazol-1-yl-phenyl)-3-oxo-propionylamino]-2-(tetrahydro-pyran-2-yloxymethyl)-biphenyl-4-yl]-carbamic acid tert.-butyl ester Prepared from (RS)-[5-amino-4'-fluoro-2-(tetrahydro-pyran-2-yloxymethyl)-biphenyl-4-yl]-carbamic acid tert-butyl ester (Example L34) and 6-(3-imidazol-1-yl-phenyl)-2,2-dimethyl-[1,3]dioxin-4-one (Example N10) according to the general procedure O. Obtained as a light yellow solid (330 mg).

Example O35

{2-Cyanomethoxy-4'-fluoro-5-[3-(3-imidazol-1-yl-phenyl)-3-oxo-propionylamino]-biphenyl-4-yl}-carbamic acid tert.-butyl ester Prepared from (5-amino-2-cyanomethoxy-4'-fluoro-biphenyl-4-yl)-carbamic acid tert.-butyl ester (Example L35) (190 mg, 0.53 mmol) and 6-(3-imidazol-1-yl-phenyl)-2,2-dimethyl-[1,3]dioxin-4-one (Example N10) (164 mg, 0.61 mmol) according to the general procedure O. Obtained as a yellow gum (90 mg).

MS (ISP) 570 [(M+H)$^+$].

Example O36

{2-Dimethylaminomethyl-4'-fluoro-5-[3-(3-imidazol-1-yl-phenyl)-3-oxo-propionylamino]-biphenyl-4-yl}-carbamic acid tert.-butyl ester Prepared from (5-amino-2-dimethylaminomethyl-4'-fluoro-biphenyl-4-yl)-carbamic acid tert.-butyl ester (Example L36) and 6-(3-imidazol-1-yl-phenyl)-2,2-dimethyl-[1,3]dioxin-4-one (Example N10) according to the general procedure O. Obtained as a light yellow solid (329 mg).

Example O37

{2-(2,2-Dimethyl-tetrahydro-[1,3]dioxolo[4,5-c]pyrrol-5-yl)-4'-fluoro-5-[3-(3-imidazol-1yl-phenyl)-3-oxo-propionylamino]-biphenyl-4-yl}-carbamic acid tert.-butyl ester Prepared from [5-amino-2-(2,2-dimethyl-tetrahydro-[1,3]dioxolo [4,5-c]pyrrol-5-yl)-4'-fluoro-biphenyl-4-yl]-carbamic acid tert.-butyl ester (Example L37) (465 mg, 1.05 mmol) and 6-(3-imidazol-1-yl-phenyl)-2,2-dimethyl-[1,3]dioxin-4-one (Example N10) (314 mg, 1.16 mmol) according to the general procedure O. Obtained as an amorphous yellow substance (540 mg).

MS (ISN) 654 [(M−H)$^−$].

Example O38

{4'-Fluoro-5-[3-(3-imidazol-1-yl-phenyl)-3-oxo-propionylamino]-2-methoxy-biphenyl-4-yl}-carbamic acid tert.-butyl ester Prepared from (5-amino-4'-fluoro-2-methoxy-biphenyl-4-yl)-carbamic acid tert.-butyl ester (Example L38) (332 mg, 1.0 mmol) and 6-(3-imidazol-1-yl-phenyl)-2,2-dimethyl-[1,3]dioxin-4-one (Example N10) (270 mg, 1.0 mmol) according to the general procedure O. Obtained as an amorphous brown substance (328 mg).

MS (ISN) 543 [(M−H)$^−$].

Example O39

{2-(1,4-Dioxa-8-aza-spiro[4.5]dec-8-yl)-4'-fluoro-5-[3-(3-Imidazol-1yl-phenyl)-3oxo-propionylamino]-biphenyl-4-yl}-carbamic acid tert.-butyl ester Prepared from [5-amino-2-(1,4-dioxa-8-aza-spiro[4.5]dec-8-yl)-4'-fluoro-biphenyl-4-yl]-carbamic acid tert.-butyl ester (Example L39) (444 mg, 1.0 mmol) and 6-(3-imidazol-1-yl-phenyl)-2,2-dimethyl-[1,3]dioxin-4-one (Example N10) (321 mg, 1.19 mmol) according to the general procedure O. Obtained as a brown solid (457 mg).

MS (ISN) 654 [(M−H)$^−$]; mp 110–115° C. (dec.).

Example O40

{4'-Fluoro-5-[3-(3-imidazol-1-yl-phenyl)-3-oxo-propionylamino]-2-methyl-biphenyl-4yl}-carbamic acid tert.-butyl ester Prepared from (5-amino-4'-fluoro-2-methyl-biphenyl-4-yl)-carbamic acid tert.-butyl ester (Example L40) (316 mg, 1.0 mmol) and 6-(3-imidazol-1-yl-phenyl)-2,2-dimethyl-[1,3]dioxin-4-one (Example N10) (297 mg, 1.1 mmol) according to the general procedure O. Obtained as an amorphous yellow substance (361 mg).

MS (ISP) 529 [(M+H)$^+$].

Example O41

{4-tert.-Butoxycarbonylamino-4'-fluoro-5-[3-(3-imidazol-1-yl-phenyl)-3-oxo-propionylamino]-biphenyl-2-yloxy}-acetic acid tert.-butyl ester Prepared from (5-amino-4-tert.-butoxycarbonylamino-4'-fluoro-biphenyl-2-yloxy)-acetic acid tert.-butyl ester (Example L41) (1.4 g, 3.24 mmol) and 6-(3-imidazol-1-yl-phenyl)-2,2-dimethyl-[1,3]dioxin-4-one (Example N10) (885 mg, 3.27 mmol) according to the general procedure O. Obtained as a light brown solid (759 mg).

MS (ISP) 645 [(M+H)$^+$]; mp 82–85° C.

Example O42

{2-Chloro-4'-fluoro-5-[3-(3-imidazol-1-yl-phenyl)-3-oxo-propionylamino]-biphenyl-4yl}-carbamic acid tert.-butyl ester Prepared from (5-amino-2-chloro-4'-fluoro-biphenyl-4-yl)-carbamic acid tert.-butyl ester (Example L42) (168 mg, 0.5 mmol) and 6-(3-imidazol-1-yl-phenyl)-2,2-dimethyl-[1,3]dioxin-4-one (Example N10) (252 mg, 0.93 mmol) according to the general procedure O. Obtained as a light yellow solid (156 mg).

MS (ISN) 547 [(M−H)$^−$].

Example O43

[4'-Fluoro-5-[3-(3-imidazol-1-yl-phenyl)-3-oxo-propionylamino]-2-(2-methoxy-ethoxy)-biphenyl-4-yl]-carbamic acid tert.-butyl ester Prepared from [5-amino-4'-fluoro-2-(2-methoxy-ethoxy)-biphenyl-4-yl]-carbamic acid tert.-butyl ester (Example L43) (188 mg, 0.5 mmol) and 6-(3-imidazol-1-yl-phenyl)-2,2-dimethyl-[1,3]dioxin-4-one (Example N10) (260 mg, 0.96 mmol) according to the general procedure O. Obtained as an orange solid (218 mg).

MS ([SP) 589 [(M+H)$^+$]; mp 61–63° C.

Example O44

{2-(2-tert.-Butoxy-ethoxy)-4'-fluoro-5-[3-(3-imidazol-1-yl-phenyl)-3-oxo-propionylamino]-biphenyl-4-yl}-carbamic acid tert.-butyl ester Prepared from [5-amino-2-(2-tert.-butoxy-ethoxy)-4'-fluoro-biphenyl-4-yl]-carbamic acid tert.-butyl ester (Example L44) (209 mg, 0.5 mmol) and 6-(3-imidazol-1-yl-phenyl)-2,2-dimethyl-[1,3]dioxin-4-one (Example N10) (135 mg, 0.5 mmol) according to the general procedure O. Obtained as a beige solid (194 mg).

MS (ISP) 631 [(M+H)$^+$]; mp 101° C.

Example O45

[4'-Fluoro-5-[3-(3-imidazol-1-yl-phenyl)-3-oxo-propionylamino]-2-(2-oxo-oxazolidin-3yl)-biphenyl-4-yl]-carbamic acid tert.-butyl ester Prepared from [5-amino-4'-fluoro-2-(2-oxo-oxazolidin-3-yl)-biphenyl-4-yl]-carbamic acid tert.-butyl ester (Example L45) (130 mg, 0.34 mmol) and 6-(3-imidazol-1-yl-phenyl)-2,2-dimethyl-[1,3]dioxin-4-one (Example N10) (92 mg, 0.34 mmol) according to the general procedure O. Obtained as an amorphous yellow substance (86 mg).

MS (ISP) 600 [(M+H)$^+$].

Example O46

{4'-Fluoro-5-[3-(3-imidazol-1-yl-phenyl)-3-oxo-propionylamino]-2-methoxy-2'-methyl-biphenyl-4-yl}-carbamic acid tert.-butyl ester Prepared from (5-amino-4'-fluoro-2-methoxy-2'-methyl-biphenyl-4-yl)-carbamic acid tert.-butyl ester (Example L46) (173 mg, 0.5 mmol) and 6-(3-imidazol-1-yl-phenyl)-2,2-dimethyl-[1,3]dioxin-4-one (Example N10) (199 mg, 1.47 mmol) according to the general procedure O. Obtained as an orange solid (182 mg).

MS (ISP) 559 [(M+H)$^+$]; mp 99–102° C.

Example O47

{2-tert.-Butoxy-4'-fluoro-5-(3-(3-imidazol-1-yl-phenyl[-3-oxo-propionylamino]-biphenyl-4-yl}-carbamic acid tert.-butyl ester Prepared from (5-amino-2-tert.-butoxy-4'-fluoro-biphenyl-4-yl)-carbamic acid tert.-butyl ester (Example L47) (187 mg, 0.5 mmol) and 6-(3-imidazol-1-yl-phenyl)-2,2-dimethyl-[1,3]dioxin-4-one (Example N10) (135 mg, 0.5 mmol) according to the general procedure O. Obtained as an amorphous yellow substance (237 mg).

MS (ISN) 585 [(M–H)$^-$].

Example O48

{2-tert.-Butoxy-2'-fluoro-5-[3-(3-imidazol-1-yl-phenyl)-3-oxo-propionylamino]-biphenyl-4-yl}-carbamic acid tert.-butyl ester Prepared from (5-amino-2-tert.-butoxy-2'-fluoro-biphenyl-4-yl)-carbamic acid tert.-butyl ester (Example L48) (187 mg,0.5 mmol) and 6-(3-imidazol-1-yl-phenyl)-2,2-dimethyl-[1,3]dioxin-4-one (Example N10) (135 mg, 0.5 mmol) according to the general procedure O. Obtained as an amorphous yellow substance (234 mg).

MS (ISN) 585 [(M–H)$^-$].

Example O49

(RS)-{4'-Fluoro-5-[3-(3-imidazol-1-yl-phenyl)-3-oxo-propionylamino]-2-[(R)-3-(tetrahydro-pyran-2-yloxy)-pyrrolidin-1-yl]-biphenyl-4-yl}-carbamic acid tert.-butyl ester Prepared from (RS)-{5-amino-4'-fluoro-2-[(R)-3-(tetrahydro-pyran-2-yloxy)-pyrrolidin-1-yl]-biphenyl-4-yl}-carbamic acid tert.-butyl ester (Example L49) (236 mg, 0.5 mmol) and 6-(3-imidazol-1-yl-phenyl)-2,2-dimethyl-[1,3]dioxin-4-one (Example N 10) (200 mg, 0.74 mmol) according to the general procedure O. Obtained as an orange solid (188 mg).

MS (ISP) 684 [(M+H)$^+$]; mp 99–103° C.

Example O50

{2'-Fluoro-5-[3-(3-imidazol-1-yl-phenyl)-3-oxo-propionylamino]-2-methoxy-biphenyl-4-yl}-carbamic acid tert.-butyl ester Prepared from (5-amino-2'-fluoro-2-methoxy-biphenyl-4-yl)-carbamic acid tert.-butyl ester (Example L50) (159 mg, 0.5 mmol) and 6-(3-imidazol-1-yl-phenyl)-2,2-dimethyl-[1,3]dioxin-4-one (Example N10) (135 mg, 0.5 mmol) according to the general procedure O. Obtained as an amorphous yellow substance (199 mg).

MS (ISN) 543 [(M–H)$^-$].

Example O51

{2-tert.-Butoxy-5-[3-(3-cyano-phenyl)-3-oxo-propionylamino]4'-fluoro-biphenyl-4-yl}-carbamic acid tert.-butyl ester Prepared from (5-amino-2-tert.-butoxy-4'-fluoro-biphenyl-4-yl)-carbamic acid tert.-butyl ester (Example L47) (187 mg, 0.5 mmol) and 3-(2,2-dimethyl-6-oxo-6H-[1,3]dioxin-4-yl)-benzonitrile (Example N4) (126 mg, 0.55 mmol) according to the general procedure O. Obtained as an amorphous light pink substance (196 mg).

MS (ISP) 546 [(M+H)$^+$].

Example O52

{2-tert.-Butoxy-5-[3-(3-cyano-phenyl)-3-oxo-propionylamino]-2'-fluoro-biphenyl-4-yl}-carbamic acid tert.-butyl ester Prepared from (5-amino-2-tert.-butoxy-2'-fluoro-biphenyl-4-yl)-carbamic acid tert.-butyl ester (Example L48) (187 mg, 0.5 mmol) and 3-(2,2-dimethyl-6-oxo-6H-[1,3]dioxin-4-yl)-benzonitrile (Example N4) (126 mg, 0.55 mmol) according to the general procedure O. Obtained as an amorphous light pink substance (197 mg).

MS (ISP) 546 [(M+H)$^+$].

Example O53

{5-[3-(3-Cyano-phenyl)-3-oxo-propionylamino]-2'-fluoro-2-methoxy-biphenyl-4-yl}-carbamic acid tert.-butyl ester Prepared from (5-amino-2'-fluoro-2-methoxy-biphenyl-4-yl)-carbamic acid tert.-butyl ester (Example L50) (112 mg, 0.35 mmol) and 3-(2,2-dimethyl-6-oxo-6H-[1,3]dioxin-4-yl)-benzonitrile (Example N4) (80 mg, 0.35 mmol) according to the general procedure O. Obtained as a yellow foam (131 mg).

MS (ISN) 502 [(M–H)$^-$].

Example O54

(2'-Fluoro-2-methoxy-5-{3-[3-(2-methyl-imidazol-1-yl)-phenyl]-3-oxo-propionylamino}-biphenyl-4-yl)-carbamic acid tert.-butyl ester Prepared from (5-amino-2'-fluoro-2-methoxy-biphenyl-4-yl)-carbamic acid tert.-butyl ester (Example L50) (249 mg, 0.75 mmol) and 3-[3-(2-methyl-imidazol-1-yl)-phenyl]-3-oxo-propionic acid tert.-butyl ester (Example M8) (275 mg, 0.92 mmol) according to the general procedure O. Obtained as a yellow solid (312 mg).

MS (ISP) 559 [(M+H)$^+$]; mp 83–86° C.

Example O55

{5-[3-(5-Cyano-thiophen-2-yl)-3-oxo-propionylamino]-2'-fluoro-2-methoxy-biphenyl-4-yl}-carbamic acid tert.-butyl ester Prepared from (5-amino-2'-fluoro-2-methoxy-biphenyl-4-yl)-carbamic acid tert.-butyl ester (Example L50) (166 mg, 0.5 mmol) 3-(5-cyano-thiophen-2-yl)-3-oxo-propionic acid tert.-butyl ester (Example M17) (138 mg, 0.55 mmol) according to the general procedure O. Obtained as a light yellow solid (244 mg).

MS (ISP) 510 [(M+H)$^+$]; mp 200° C. (dec.).

Example O56

{2'-Fluoro-2-methoxy-5-[3-oxo-3-(3-[1,2,4]triazol-4-yl-phenyl)-propionylamino]-biphenyl-4-yl}-carbamic acid tert.-butyl ester Prepared from (5-amino-2'-fluoro-2-methoxy-biphenyl-4-yl)-carbamic acid tert.-butyl ester (Example L50) (166 mg, 0.5 mmol) and 3-oxo-3-(3-[1,2,4]triazol-4-yl-phenyl)-propionic acid ethyl ester (Example M1) (260 mg, 1.0 mmol) according to the general procedure O. Obtained as a yellow gum (70 mg).

MS (ISP) 546 [(M+H)$^+$].

Example O57

{5-[3-(2-Cyano-pyridin-4-yl)-3-oxo-propionylamino]-2'-fluoro-2-methoxy-biphenyl-4-yl}-carbamic acid tert.-butyl ester Prepared from (5-amino-2'-fluoro-2-methoxy-biphenyl-4-yl)-carbamic acid tert.-butyl ester (Example L50) and 3-(2-cyano-pyridin-4-yl)-3-oxo-propionic acid tert.-butyl ester (Example M10) according to the general procedure O. Obtained as a light yellow solid (189 mg).

MS (ISP) 522 [(M+NH$_4$)$^+$].

Example O58

(2-tert.-Butoxy-4'-fluoro-5-{3-[3-(2-methyl-imidazol-1-yl)-phenyl]-3-oxo-propionylamino}-biphenyl-4-yl)-carbamic acid tert.-butyl ester Prepared from (5-amino-2-tert.-butoxy-4'-fluoro-biphenyl-4-yl)-carbamic acid tert.-butyl ester (Example L47) (140 mg, 0.37 mmol) and 3-[3-(2-methyl-imidazol-1-yl)-phenyl]-3-oxo-propionic acid tert.-butyl ester (Example M8) (111 mg, 0.37 mmol) according to the general procedure O. Obtained as an amorphous yellow substance (139 mg).

MS (ISP) 601 [(M+H)$^+$].

Example O59

{5-[3-(5-Cyano-2-fluoro-phenyl)-3-oxo-propionylamino]-2'-fluoro-2-methoxy-biphenyl-4-yl}-carbamic acid tert.-butyl ester Prepared from (5-amino-2'-fluoro-2-methoxy-biphenyl-4-yl)-carbamic acid tert.-butyl ester (Example L50) (166 mg, 0.5 mmol) and 3-(5-cyano-2-fluoro-phenyl)-3-oxo-propionic acid ethyl ester (Example M18) (141 mg, 0.6 mmol) according to the general procedure O. Obtained as an amorphous yellow substance (165 mg).

MS (ISP) 522 [(M+H)$^+$].

Example O60

{2-tert.-Butoxy-5-[3-(2-cyano-pyridin-4-yl)-3-oxo-propionylamino]-4'-fluoro-biphenyl-4-yl}-carbamic acid tert.-butyl ester Prepared from (5-amino-2-tert.-butoxy-4'-fluoro-biphenyl-4-yl)-carbamic acid tert.-butyl ester (Example L47) (140 mg, 0.37 mmol) and 3-(2-cyano-pyridin-4-yl)-3-oxo-propionic acid tert.-butyl ester (Example M10) (91 mg, 0.37 mmol) according to the general procedure O. Obtained as an amorphous yellow substance (164 mg).

MS (ISP) 547 [(M+H)$^+$].

Example O61

{2-tert.-Butoxy-2'-fluoro-5-[3-oxo-3-(3-[1,2,3]triazol-1-yl-phenyl)-propionylamino]-biphenyl-4-yl}-carbamic acid tert.-butyl ester Prepared from (5-amino-2-tert.-butoxy-2'-fluoro-biphenyl-4-yl)-carbamic acid tert.-butyl ester (Example L48) (187 mg, 0.5 mmol) and 3-oxo-3-(3-[1,2,3]triazol-1-yl-phenyl)-propionic acid ethyl ester (Example M2) (180 mg, 0.69 mmol) according to the general procedure O. Obtained as a light yellow solid (257 mg).

MS (ISP) 588 [(M+H)$^+$]; mp 47–50° C.

Example O62

[5-[3-(3-Cyano-phenyl)-3-oxo-propionylamino]-2-(1,4-dioxa-8-aza-spiro[4.5]dec-8-yl)-2'-fluoro-biphenyl-4-yl]-carbamic acid tert.-butyl ester Prepared from [5-amino-2-(1,4-dioxa-8-aza-spiro[4.5]dec-8-yl)-2'-fluoro-biphenyl-4-yl]-carbamic acid tert.-butyl ester (Example L51) (222 mg, 0.5 mmol) and 3-(3-cyano-phenyl)-3-oxo-propionic acid tert.-butyl ester (Example M3) (182 mg, 0.8 mmol) according to the general procedure O. Obtained as an amorphous yellow substance (258 mg).

MS (ISP) 615 [(M+H)$^+$].

Example O63

{2-(1,4-Dioxa-8-aza-spiro[4.5]dec-8-yl)-2'-fluoro-5-[3-(3-imidazol-1-yl-phenyl)-3-oxo-propionylamino]-biphenyl-4-yl}-carbamic acid tert.-butyl ester Prepared from [5-amino-2-(1,4-dioxa-8-aza-spiro[4.5]dec-8-yl)-2'-fluoro-biphenyl-4-yl]-carbamic acid tert.-butyl ester (Example L51) (222 mg, 0.5 mmol) and 6-(3-imidazol-1-yl-phenyl)-2,2-dimethyl-[1,3]dioxin-4-one (Example N10) (135 mg, 0.5 mmol) according to the general procedure O. Obtained as an amorphous yellow substance (294 mg).

MS (ISP) 656 [(M+H)$^+$].

Example O64

(2-tert.-Butoxy-2'-fluoro-5-{3-[3-(2-methyl-imidazol-1-yl)-phenyl]-3-oxo-propionylamino}-biphenyl-4-yl)-carbamic acid tert.-butyl ester Prepared from (5-amino-2-tert.-butoxy-2'-fluoro-biphenyl-4-yl)-carbamic acid tert.-butyl ester (Example L48) (187 mg, 0.5 mmol) and 2,2-dimethyl-6-[3-(2-methyl-imidazol-1-yl)-phenyl]-[1,3]dioxin-4-one (Example N15) (142 mg, 0.5 mmol) according to the general procedure O. Obtained as an amorphous yellow substance (234 mg).

MS (ISP) 601 [(M+H)$^+$].

Example O65

{2-tert.-Butoxy-5-[3-(2-cyano-pyridin-4-yl)-3-oxo-propionylamino]-2'-fluoro-biphenyl-4-yl}-carbamic acid tert.-butyl ester Prepared from (5-amino-2-tert.-butoxy-2'-fluoro-biphenyl-4-yl)-carbamic acid tert.-butyl ester (Example L48) (187 mg, 0.5 mmol) and 4-(2,2-dimethyl-6-oxo-6H-[1,3]dioxin-4-yl) -pyridine-2-carbonitrile (Example N16) (115 mg, 0.5 mmol) according to the general procedure O. Obtained as an amorphous yellow substance (216 mg).

MS (ISP) 547 [(M+H)$^+$].

Example O66

(2-tert.-Butoxy-2'-fluoro-5-{3-[3-(2-methylsulfanyl-imidazol-1-yl)-phenyl]-3-oxo-propionylamino}-biphenyl-4-yl)-carbamic acid tert.-butyl ester Prepared from (5-amino-2-tert.-butoxy-2'-fluoro-biphenyl-4-yl)-carbamic acid tert.-butyl ester (Example L48) (187 mg, 0.5 mmol) and 3-[3-(2-methylsulfanyl-imidazol-1-yl)-phenyl]-3-oxo-propionic acid tert.-butyl ester (Example M13) (211 mg, 0.63 mmol) according to the general procedure O. Obtained as a light yellow solid (260 mg).

MS (ISN) 631 [(M−H)$^−$]; mp 59–62° C.

Example O67

{5-[3-(3-Cyano-phenyl)-3-oxo-propionylamino]-2',5'-difluoro-2-methoxy-biphenyl-4-yl}-carbamic acid tert.-butyl ester Prepared from (5-amino-2',5'-difluoro-2-methoxy-biphenyl-4-yl)-carbamic acid tert.-butyl ester (Example L52) (175 mg, 0.5 mmol) and 3-(2,2-dimethyl-6-oxo-6H-[1,3]dioxin-4-yl)-benzonitrile (Example N4) (115 mg, 0.5 mmol) according to the general procedure O. Obtained as an amorphous yellow substance (136 mg).

MS (ISP) 522 [(M+H)$^+$].

Example O68

{2',5'-Difluoro-2-methoxy-5-[3-oxo-3-(3-[1,2,3]triazol-1-yl-phenyl)-propionylamino]-biphenyl-4-yl}-carbamic acid tert.-butyl ester Prepared from (5-amino-2',5'-difluoro-2-methoxy-biphenyl-4-yl)-carbamic acid tert.-butyl ester (Example L52) (175 mg, 0.5 mmol) and 3-oxo-3-(3-[1,2,3]triazol-1-yl-phenyl)-propionic acid ethyl ester (Example M2) (130 mg, 0.5 mmol) according to the general procedure O. Obtained as an amorphous light yellow substance (185 mg).

MS (ISN) 562 [(M−H)$^−$].

Example O69

{2-tert.-Butoxy-5-[3-(3-cyano-thiophen-2-yl)-3-oxo-propionylamino]-2'-fluoro-biphenyl-4-yl}-carbamic acid tert.-butyl ester Prepared from (5-amino-2-tert.-butoxy-2'-fluoro-biphenyl-4-yl)-carbamic acid tert.-butyl ester (Example L48) (187 mg, 0.5 mmol) and 6-(3-cyano-thiophen-2-yl)-2,2-dimethyl-[1,3]dioxin-4-one (Example N3) (130 mg, 0.55 mmol) according to the general procedure O. Obtained as a yellow oil (278 mg).

MS (ISN) 550 [(M−H)$^−$].

Example O70

{2-tert.-Butoxy-5-[3-(5-cyano-thiophen-2-yl)-3-oxo-propionylamino]-2'-fluoro-biphenyl-4-yl}-carbamic acid tert.-butyl ester Prepared from (5-amino-2-tert.-butoxy-2'-fluoro-biphenyl-4-yl)-carbamic acid tert.-butyl ester (Example L48) (187 mg, 0.5 mmol) 3-(5-cyano-thiophen-2-yl)-3-oxo-propionic acid tert.-butyl ester (Example M17) (138 mg, 0.55 mmol) according to the general procedure O. Obtained as an amorphous yellow substance (268 mg).

MS (ISN) 550 [(M−H)$^−$].

Example O71

{2-tert.-Butoxy-4'-fluoro-5-[3-oxo-3-(3-[1,2,3]triazol-1-yl-phenyl)-propionylamino]-biphenyl-4-yl}-carbamic acid tert.-butyl ester Prepared from (5-amino-2-tert.-butoxy-4'-fluoro-biphenyl-4-yl)-carbamic acid tert.-butyl ester (Example L47) (187 mg, 0.5 mmol) and 3-oxo-3-(3-[1,2,3]triazol-1-yl-phenyl)-propionic acid ethyl ester (Example M2) (156 mg, 0.6 mmol) according to the general procedure O. Obtained as a yellow gum (198 mg).

MS (ISP) 588 [(M+H)$^+$].

Example O72

[5-[3-(3-Cyano-phenyl)-3-oxo-propionylamino]-2'-fluoro-2-(2-methoxy-ethoxy)-biphenyl-4-yl]-carbamic acid tert.-butyl ester Prepared from [5-amino-2'-fluoro-2-(2-methoxy-ethoxy)-biphenyl-4-yl]-carbamic acid tert.-butyl ester (Example L53) and 3-(2,2-dimethyl-6-oxo-6H-[1,3]dioxin-4-yl)-benzonitrile (Example N4) according to the general procedure O. Obtained as a yellow solid (188 mg).

MS (ISP) 548 [(M+H)$^+$].

Example O73

(RS)-[5-[3-(3-Cyano-phenyl)-3-oxo-propionylamino]-2'-fluoro-2-(tetrahydro-pyran-2-yloxymethyl)-biphenyl-4-yl]-carbamic acid tert.-butyl ester Prepared from (RS)-[5-amino-2'-fluoro-2-(tetrahydro-pyran-2-yloxymethyl)-biphenyl-4-yl]-carbamic acid tert.-butyl ester (Example L54) and 3-(2,2-dimethyl-6-oxo-6H-[1,3]dioxin-4-yl)-benzonitrile (Example N4) according to the general procedure O. Obtained as a yellow solid (155 mg).

MS (ISP) 548 [(M+NH$_4$)$^+$].

Example O74

(2'-Fluoro-2-(4-methoxy-benzyloxy)-5-{3-[3-(3-methyl-isoxazol-5-yl)-phenyl]3-oxo-propionylamino}-biphenyl-4-yl)-carbamic acid tert.-butyl ester Prepared [5-amino-2'-fluoro-2-(4-methoxy-benzyloxy)-biphenyl-4-yl-carbamic acid tert.-butyl ester (Example L55) (438 mg, 1.0 mmol) and 3-[3-(3-methyl-isoxazol-5-yl)-phenyl]-3-oxo-propionic acid tert.-butyl ester (Example M14) (301 mg, 1.0 mmol) according to the general procedure O. Obtained as an amorphous light yellow substance (561 mg).

MS (ISP) 666 [(M+H)$^+$].

Example O75

{2-tert.-Butoxy-5-[3-(3-cyano-phenyl)-3-oxo-propionylamino]-2',5'-difluoro-biphenyl-4-yl}-carbamic acid tert.-butyl ester Prepared from (5-amino-2-tert.-butoxy-2',5'-difluoro-biphenyl-4-yl)-carbamic acid tert.-butyl ester (Example L56) (196 mg, 0.5 mmol) and 3-(2,2-dimethyl-6-oxo-6H-[1,3]dioxin-4-yl)-benzonitrile (Example N4) (115 mg, 0.5 mmol) according to the general procedure O. Obtained as an amorphous beige substance (155 mg).

MS (ISP) 564 [(M+H)$^+$].

Example O76

{5-tert.-Butoxy-4-(4-fluoro-phenylethynyl)-2-[3-(3-imidazol-1-yl-phenyl)-3-oxo-propionylamino]-phenyl}-carbamic acid tert.-butyl ester Prepared from [2-amino-5-tert.-butoxy-4-(4-fluoro-phenylethynyl)-phenyl]-carbamic acid tert.-butyl ester (Example L57) (160 mg, 0.4 mmol) and 3-(3-imidazol-1-yl-phenyl)-3-oxo-propionic acid tert.-butyl ester (Example M4) (115 mg, 0.4 mmol) according to the general procedure O. Obtained as an amorphous yellow substance (140 mg).

MS (ISP) 611 [(M+H)$^+$].

Example O77

{5-tert.-Butoxy-4-(4-fluoro-phenylethynyl)-2-[3-oxo-3-(3-[1,2,3]triazol-1-yl-phenyl)-propionylamino]-phenyl}-carbamic acid tert.-butyl ester Prepared from [2-amino-5-tert.-butoxy-4-(4-fluoro-phenylethynyl)-phenyl]-carbamic acid tert.-butyl ester (Example L57) (160 mg, 0.4 mmol) and 3-oxo-3-(3-[1,2,3]triazol-1-yl-phenyl)-propionic acid ethyl ester (Example M2) (104 mg, 0.4 mmol) according to the general procedure O. Obtained as a yellow gum (150 mg).

MS (ISP) 612 [(M+H)$^+$].

General Procedure P

Preparation of 4,8-diaryl-1,3-dihydro-benzo[b][1,4]diazepin-2-ones, 4-aryl-8-aroyl-1,3-dihydro-benzo[b][1,4]diazepin-2-ones or 4-aryl-8-arylethynyl-1,3-dihydro-benzo[b][1,4]diazepin-2-ones A suspension of the {2-[3-aryl-3-oxo-propionylamino]-4-aryl-phenyl}-carbamic acid tert-butyl ester or {2-[3-aryl-3-oxo-propionylamino]-4-arylethynyl-phenyl}-carbamic acid tert-butyl ester (1.0 mmol) in $CH_2Cl_2$ (5 mL) [anisole or 1,3-dimethoxybenzene (5–15 mmol) can be added if necessary] was treated with TFA (0.5–5.0 mL) at 0° C. and stirring was continued at 23° C. until tlc indicated complete consumption of the starting material. The solvent was removed in vacuum, the residue treated with little ether, whereupon it crystallized. The solid was stirred with sat. $NaHCO_3$-sol., filtered, washed with $H_2O$ and ether or mixtures of ether/hexane and was dried to give the title compound, which if necessary can be purified by crystallization from $THF/CH_2Cl_2$/ether/hexane.

General Procedure Q

Preparation of 4-[3-(Amino-4-carbonyl)-phenyl]-8-phenylethynyl-1,3-dihydro-benzo[b][1,4]diazepin-2-ones by Pd-catalyzed carbonylative amination of 4-(3-iodophenyl)-8-phenylethynyl-1,3-dihydro-benzo[b][1,4]diazepin-2-one A solution of the 4-(3-iodophenyl)-8-phenylethynyl-1,3-dihydro-benzo[b][1,4]diazepin-2-one (1.0 mmol), the secondary amine (5.0 mmol), $PPh_3$ (6 mol %) or dppp (3 mol %), $Pd(OAc)_2$ (3 mol %) and $Et_3N$ (2.0 mmol) in DMF (4 mL) was stirred at 23° C. under CO-atmosphere until tlc indicated complete consumption of the iodide. After dilution with EtOAc, washing with sat. $NaHCO_3$-sol. and brine, the organic phase was dried over $Na_2SO_4$. Removal of the solvent left a brown oil, which was purified by silica gel column chromatography with hexane/EtOAc to give the title compound.

General Procedure R

Preparation of (5-hydroxy-2-nitro-phenyl)-carbamic acid tert.-butyl esters by Rh-catalyzed deallylation of (5-allyloxy-2-nitro-phenyl)-carbamic acid tert.-butyl esters A mixture of the (5-allyloxy-2-nitro-phenyl)-carbamic acid tert.-butyl ester, $(PPh_3)_3RhCl$ (5 mol %) and DABCO (20 mol %) in EtOH was refluxed for 2.5 h according to *J. Org. Chem.* 1973, 38, 3224. Added 5% citric acid, stirred at 23° C. for 15 min, extracted with EtOAc, washed with brine, dried over $MgSO_4$. Removal of the solvent left an orange solid, which was purified by silica gel column chromatography with hexane/EtOAc to give the title compound.

Example R1

(5-Hydroxy-4-iodo-2-nitro-phenyl)-carbamic acid tert.-butyl ester

Prepared from (5-allyloxy-4-iodo-2-nitro-phenyl)-carbamic acid tert.-butyl ester (Example B4), $(PPh_3)_3RhCl$ (5 mol %) and DABCO (20 mol %) in EtOH according to the general procedure R. Obtained as a yellow solid.

MS (ISN) 379 [(M–H)$^-$]; mp 140° C.

General Procedure S

Preparation of 5-O-substituted-(4-iodo-2-nitro-phenyl)-carbamic acid tert.-butyl esters from (5-hydroxy-4-iodo-2-nitro-phenyl)-carbamic acid tert.-butyl ester A mixture of the (5-hydroxy-4-iodo-2-nitro-phenyl)-carbamic acid tert.-butyl ester (Example R1), $KHCO_3$ and the appropriate alkylating reagent were stirred in DMF at 23 to 60° C. until tlc indicated complete conversion. Dilution with EtOAc was followed by aqueous workup with 5% citric acid, sat. $NaHCO_3$-sol., brine and drying over $MgSO_4$. Removal of the solvent left a crude material, which was purified by silica gel column chromatography with hexane/EtOAc to give the title compound.

Example S1

(5-tert.-Butoxycarbonylamino-2-iodo-4-nitro-phenoxy)-acetic acid tert.-butyl ester Prepared from (5-hydroxy-4-iodo-2-nitro-phenyl)-carbamic acid tert.-butyl ester (Example R1) (1.23 g, 3.24 mmol), $KHCO_3$ (0.39 g, 3.89 mmol) and tert.-butyl bromoacetate (0.59 mL, 3.89 mmol) according to the general procedure S. Obtained as a yellow solid (1.5 g, 94%)

MS (ISP) 495 [(M+H)$^+$], 512 [(M+NH$_4$)$^+$] and 517 [(M+Na)$^+$]; mp 103° C.

Example S2

(5-Cyanomethoxy-4-iodo-2-nitro-phenyl)-carbamic acid tert.-butyl ester

Prepared from (5-hydroxy-4-iodo-2-nitro-phenyl)-carbamic acid tert.-butyl ester (Example R1) (614 mg, 1.62 mmol), $KHCO_3$ (208 mg, 2.08 mmol) and bromoacetonitrile (0.21 mL, 3.16 mmol) according to the general procedure S. Obtained as a yellow solid (574 mg, 85%).

MS (ISN) 418 [(M−H)⁻]; mp 125° C.

Example S3

(RS)-{4-Iodo-2-nitro-5-[2-(tetrahydro-pyran-2-yloxy)-ethoxy]-phenyl}-carbamic acid tert.-butyl ester Prepared from (5-hydroxy-4-iodo-2-nitro-phenyl)-carbamic acid tert.-butyl ester (Example R1) (760 mg, 2 mmol), $KHCO_3$ (260 mg, 4 mmol) and 2-(2-bromoethoxy)tetrahydro-2H-pyran (0.6 mL, 2.6 mmol) according to the general procedure S. Obtained as an orange oil (804 mg, 79%).

MS (EI) 508 (M⁺).

Example S4

(5-tert.-Butoxy-4-iodo-2-nitro-phenyl)-carbamic acid tert.-butyl ester

N,N-Dimethylformamide di-tert.butylacetal (19.2 mL, 80 mmol) was added dropwise within 15 min to a solution of (5-hydroxy-4-iodo-2-nitro-phenyl)-carbamic acid tert.-butyl ester (Example R1) (7.60 g, 20 mmol) in toluene at 80° C. and stirring was continued at 80° C. for 3 h (cf. *Synthesis* 1983, 135). Obtained as a yellow solid (5.97 g, 68%).

MS (ISN) 435 [(M−H)⁻]; mp 94° C.

Example 1

3-(7-Iodo-4-oxo-8-thiomorpholin-4-yl-4,5-dihydro-3H-benzo[b][1,4]diazepin-2-yl)-benzonitrile Prepared from 2-[3-(3-cyano-phenyl)-3-oxo-propionylamino]-4-iodo-5-thiomorpholin-4-yl-phenyl}-carbamic acid tert.-butyl ester (Example O1) (629 mg, 1.04 mmol) by treatment with TFA in $CH_2Cl_2$ according to the general procedure P. Obtained as an olive solid (437 mg).

mp 227–228° C. (dec.).

Example 2

3-(7-Iodo-8-morpholin-4-yl-4-oxo-4,5-dihydro-3H-benzo[b][1,4]diazepin-2-yl-benzonitrile Prepared from {2-[3-(3-cyano-phenyl)-3-oxo-propionylamino]-4-iodo-5-morpholin-4-yl-phenyl}-carbamic acid tert.-butyl ester (Example O2) (518 mg, 0.877 mmol) by treatment with TFA in $CH_2Cl_2$ according to the general procedure P. Obtained as a beige solid (309 mg).

MS (EI) 472 (M⁺); mp 224° C. (dec.).

Example 3

3-(8-Chloro-4-oxo-7-phenylethynyl-4,5-dihydro-3H-benzo[b][1,4]diazepin-2-yl)-benzonitrile Prepared from (2-amino-5-chloro-4-phenylethynyl-phenyl)-carbamic acid tert.-butyl ester (Example L3) (171 mg, 0.5 mmol) and 3-(2,2-dimethyl-6-oxo-6H-[1,3]dioxin-4-yl)-benzonitrile (Example N4) (183 mg, 0.6 mmol) according to the general procedure O. Obtained as a light yellow solid (284 mg). This material was deprotected and cyclized by treatment with TFA in CH₂Cl2 according to the general procedure P. Obtained as an orange solid (483 mg).

MS (ISP) 343 [(M+H)⁺] and 345 [(M+2+Na)⁺]; mp 248–251° C. (dec.).

Example 4

3-(8-Methyl-4-oxo-7-phenylethynyl-4,5-dihydro-3H-benzo[b][1,4]diazepin-2-yl)-benzonitrile Prepared from (2-amino-5-methyl-4-phenylethynyl-phenyl)-carbamic acid tert.-butyl ester (Example L4) (161 mg, 0.5 mmol) and 3-(2,2-dimethyl-6-oxo-6H-[1,3]dioxin-4-yl)-benzonitrile (Example N4) (230 mg, 0.75 mmol, 75% pure) according to the general procedure O. Obtained as a light yellow solid (227 mg). This material was deprotected and cyclized by treatment with TFA in $CH_2Cl_2$ according to the general procedure P. Obtained as a light yellow solid (83 mg).

MS (ISP) 375 (M⁺); mp 237–239° C. (dec.).

Example 5

3-[8-(4-Methyl-piperazin-1-yl)-4-oxo-7-phenylethynyl-4,5-dihydro-3H-benzo[b][1,4]diazepin-2-yl]-benzonitrile Prepared from [2-amino-5-(4-methyl-piperazin-1-yl)-4-phenylethynyl-phenyl]-carbamic acid tert.-butyl ester (Example L5) (203 mg, 0.5 mmol) and 3-(2,2-dimethyl-6-oxo-6H-[1,3]dioxin-4-yl)-benzonitrile (Example N4) (230 mg, 0.75 mmol, 75% pure) according to the general procedure O. Obtained by chromatography as an orange oil (181 mg). This material was deprotected and cyclized by treatment with TFA in $CH_2Cl_2$ according to the general procedure P. Obtained as an orange solid (82 mg).

MS (ISP) 460.5 [(M+H)⁺]; mp 222–224° C. (dec.).

Example 6

3-[8-(1,1-Dioxo-thiomorpholin-4-yl)-4-oxo-7-phenylethynyl-4,5-dihydro-3H-benzo[b][1,4]diazepin-2-yl]-benzonitrile Prepared from [2-amino-5-(1,1-dioxo-6-thiomorpholin-4-yl)-4-phenylethynyl-phenyl]-carbamic acid tert.-butyl ester (Example L19) (220 mg, 0.5 mmol) and 3-(2,2-dimethyl-6-oxo-6H-[1,3]dioxin-4-yl)-benzonitrile (Example N4) (172 mg, 0.75 mmol) according to the general procedure O. The obtained material was deprotected and cyclized by treatment with TFA in $CH_2Cl_2$ according to the general procedure P. Obtained as a yellow solid (47 mg).

MS (ISP) 495 [(M+H)⁺]; mp>250° C. (dec.).

Example 7

3-(8-Chloro-4-oxo-7-phenyl-4,5-dihydro-3H-benzo[b][1,4]diazepin-2-yl)-benzonitrile Prepared from {2-chloro-5-[3-(3-cyano-phenyl)-3-oxo-propionylamino]-biphenyl-4-yl}-carbamic acid tert.-butyl ester (Example O3) (720 mg, 1.47 mmol) by treatment with TFA in $CH_2Cl_2$ according to the general procedure P. Obtained as an off-white solid (457 mg).

MS (EI) 371 (M⁺) and 373 [(M+2)⁺]; mp 242–244° C. (dec.).

Example 8

3-(8-Methyl-4-oxo-7-phenyl-4,5-dihydro-3H-benzo[b][14]diazepin-2-yl)-benzonitrile Prepared from (5-amino-2-methyl-biphenyl-4-yl)-carbamic acid tert.-butyl ester (Example L7) (298 mg, 1.0 mmol) and 3-(2,2-dimethyl-6-oxo-6H-[1,3]dioxin-4-yl)- benzonitrile (Example N4) (460 mg, 1.5 mmol) according to the general procedure O. The obtained material (351 mg) was deprotected and cyclized by treatment with TFA in $CH_2Cl_2$ according to the general procedure P. Obtained as a light yellow solid (206 mg).

MS (EI) 351 (M⁺); mp 236–239° C. (dec.).

Example 9

3-[8-(1,4-Dioxa-8-aza-spiro[4.5]dec-8-yl)-4-oxo-7-phenylethynyl-4,5-dihydro-3H-benzo[b][1,4]diazepin-2-yl]-benzonitrile Prepared from [2-[3-(3-cyano-phenyl)-3-oxo-propionylamino]-5-(1,4-dioxa-8-aza-spiro[4.5]dec-8-yl)-4-phenylethynyl-phenyl]-carbamic acid tert.-butyl ester (Example O14) (265 mg, 0.43 mmol) by treatment with TFA in $CH_2Cl_2$ according to the general procedure P. Obtained as a brown solid (121 mg).

MS (ISP) 503 [(M+H)⁺]; mp 239–243° C. (dec.).

Example 10

3-(8-Morpholin-4-yl-4-oxo-7-phenylethynyl-4,5-dihydro-3H-benzo[b][1,4]diazepin-2-yl-)-benzonitrile Prepared from {2-[3-(3-cyano-phenyl)-3-oxo-propionylamino]-5-morpholin-4-yl-4-phenylethynyl-phenyl}-carbamic acid tert.butyl ester O10 (370 mg, 0.66 mmol) by treatment with TFA in $CH_2Cl_2$ according to the general procedure P. Obtained as a light brown solid (216 mg).

MS (EI) 446 (M⁺); mp 239–243° C. (dec.).

Example 11

3-[8-(2-Dimethylamino-ethylsulfanyl)-4-oxo-7-phenylethynyl-4,5-dihydro-3H-benzo[b][1,4]diazepin-2-yl]-benzonitrile Prepared from [2-[3-(3-cyano-phenyl)-3-oxo-propionylamino]-5-(2-dimethylamino-ethylsulfanyl)-4-phenylethynyl-phenyl]-carbamic acid tert.-butyl ester (example O4) (166 mg, 0.28 mmol) by treatment with TFA and anisole in CH2Cl2 according to the general procedure P. Obtained as a light yellow solid (103 mg).

MS (ISP) 465 [(M+H)⁺]; mp 197° C. (dec.).

Example 12

[4-(3-Cyano-phenyl)-2-oxo-8-phenylethynyl-2,3-dihydro-1H-benzo[b][1,4]diazepin-7-ylsulfanyl]-acetic acid methyl ester Prepared from {5-tert.-butoxycarbonylamino-4-[3-(3-cyano-phenyl)-3-oxo-propionylamino]-2-phenylethynyl-phenylsulfanyl}-acetic acid methyl ester (Example O5)(421 mg, 0.72 mmol) by treatment with TFA and anisole in $CH_2Cl_2$ according to the general procedure P. Obtained as a light yellow solid (309 mg).

MS (ISP) 465 [(M+H)⁺]; mp 201° C. (dec.).

Example 13

[4-(3-Cyano-phenyl)-2-oxo-8-phenylethynyl-2,3-dihydro-1H-benzo[b][1,4]diazepin-7-ylsulfanyl]-acetic acid A solution of [4-(3-cyano-phenyl)-2-oxo-8-phenylethynyl-2,3-dihydro-1H-benzo[b][1,4]diazepin-7-ylsulfanyl]-acetic acid methyl ester (Example 12) (265 mg, 0.57 mmol) and $LiOH.H_2O$ (26 mg, 0.63 mmol) in THF (5 mL), MeOH (1 mL) and $H_2O$ (1 mL) was stirred at 23° C. for 24 h. Obtained as a light yellow solid (257 mg).

MS (ISP) 452 [(M+H)⁺]; mp 202° C. (dec.).

Example 14

[4-(3-Cyano-phenyl)-2-oxo-8-phenylethynyl-2,3-dihydro-1H-benzo[b][1,4]diazepin-7-yl]-acetic acid methyl ester Prepared from {5-tert.-butoxycarbonylamino-4-[3-(3-cyano-phenyl)-3-oxo-propionylamino]-2-phenylethynyl-phenyl}-acetic acid methyl ester (Example O6) (846 mg, 1.53 mmol) by treatment with TFA in $CH_2Cl_2$ according to the general procedure P. Obtained as a light yellow solid (557 mg).

MS (EI) 433 (M⁺); mp 236° C. (dec.).

Example 15

[4-(3-Cyano-phenyl)-2-oxo-8-phenylethynyl-2,3-dihydro-1H-benzo[b][1,4]diazepin-7yl]-acetic acid A solution of $LiOH.H_2O$ (54 mg, 1.28 mmol) in $H_2O$ (2 mL) and MeOH (2 mL) was added to [4-(3-cyano-phenyl)-2-oxo-8-phenylethynyl-2,3-dihydro-1H-benzo[b][1,4]diazepin-7yl]-acetic acid methyl ester (Example 14) (505 mg, 1.17 mmol) in THF (10 mL) and the reaction mixture was stirred at 23° C. for 48 h. Obtained as a light yellow solid (62 mg).

MS (ISP) 452 [(M+H)⁺]; mp 248° C. (dec.).

Example 16

4-(3-Cyano-phenyl)-8-iodo-2-oxo-2,3-dihydro-1H-benzo[b][1,4]diazepine-7-carboxyl acid methyl ester Prepared from 5-tert.-butoxycarbonylamino-4-[3-(3-cyano-phenyl)-3-oxo-propionylamino]-2-iodo-benzoic acid methyl ester (Example O17) (430 mg, 0.763 mmol) by treatment with TFA in $CH_2Cl_2$ according to the general procedure P. Obtained as a salmon colored solid (199 mg).

MS (EI) 445 (M⁺); mp 247–248° C. (dec.).

Example 17

2-[4-(3-Cyano-phenyl)-2-oxo-8-phenylethynyl-2,3-dihydro-1H-benzo[b][1,4]diazepin-7-yl]-acetamide

[4-(3-Cyano-phenyl)-2-oxo-8-phenylethynyl-2,3-dihydro-1H-benzo[b][1,4]diazepin-7-yl]-acetic acid (Example 15) (48 mg, 0.114 mmol) was treated with $Boc_2O$ (37 mg), $NH_4HCO_3$ (13 mg) and pyridine (6 µL) in DMF (0.6 mL) at 23° C. for 24 h [cf *Tetrahedron Letters* 1995, 36, 7115]. Obtained as a light yellow solid (14 mg).

MS (ISN) 417 [(M−H)⁻]; mp 250° C. (dec.).

Example 18

3-[8-(2-Methoxy-ethoxy)-4-oxo-7-phenylethynyl-4,5-dihydro-3H-benzo[b][1,4]diazepin-2-yl]-benzonitrile Prepared from [2-[3-(3-cyano-phenyl)-3-oxo-propionylamino]-5-(2-methoxy-ethoxy)-4-phenylethynyl-phenyl]-carbamic acid tert.-butyl ester (Example O7) (135 mg, 0.251 mmol) by treatment with TFA in $CH_2Cl_2$ accord ing to the general procedure P. Obtained as a light green solid (82 mg).

MS (EI) 435 (M⁺); mp 174–176° C.

Example 19

4-(3-Cyano-phenyl)-2-oxo-8-phenylethynyl-2,3-dihydro-1H-benzo[b][1,4]diazepine-7-carboxylic acid methyl ester Prepared from 5-tert.-butoxycarbonylamino-4-[3-(3-cyano-phenyl)-3-oxo-propionylamino]-2-phenylethynyl-benzoic acid methyl ester (Example O9) (511 mg, 0.95 mmol) by treatment with TFA in CH₂Cl₂ according to the general procedure P. Obtained as an off-white solid (321 mg).

MS (EI) 419 (M⁺); mp>250° C.

Example 20

3-(8-Methoxy-4-oxo-7-phenylethynyl-4,5-dihydro-3H-benzo[b][1,4]diazepin-2-yl)-benzonitrile Prepared from {2-[3-(3-cyano-phenyl)-3-oxo-propionylamino]-5-methoxy-4-phenylethynyl-phenyl}-carbamic acid tert.-butyl ester (Example O8) (359 mg, 0.7 mmol) by treatment with TFA in CH₂Cl₂ according to the general procedure P. Obtained as a yellow-brown solid (87 mg).

MS (EI) 391 (M⁺); mp>250° C.

Example 21

3-[8-(2-{2-[2-(2-Methoxy-ethoxy)-ethoxy]-ethoxy}-ethoxy)-4-oxo-7-phenylethynyl-4,5-dihydro-3H-benzo[b][1,4]diazepin-2-yl]-benzonitrile Prepared from [2-[3-(3-cyano-phenyl)-3-oxo-propionylamino]-5-(2-{2-[2-(2-methoxy-ethoxy)-ethoxy]-ethoxy}-ethoxy)-4-phenylethynyl-phenyl]-carbamic acid tert.-butyl ester (Example O11) (300 mg, 0.437 mmol) by treatment with TFA in CH₂Cl₂ according to the general procedure P. Obtained as a light yellow solid (211 mg).

MS (EI) 435 (M⁺); mp 140–141° C. (dec.).

Example 22

[4-(3-Cyano-phenyl)-2-oxo-8-phenylethynyl-2,3-dihydro-1H-benzo[b][1,4]diazepin-7-yloxy]-acetic acid Prepared from {5-tert.-butoxycarbonylamino-4-[3-(3-cyano-phenyl)-3-oxo-propionylamino]-2-phenylethynyl-phenoxy}-acetic acid tert.-butyl ester (Example O12) (698 mg, 1.14 mmol) by treatment with TFA in CH₂Cl₂ and anisole according to the general procedure P. Obtained as a yellow solid (265 mg).

MS (ISN) 434 [(M−H)⁻]; mp 257° C. (dec.).

Example 23

3-(8-Cyanomethyl-4-oxo-7-phenylethynyl-4,5-dihydro-3H-benzo[b][1,4]diazepin-2-yl)-benzonitrile Prepared from {5-cyanomethyl-2-[3-(3-cyano-phenyl)-3-oxo-propionylamino]-4-phenylethynyl-phenyl}-carbamic acid tert.-butyl ester (Example O13) (266 mg, 0.51 mmol) by treatment with TFA in CH₂Cl₂ and anisole according to the general procedure P. Obtained as a yellow solid (145 mg).

MS (EI) 400 (M⁺); mp 262° C. (dec.).

Example 24

3-[8-(2,3-Dihydroxy-propoxy)-4-oxo-7-phenylethynyl-4,5-dihydro-3H-benzo[b][1,4]diazepin-2-yl]-benzonitrile Prepared from [2-[3-(3-cyano-phenyl)-3-oxo-propionylamino]-5-(2,2-dimethyl-[1,3]dioxolan-4-ylmethoxy)-4-phenylethynyl-phenyl]-carbamic acid tert.-butyl ester (Example O16) (265 mg, 0.435 mmol) by treatment with TFA in CH₂Cl₂ and anisole according to the general procedure P. Obtained as a yellow solid (62 mg).

MS (ISP) 452 [(M+H)⁺] and 474 [(M+Na)⁺]; mp 230–234° C. (dec.).

Example 25

4-(3-Iodo-phenyl)-7-(2-methoxy-ethoxy)-8-phenylethynyl-1,3-dihydro-benzo[b]1,4]diazepin-2-one Prepared from [2-[3-(3-iodo-phenyl)-3-oxo-propionylamino]-5-(2-methoxy-ethoxy)-4-phenylethynyl-phenyl]-carbamic acid tert.-butyl ester (Example O15) (1.24 g, 1.89 mmol) by treatment with TFA in CH₂Cl₂ and anisole according to the general procedure P. Obtained as a yellow solid (517 mg).

MS (EI) 536 (M⁺); mp 192° C. (dec.).

Example 26

2-[4-(3-Cyano-phenyl)-2-oxo-8-phenylethynyl-2,3-dihydro-1H-benzo[b][1,4]diazepin-7-yloxy]-acetamide EDC (42 mg, 0.22 mmol) was added to [4-(3-cyano-phenyl)-2-oxo-8-phenylethynyl-2,3-dihydro-1H-benzo[b][1,4]diazepin-7-yloxy]-acetic acid (Example 22) (50 mg, 0.11 mmol), NH₄Cl (18 mg, 0.33 mmol) and NMM (56 mg, 0.55 mmol) in DMF (1.1 mL) at 0° C. and the reaction mixture was stirred at 23° C. for 2 h. Obtained as a yellow solid (5 mg).

MS (ISN) 417 [(M−H)⁻]; mp 250° C. (dec.).

Example 27

4-(3-Imidazol-1-yl-phenyl)-7-(2-methoxy-ethoxy)-8-phenylethynyl-1,3-dihydro-benzo[b][1,4]diazepin-2-one Prepared from [[[2-[3-(3-Imidazol-1-yl-phenyl)-3-oxo-propionylamino]-5-(2-methoxy-ethoxy)-4-phenylethynyl-phenyl]-carbamic acid tert.-butyl ester (Example O18) (200 mg, 0.336 mmol) by treatment with TFA in CH₂Cl₂ and anisole according to the general procedure P. Obtained as a yellow solid (28 mg).

MS (EI) 476 (M⁺); mp 187–189° C.

Example 28

[RS]-3-[4-Oxo-8-(2-oxo-[1,3]dioxolan-4-ylmethoxy)-7-phenylethynyl-4,5-dihydro-3H-benzo[b][1,4]diazepin-2-yl]-benzonitrile Prepared from [RS]-[2-[3-(3-cyano-phenyl)-3-oxo-propionylamino]-5-(2-oxo-[1,3]dioxolan-4-ylmethoxy)-4-phenylethynyl-phenyl]-carbamic acid tert.-butyl ester (Example O19) (400 mg, 0.67 mmol) by treatment with TFA

Example 29

3-(8-Ethoxymethyl-4-oxo-7-phenylethynyl-4,5-dihydro-3H-benzo [b][1,4]diazepin-2-yl)-benzonitrile Prepared from {2-[3-(3-cyano-phenyl)-3-oxo-propionylamino]-5-ethoxymethyl-4-phenylethynyl-phenyl}-carbamic acid tert.-butyl ester (Example O20) (140 mg, 0.26 mmol) by treatment with TFA in CH$_2$Cl$_2$ according to the general procedure P. Obtained as a yellow solid (93 mg).

MS (EI) 419 (M$^+$); mp 229° C.

Example 30

2,2-Dimethyl-propionic acid 4-(3-cyano-phenyl)-2-oxo-8-phenylethynyl-2,3-dihydro-1H-benzo[b][1,4]diazepin-7-ylmethyl ester Prepared from 2,2-dimethyl-propionic acid 5-tert.-butoxycarbonylamino-4-[3-(3-cyano-phenyl)-3-oxo-propionylamino]-2-phenylethynyl-benzyl ester (Example O21) (156 mg, 0.26 mmol) by treatment with TFA in CH$_2$Cl$_2$ according to the general procedure P. Obtained as a light yellow solid (75 mg).

MS (EI) 475 (M$^+$); mp 218° C.

Example 31

3-(8-Hydroxymethyl-4-oxo-7-phenylethynyl-4,5-dihydro-3H-benzo[b][1,4]diazepin-2-yl)-benzonitrile Prepared from 2,2-dimethyl-propionic acid 4-(3-cyano-phenyl)-2-oxo-8-phenylethynyl-2,3-dihydro-1H-benzo[b][1,4]diazepin-7-ylmethyl ester (Example 30) (30 mg, 0.063 mmol) and LiOH.H$_2$O (8 mg, 0.289 mmol) in THF (2 mL), MeOH (0.4 mL) and H$_2$O (0.4 mL) at 23° C. for 3 days. Obtained as a yellow solid (17 mg).

MS (EI) 391 (M$^+$); mp >255° C.

Example 32

7-Hydroxymethyl-4-(3-imidazol-1-yl-phenyl)-8-phenylethynyl-1,3-dihydro-benzo[b][1,4]diazepin-2-one Prepared from (RS)-[2-[3-(3-imidazol-1-yl-phenyl)-3-oxo-propionylamino]-4-phenylethynyl-5-(tetrahydro-pyran-2-yloxymethyl)-phenyl]-carbamic acid tert.-butyl ester (Example O22) by treatment with TFA in CH$_2$Cl$_2$ according to the general procedure P. Obtained as a yellow solid (77 mg).

MS (EI) 432 (M$^+$); mp 227° C.

Example 33

4-(3-Imidazol-1-yl-phenyl)-7-(4-methoxy-piperidin-1-yl)-8-phenylethynyl-1,3-dihydro-benzo[b][1,4]diazepin-2-one Prepared from [2-[3-(3-imidazol-1-yl-phenyl)-3-oxo-propionylamino]-5-(4-methoxy-piperidin-1-yl)-4-phenylethynyl-phenyl]-carbamic acid tert.-butyl ester (Example O23) by treatment with TFA in CH$_2$Cl$_2$ according to the general procedure P. Obtained as a yellow solid (159 mg).

MS (ISP) 516 [(M+H)$^+$]; mp 222° C.

Example 34

3-[8-(4-Methoxy-piperidin-1-yl)-4-oxo-7-phenylethynyl-4,5-dihydro-3H-benzo[b][1,4]diazepin-2-yl]-benzonitrile Prepared from [2-[3-(3-cyano-phenyl)-3-oxo-propionylamino]-5-(4-methoxy-piperidin-1-yl)-4-phenylethynyl-phenyl]-carbamic acid tert.-butyl ester (Example O24) by treatment with TFA in CH$_2$Cl$_2$ according to the general procedure P. Obtained as a yellow solid (128 mg).

MS (ISP) 475 [(M+H)$^+$]; mp 250–251° C.

Example 35

[4-(3-Imidazol-1-yl-phenyl)-2-oxo-8-phenylethynyl-2,3-dihydro-1H-benzo[b][1,4]diazepin-7-yloxy]-acetonitrile Prepared from {5-cyanomethoxy-2-[3-(3-imidazol-1-yl-phenyl)-3-oxo-propionylamino]-4-phenylethynyl-phenyl}-carbamic acid tert.-butyl ester (Example O25) by treatment with TFA in CH$_2$Cl$_2$ according to the general procedure P. Obtained as a yellow solid (43 mg).

MS (EI) 457 (M$^+$); mp 214° C.

Example 36

3-(8-Cyanomethoxy-4-oxo-7-phenylethynyl-4,5-dihydro-3H-benzo[b][1,4]diazepin-2-yl)-benzonitrile Prepared from {5-cyanomethoxy-2-[3-(3-cyano-phenyl)-3-oxo-propionylamino]-4-phenylethynyl-phenyl}-carbamic acid tert.-butyl ester (Example O26) by treatment with TFA in CH$_2$Cl$_2$ according to the general procedure P. Obtained as a yellow solid (71 mg).

MS (EI) 416 (M$^+$); mp 212° C.

Example 37

8-(4-Fluoro-phenylethynyl)-7-hydroxymethyl-4-(3-imidazol-1-yl-phenyl)-1,3-dihydro-benzo[b][1,4]diazepin-2-one Prepared from (RS)-[4-(4-fluoro-phenylethynyl)-2-[3-(3-imidazol-1-yl-phenyl)-3-oxo-propionylamino]-5-(tetrahydro-pyran-2-yloxymethyl)-phenyl]-carbamic acid tert.-butyl ester (Example O27) by treatment with TFA in CH$_2$Cl$_2$ according to the general procedure P. Obtained as a yellow solid (462 mg).

MS (EI) 450 (M$^+$); mp 234° C. (dec.).

Example 38

8-(4-Fluoro-phenylethynyl)-7-[(2-hydroxy-ethyl)-methyl-amino]-4-(3-imidazol-1-yl-phenyl)-1,3-dihydro-benzo[b][1,4]diazepin-2-one Prepared from (RS)-(4-(4-fluoro-phenylethynyl)-2-[3-(3-imidazol-1-yl-phenyl)-3-oxo-propionylamino]-5-{methyl-[2-(tetrahydro-pyran-2-yloxy)-ethyl]-amino}-phenyl)-carbamic acid tert.-butyl ester (Example O28) by treatment with TFA in CH$_2$Cl$_2$ according to the general procedure P. Obtained as a yellow solid (73 mg).

MS (EI) 493 (M$^+$); mp 217° C. (dec.).

Example 39

4-(3-Imidazol-1-yl-phenyl)-7-(4-oxo-piperidin-1-yl)-8-phenylethynyl-1,3-dihydro-benzo[b][1,4]diazepin-2-one Prepared from {5-(4,4-diethoxy-piperidin-1-yl)-2-[3-(3-imidazol-1-yl-phenyl)-3-oxo-propionylamino]-4- phenylethynyl-phenyl}-carbamic acid tert.-butyl ester (Example O29) by treatment with TFA in CH$_2$Cl$_2$ according to the general procedure P. Obtained as a yellow solid (180 mg).

MS (EI) 499 (M$^+$); mp 231° C. (dec.).

Example 40

N-tert.-Butyl-2-[4-(3-cyano-phenyl)-2-oxo-8-phenylethynyl-2,3-dihydro-1H-benzo[b][1,4] diazepin-7-yloxy]-acetamide Prepared from [4-(3-cyano-phenyl)-2-oxo-8-phenylethynyl-2,3-dihydro-1H-benzo[b][1,4]diazepin-7-yloxy]-acetic acid (Example 22) (87 mg, 0.2 mmol) by treatment with oxalyl chloride (26 uL, 0.3 mmol) in DMF (0.6 mL) at 0° C. for 1 h, then with tert.-butylamine (106 uL, 1.0 mmol) at 0° C. for further 30 min. Obtained as a yellow solid (21 mg).

MS (EI) 490 (M$^+$); mp>250° C.

Example 41

2-[4-(3-Cyano-phenyl)-2-oxo-8-phenylethynyl-2,3-dihydro-1H-benzo[b][1,4]diazepin-7-yloxy]-N-methoxy-acetamide Prepared from [4-(3-cyano-phenyl)-2-oxo-8-phenylethynyl-2,3-dihydro-1H-benzo[b][1,4]diazepin-7-yloxy]-acetic acid (Example 22) (44 mg, 0.1 mmol) by treatment with EDC (38 mg, 0.2 mmol), MeONH2.HCl (9 mg, 0.11 mmol), NMM (0.021 mL, 0.3 mmol) and HOBt (15 mg, 0.11 mmol) in DMF (1 mL) at 0 to 23° C. for 20 h. Obtained as a yellow solid (36 mg).

MS (ISP) 465 [(M+H)$^+$]; mp>250° C.

Example 42

7-(2-Hydroxy-ethoxy)-4-(3-imidazol-1-yl-phenyl)-8-phenylethynyl-1,3-dihydro-benzo[b][1,4]diazepin-2-one Prepared from (RS)-{2-[3-(3-imidazol-1-yl-phenyl)-3-oxo-propionylamino]-4-phenylethynyl-5-[2-(tetrahydro-pyran-2-yloxy)-ethoxy]-phenyl}-carbamic acid tert.-butyl ester (Example O29) by treatment with TFA in CH$_2$Cl$_2$ according to the general procedure P. Obtained as a light yellow solid (48 mg).

MS (EI) 462 (M$^+$); mp 224–227° C.

Example 43

8-(4-Fluoro-phenyl)-7-(4-hydroxy-piperidin-1-yl)-4-(3-imidazol-1-yl-phenyl)-1,3-dihydro-benzo[b][1,4] diazepin-2-one Prepared from (RS)-{4'-fluoro-5-[3-(3-imidazol-1-yl-phenyl)-3-oxo-propionylamino]-2-[4-(tetrahydro-pyran-2-yloxy)-piperidin-1-yl]-biphenyl-4-yl}-carbamic acid tert.-butyl ester (Example O31) by treatment with TFA in CH$_2$Cl$_2$ according to the general procedure P. Obtained as a light yellow solid (109 mg).

MS (ISP) 496 [(M+H)$^+$]; mp 238–240° C.

Example 44

8-(4-Fluoro-phenylethynyl)-7-(2-hydroxy-ethoxy)-4-(3-imidazol-1-yl-phenyl)-1,3-dihydro-benzo[b][1,4] diazepin-2-one Prepared from {5-(2-tert.-butoxy-ethoxy)-4-(4-fluoro-phenylethynyl)-2-[3-(3-imidazol-1-yl -phenyl)-3-oxo-propionylamino]-phenyl}-carbamic acid tert.-butyl ester (Example O32) by treatment with TFA in CH$_2$Cl$_2$ according to the general procedure P. Obtained as a light yellow solid (83 mg).

MS (EI) 480 (M$^+$); mp 220–222° C.

Example 45

8-(4-Fluoro-phenyl)-7-[4-(2-hydroxy-ethoxy)-piperidin-1-yl]-4-(3-imidazol-1-yl-phenyl)-1,3-dihydro-benzo[b][1,4]diazepin-2-one Prepared from (RS)-(4'-fluoro-5-[3-(3-imidazol-1-yl-phenyl)-3-oxo-propionylamino]-2-{4-[2-(tetrahydro-pyran-2-yloxy)-ethoxy]-piperidin-1-yl}-biphenyl-4-yl)-carbamic acid tert.-butyl ester (Example O33) by treatment with TFA in CH$_2$Cl$_2$ according to the general procedure P. Obtained as a light yellow solid (97 mg).

MS (ISP) 540 [(M+H)$^+$]; mp 225–227° C.

Example 46

8-(4-Fluoro-phenyl)-7-hydroxymethyl-4-(3-imidazol-1-yl-phenyl)-1,3-dihydro-benzo[b][1,4] diazepin-2-one Prepared from (RS)-[4'-fluoro-5-[3-(3-imidazol-1-yl-phenyl)-3-oxo-propionylamino]-2-(tetrahydro-pyran-2-yloxymethyl)-biphenyl-4-yl]-carbamic acid tert.-butyl ester (Example O34) by treatment with TFA in CH$_2$Cl$_2$ according to the general procedure P. Obtained as a light yellow solid (]62 mg).

MS (EI) 426 [(M)$^+$]; mp 180–195° C.

Example 47

[8-(4-Fluoro-phenyl)-4-(3-imidazol-1-yl-phenyl)-2-oxo-2,3-dihydro-1H-benzo[b ][1,4]diazepin-7-yloxy]-acetonitrile Prepared from {2-cyanomethoxy-4'-fluoro-5-[3-(3-imidazol-1-yl-phenyl)-3-oxo-propionylamino]-biphenyl-4-yl}-carbamic acid tert.-butyl ester (Example O35) by treatment with TFA in CH$_2$Cl$_2$ according to the general procedure P. Obtained as a yellow solid (11 mg).

MS (EI) 451 (M$^+$); mp 164° C.

Example 48

7-Dimethylaminomethyl-8-(4-fluoro-phenyl)-4-(3-imidazol-1-yl-phenyl)-1,3-dihydro-benzo[b][1,4] diazepin-2-one Prepared from {2-dimethylaminomethyl-4'-fluoro-5-[3-(3-imidazol-1-yl-phenyl)-3-oxo-propionylamino]-biphenyl-4-yl}-carbamic acid tert.-butyl ester (Example O36) by treatment with TFA in CH$_2$Cl$_2$ according to the general procedure P. Obtained as a brown solid (180 mg).

MS (ISP) 454 (M+H)$^+$; mp 115–140° C. (dec.).

Example 49

7-(2,2-Dimethyl-tetrahydro-[1,3]dioxolo [4,5-c] pyrrol-5-yl)-8-(4-fluoro-phenyl)-4-(3-imidazol-1-yl-phenyl)-1,3-dihydro-benzo[b][1,4]diazepin-2-one Prepared from {2-(2,2-dimethyl-tetrahydro-[1,3]dioxolo [4,5-c]pyrrol-5-yl)-4'-fluoro-5-[3-(3-imidazol-1-yl-phenyl)-3-oxo-propionylamino]-biphenyl-4-yl}-carbamic acid tert.- butyl ester (Example O37) by treatment with TFA in CH$_2$Cl$_2$ according to the general procedure P. Obtained as a yellow solid (358 mg).

MS (EI) 537 (M$^+$); mp 240° C. (dec.).

Example 50

7-(cis-3,4-Dihydroxy-pyrrolidin-1-yl)-8-(4-fluoro-phenyl)-4-(3-imidazol-1-yl-phenyl)-1,3-dihydro-benzo[b][1,4]diazepin-2-one Prepared from 7-(2,2-dimethyl-tetrahydro-[1,3]dioxolo[4,5-c]pyrrol-5-yl)-8-(4-fluoro-phenyl)-4-(3-imidazol-1-yl-phenyl)-1,3-dihydro-benzo[b][1,4]diazepin-2-one (Example 49) (304 mg, 0.57 mmol) by treatment 13% HCl (15 mL) in THF (50 mL) at 23° C. for 16 h. Obtained as a yellow solid (209 mg).

MS (ISP) 498 [(M+H)$^+$]; mp 244° C.

Example 51

8-(4-Fluoro-phenyl)-4-(3-imidazol-1-yl-phenyl)-7-methoxy-1,3-dihydro-benzo[b][1,4]diazepin-2-one Prepared from {4'-fluoro-5-[3-(3-imidazol-1-yl-phenyl)-3-oxo-propionylamino]-2-methoxy-biphenyl-4-yl}-carbamic acid tert.-butyl ester (Example O38) by treatment with TFA in CH$_2$Cl$_2$ according to the general procedure P. Obtained as a yellow solid (182 mg).

MS (EI) 426 (M$^+$); mp 221° C. (dec.).

Example 52

8-(4-Fluoro-phenyl)-4-(3-imidazol-1-yl-phenyl)-7-(4-oxo-piperidin-1-yl)-1,3-dihydro-benzo[b][1,4]diazepin-2-one Prepared from {2-(1,4-dioxa-8-aza-spiro[4.5]dec-8-yl)-4'-fluoro-5-[3-(3-imidazol-1-yl-phenyl)-3-oxo-propionylamino]-biphenyl-4-yl}-carbamic acid tert.-butyl ester (Example O39) by treatment with TFA in CH$_2$Cl$_2$ according to the general procedure P. Obtained as an orange-brown solid (150 mg).

MS (ISP) 494 [(M+H)$^+$]; mp 204° C.

Example 53

8-(4-Fluoro-phenyl)-4-(3-imidazol-1-yl-phenyl)-7-methyl-1,3-dihydro-benzo[b][1,4]diazepin-2-one Prepared from {4'-fluoro-5-[3-(3-imidazol-1-yl-phenyl)-3-oxo-propionylamino]-2-methyl-biphenyl-4-yl}-carbamic acid tert.-butyl ester (Example O40) by treatment with TFA in CH$_2$Cl$_2$ according to the general procedure P. Obtained as a light yellow solid (216 mg).

MS (EI) 410 (M$^+$); mp 196° C.

Example 54

[8-(4-Fluoro-phenyl)-4-(3-imidazol-1-yl-phenyl)-2-oxo-2,3-dihydro-1H-benzo[b][1,4]diazepin-7-yloxy-acetic acid Prepared from {4-tert.-butoxycarbonylamino-4'-fluoro-5-[3-(3-imidazol-1-yl-phenyl)-3-oxo-propionylamino]-biphenyl-2-yloxy}-acetic acid tert.-butyl ester (Example O41) by treatment with TFA in CH$_2$Cl$_2$ according to the general procedure P. Obtained as a beige solid (570 mg).

MS (ISP) 471 [(M+H)$^+$]; mp 209° C. (dec.).

Example 55

2-[8-(4-Fluoro-phenyl)-4-(3-imidazol-1-yl-phenyl)-2-oxo-2,3-dihydro-1H-benzo[b][1,4]diazepin-7-yloxy-N-hydroxy-acetamide Prepared from [8-(4-fluoro-phenyl)-4-(3-imidazol-1-yl-phenyl)-2-oxo-2,3-dihydro-1H-benzo[b][1,4]diazepin-7-yloxy]-acetic acid (Example 54) (94 mg, 0.2 mmol) by reaction with O-tritylhydroxylamine (61 mg, 0.22 mmol), HOBT (30 mg, 0.22 mmol), N-methylmorpholine (66 µL, 0.6 mmol) and EDC (77 mg, 0.4 mmol) in DMF (2 mL) from 0 to 23° C. for 18 h. After extraction and chromatography the resulting orange solid was stirred with TFA in CH$_2$Cl$_2$ according to the general procedure P. Obtained as a light yellow solid (71 mg).

MS (ISP) 486 [(M+H)$^+$]; mp 147–157° C. (dec.).

Example 56

7-Chloro-8-(4-fluoro-phenyl)-4-(3-imidazol-1-yl-phenyl)-1,3-dihydro-benzo[b][1,4]diazepin-2-one Prepared from {2-chloro-4'-fluoro-5-[3-(3-imidazol-1-yl-phenyl)-3-oxo-propionylamino]-biphenyl-4-yl}-carbamic acid tert.-butyl ester (Example O42) by treatment with TFA in CH$_2$Cl$_2$ according to the general procedure P. Obtained as a light yellow solid (35 mg).

MS (EI) 430 ((M$^+$); mp 209–211° C.

Example 57

8-(4-Fluoro-phenyl)-4-(3-imidazol-1-yl-phenyl)-7-(2-methoxy-ethoxy)-1,3-dihydro-benzo[b][1,4]diazepin-2-one Prepared from [4'-fluoro-5-[3-(3-imidazol-1-yl-phenyl)-3-oxo-propionylamino]-2-(2-methoxy-ethoxy)-biphenyl-4-yl]-carbamic acid tert.-butyl ester (Example O43) by treatment with TFA in CH$_2$Cl$_2$ according to the general procedure P. Obtained as a yellow solid (96 mg).

MS (EI) 470 ((M$^+$); mp 196–197° C.

Example 58

8-(4-Fluoro-phenyl)-7-(2-hydroxy-ethoxy)-4-(3-imidazol-1-yl-phenyl)-1,3-dihydro-benzo[b][1,4]diazepin-2-one Prepared from {2-(2-tert.-butoxy-ethoxy)-4'-fluoro-5-[3-(3-imidazol-1-yl-phenyl)-3-oxo-propionylamino]-biphenyl-4-yl}-carbamic acid tert.-butyl ester (Example O44) by treatment with TFA in CH$_2$Cl$_2$ according to the general procedure P. Obtained as a light green solid (95 mg).

MS (EI) 456 (M$^+$); mp 225° C.

Example 59

8-(4-Fluoro-phenyl)-4-(3-imidazol-1-yl-phenyl)-7-(2-oxo-oxazolidin-3-yl)-1,3-dihydro-benzo[b][1,4]diazepin-2-one Prepared from [4'-fluoro-5-[3-(3-imidazol-1-yl-phenyl)-3-oxo-propionylamino]-2-(2-oxo-oxazolidin-3-yl)-biphenyl-4-yl]-carbamic acid tert.-butyl ester (Example O45) by treatment with TFA in CH$_2$Cl$_2$ according to the general procedure P. Obtained as a yellow solid (35 mg).

MS (EI) 481 (M$^+$); mp 230° C.

Example 60

8-(4-Fluoro-2-methyl-phenyl)-4-(3-imidazol-1-yl-phenyl)-7-methoxy-1,3-dihydro-benzo[b][1,4]diazepin-2-one Prepared from {4'-fluoro-5-[3-(3-imidazol-1-yl-phenyl)-3-oxo-propionylamino]-2-methoxy-2'-methyl-biphenyl-4-

Example 61

8-(4-Fluoro-phenyl)-7-hydroxy-4-(3-imidazol-1-yl-phenyl)-1,3-dihydro-benzo[b][1,4]diazepin-2-one Prepared from {2-tert.-butoxy-4'-fluoro-5-[3-(3-imidazol-1-yl-phenyl)-3-oxo-propionylamino]-biphenyl-4-yl}-carbamic acid tert.-butyl ester (Example O47) by treatment with TFA in $CH_2Cl_2$ according to the general procedure P. Obtained as a yellow solid (109 mg).

MS (EI) 412 ($M^+$); mp 250° C.

Example 62

8-(2-Fluoro-phenyl)-7-hydroxy-4-(3-imidazol-1-yl-phenyl)-1,3-dihydro-benzo[b][1,4]diazepin-2-one Prepared from {2-tert.-butoxy-2'-fluoro-5-[3-(3-imidazol-1-yl-phenyl)-3-oxo-propionylamino]-biphenyl-4-yl}-carbamic acid tert.-butyl ester (Example O48) by treatment with TFA in $CH_2Cl_2$ according to the general procedure P. Obtained as a yellow solid (132 mg).

MS (EI) 412 (($M^+$); mp 220° C.

Example 63

8-(4-Fluoro-phenyl)-7-((R)-3-hydroxy-pyrrolidin-1-yl)-4-(3-imidazol-1-yl-phenyl)-1,3-dihydro-benzo[b][1,4]diazepin-2-one Prepared from (RS)-{4'-fluoro-5-[3-(3-imidazol-1-yl-phenyl)-3-oxo-propionylamino]-2-[(R)-3-(tetrahydro-pyran-2-yloxy)-pyrrolidin-1-yl]-biphenyl-4-yl}-carbamic acid tert.-butyl ester (Example O49) by treatment with TFA in $CH_2Cl_2$ according to the general procedure P. Obtained as a yellow solid (74 mg).

MS (EI) 481 ($M^+$); mp 155–158° C.

Example 64

8-(2-Fluoro-phenyl)-4-(3-imidazol-1-yl-phenyl)-7-methoxy-1,3-dihydro-benzo[b][1,4]diazepin-2-one Prepared from {2'-fluoro-5-[3-(3-imidazol-1-yl-phenyl)-3-oxo-propionylamino]-2-methoxy-biphenyl-4-yl}-carbamic acid tert.-butyl ester (Example O50) by treatment with TFA in $CH_2Cl_2$ according to the general procedure P. Obtained as a yellow solid (68 mg).

MS (EI) 426 (($M^+$); mp 216° C. (dec.).

Example 65

3-[7-(4-Fluoro-phenyl)-8-hydroxy-4-oxo-4,5-dihydro-3H-benzo[b][1,4]diazepin-2-yl]-benzonitrile Prepared from {2-tert.-butoxy-5-[3-(3-cyano-phenyl)-3-oxo-propionylamino]-4'-fluoro-biphenyl-4-yl}-carbamic acid tert.-butyl ester (Example O51) by treatment with TFA in $CH_2Cl_2$ according to the general procedure P. Obtained as a yellow solid (66 mg).

MS (EI) 371 (($M^+$); mp>250° C.

Example 66

3-[7-(2-Fluoro-phenyl)-8-hydroxy-4-oxo-4,5-dihydro-3H-benzo[b][1,4]diazepin-2-yl]-benzonitrile Prepared from {2-tert.-butoxy-5-[3-(3-cyano-phenyl)-3-oxo-propionylamino]-2'-fluoro-biphenyl-4-yl}-carbamic acid tert.-butyl ester (Example O52) by treatment with TFA in $CH_2Cl_2$ according to the general procedure P. Obtained as a yellow solid (80 mg).

MS (EI) 371 (($M^+$); mp>250° C.

Example 67

3-[7-(2-Fluoro-phenyl)-8-methoxy-4-oxo-4,5-dihydro-3H-benzo[b][1,4]diazepin-2-yl]-benzonitrile Prepared from {5-[3-(3-cyano-phenyl)-3-oxo-propionylamino]-2'-fluoro-2-methoxy-biphenyl-4-yl}-carbamic acid tert.-butyl ester (Example O53) by treatment with TFA in $CH_2Cl_2$ according to the general procedure P. Obtained as a light yellow solid (51 mg).

MS (EI) 385 ($M^+$); mp 245–247° C.

Example 68

8-(2-Fluoro-phenyl)-7-methoxy-4-[3-(2-methyl-imidazol-1-yl)-phenyl]-1,3-dihydro-benzo[b][1,4]diazepin-2-one Prepared from (2'-fluoro-2-methoxy-5-{3-[3-(2-methyl-imidazol-1-yl)-phenyl]-3-oxo-propionylamino}-biphenyl-4-yl)-carbamic acid tert.-butyl ester (Example O54) by treatment with TFA in $CH_2Cl_2$ according to the general procedure P. Obtained as a yellow solid (207 mg).

MS (EI) 440 ($M^+$); mp 220–222° C.

Example 69

5-[7-(2-Fluoro-phenyl)-8-methoxy-4-oxo-4,5-dihydro-3H-benzo b][1,4]diazepin-2-yl]-thiophene-2-carbonitrile Prepared from {5-[3-(5-cyano-thiophen-2-yl)-3-oxo-propionylamino]-2'-fluoro-2-methoxy-biphenyl-4-yl}-carbamic acid tert.-butyl ester (Example O55) by treatment with TFA in $CH_2Cl_2$ according to the general procedure P. Obtained as a yellow solid (103 mg).

MS (EI) 391 ($M^+$); mp>250° C.

Example 70

8-(2-Fluoro-phenyl)-7-methoxy-4-(3-[1,2,4]triazol-4-yl-phenyl)-1,3-dihydro-benzo[b][1,4]diazepin-2-one Prepared from {2'-fluoro-2-methoxy-5-[3-oxo-3-(3-[1,2,4]triazol-4-yl-phenyl)-propionylamino]-biphenyl-4-yl}-carbamic acid tert.-butyl ester (Example O56) by treatment with TFA in $CH_2Cl_2$ according to the general procedure P. Obtained as a yellow solid (22 mg).

MS (EI) 427 ($M^+$); mp 188° C. (dec.).

Example 71

4-[7-(2-Fluoro-phenyl)-8-methoxy-4-oxo-4,5-dihydro-3H-benzo[b][1,4]diazepin-2-yl]-pyridine-2-carbonitrile Prepared from {5-[3-(2-cyano-pyridin-4-yl)-3-oxo-propionylamino]-2'-fluoro-2-methoxy-biphenyl-4-yl}-carbamic acid tert.-butyl ester (Example O57) by treatment with TFA in $CH_2Cl_2$ according to the general procedure P. Obtained as a yellow solid (68 mg).

MS (EI) 386 ($M^+$); mp 240–242° C.

Example 72

8-(4-Fluoro-phenyl)-7-hydroxy-4-[3-(2-methyl-imidazol-1 -yl)-phenyl]-1,3-dihydro-benzo[b][1,4]diazepin-2-one Prepared from (2-tert.-butoxy-4'-fluoro-5-{3-[3-(2-methyl-imidazol-1-yl)-phenyl]-3-oxo-propionylamino}- biphenyl-4-yl)-carbamic acid tert.-butyl ester (Example O58) by treatment with TFA in CH$_2$Cl$_2$ according to the general procedure P. Obtained as a yellow solid (49 mg).

MS (ISP) 427 [(M+H)$^+$]; mp 260° C.

Example 73

4-Fluoro-3-[7-(2-fluoro-phenyl)-8-methoxy-4-oxo-4, 5-dihydro-3H-benzo[b][1,4]diazepin-2-yl]- benzonitrile Prepared from {5-[3-(5-cyano-2-fluoro-phenyl)-3-oxo-propionylamino]-2'-fluoro-2-methoxy-biphenyl-4-yl}-carbamic acid tert.-butyl ester (Example O59) by treatment with TFA in CH$_2$Cl$_2$ according to the general procedure P. Obtained as a yellow solid (52 mg).

MS (ISP) 404 [(M+H)$^+$]; mp>250° C.

Example 74

4-[7-(4-Fluoro-phenyl)-8-hydroxy-4-oxo-4,5-dihydro-3H-benzo[b][1,4]diazepin-2-yl]-pyridine-2-carbonitrile Prepared from {2-tert.-butoxy-5-[3-(2-cyano-pyridin-4-yl)-3-oxo-propionylamino]-4'-fluoro-biphenyl-4-yl}-carbamic acid tert.-butyl ester (Example O60) by treatment with TFA in CH$_2$Cl$_2$ according to the general procedure P. Obtained as a yellow solid (24 mg).

MS (EI) 372 (M$^+$); mp 164° C.

Example 75

8-(2-Fluoro-phenyl)-7-hydroxy-4-(3-[1,2,3]triazol-1-yl-phenyl)-1,3-dihydro-benzo[b][1,4]diazepin-2-one Prepared from {2-tert.-butoxy-2'-fluoro-5-[3-oxo-3-(3-[1,2,3]triazol-1-yl-phenyl)-propionylamino]-biphenyl-4-yl}-carbamic acid tert.-butyl ester (Example O61) by treatment with TFA in CH$_2$Cl$_2$ according to the general procedure P. Obtained as a light yellow solid (61 mg).

MS (ISP) 414 [(M+H)$^+$]; mp>250° C.

Example 76

3-[8-(1,4-Dioxa-8-aza-spiro[4.5]dec-8-yl)-7-(2-fluoro-phenyl)-4-oxo-4,5-dihydro-3H-benzo[b][1,4] diazepin-2-yl]-benzonitrile Prepared from [5-[3-(3-cyano-phenyl)-3-oxo-propionylamino]-2-(1,4-dioxa-8-aza-spiro[4.5]dec-8-yl)-2'-fluoro-biphenyl-4-yl]-carbamic acid tert.-butyl ester (Example O62) by treatment with TFA in CH$_2$Cl$_2$ according to the general procedure P. Obtained as a yellow solid (132 mg).

MS (ISP) 497 [(M+H)$^+$]; mp 253° C.

Example 77

7-(1,4-Dioxa-8-aza-spiro[4.5]dec-8-yl)-8-(2-fluoro-phenyl)-4-(3-imidazol-1-yl-phenyl)-1,3-dihydro-benzo[b][1,4]diazepin-2-one Prepared from {2-(1,4-dioxa-8-aza-spiro[4.5]dec-8-yl)-2'-fluoro-5-[3-(3-imidazol-1-yl-phenyl)-3-oxo-propionylamino]-biphenyl-4-yl}-carbamic acid tert.-butyl ester (Example O63) by treatment with TFA in CH$_2$Cl$_2$ according to the general procedure P. Obtained as a yellow solid (133 mg).

MS (ISP) 538 [(M+H)$^+$]; mp 225° C.

Example 78

8-(2-Fluoro-phenyl)-4-(3-imidazol-1-yl-phenyl)-7-(4-oxo-piperidin-1-yl)-1,3-dihydro-benzo[b][1,4] diazepin-2-one Prepared from 7-(1,4-dioxa-8-aza-spiro[4.5]dec-8-yl)-8-(2-fluoro-phenyl)-4-(3-imidazol-1-yl-phenyl)-1,3-dihydro-benzo[b][1,4]diazepin-2-one (Example 77) (54 mg, 0.1 mmol) by stirring in 1N HCl (1 mL) and acetone (1 mL) at 23° C. for 44 h. Obtained as a yellow solid (39 mg).

MS (EI) 493 (M$^+$); mp 230° C.

Example 79

8-(2-Fluoro-phenyl)-7-hydroxy-4-[3-(2-methyl-imidazol-1-yl)-phenyl]-1,3-dihydro-benzo[b][1,4] diazepin-2-one Prepared from (2-tert.-butoxy-2'-fluoro-5-{3-[3-(2-methyl-imidazol-1-yl)-phenyl]-3-oxo-propionylamino}-biphenyl-4-yl)-carbamic acid tert.-butyl ester (Example O64) by treatment with TFA in CH$_2$Cl$_2$ according to the general procedure P. Obtained as a yellow solid (111 mg).

MS (ISN) 425 [(M−H)$^-$]; mp>250° C.

Example 80

4-[7-(2-Fluoro-phenyl)-8-hydroxy-4-oxo-4,5-dihydro-3H-benzo[b][1,4]diazepin-2-yl]-pyridine-2-carbonitrile Prepared from {2-tert.-butoxy-5-[3-(2-cyano-pyridin-4-yl)-3-oxo-propionylamino]-2'-fluoro-biphenyl-4-yl}-carbamic acid tert.-butyl ester (Example O65) by treatment with TFA in CH$_2$Cl$_2$ according to the general procedure P. Obtained as a yellow solid (47 mg).

MS (ISN) 371 [(M−H)$^-$]; mp>250° C.

Example 81

8-(2-Fluoro-phenyl)-7-hydroxy-4-[3-(2-methylsulfanyl-imidazol-1-yl)-phenyl]-1,3-dihydro-benzo[b][1,4]diazepin-2-one Prepared from (2-tert.-butoxy-2'-fluoro-5-{3-[3-(2-methylsulfanyl-imidazol-1-yl)-phenyl]-3-oxo-propionylamino}-biphenyl-4-yl)-carbamic acid tert.-butyl ester (Example O66) by treatment with TFA in CH$_2$Cl$_2$ according to the general procedure P. Obtained as a light yellow solid (148 mg).

MS (ISN) 457 [(M−H)$^-$]; mp>250° C.

Example 82

3-[7-(2,5-Difluoro-phenyl)-8-methoxy-4-oxo-4,5-dihydro-3H-benzo[b][1,4]diazepin-2-yl]-benzonitrile Prepared from {5-[3-(3-cyano-phenyl)-3-oxo-propionylamino]-2',5'-difluoro-2-methoxy-biphenyl-4-yl}-carbamic acid tert.-butyl ester (Example O67) by treatment with TFA in CH$_2$Cl$_2$ according to the general procedure P. Obtained as a yellow solid (49 mg).

MS (EI) 403 (M$^+$); mp 251° C.

Example 83

8-(2,5-Difluoro-phenyl)-7-methoxy-4-(3-[1,2,3 ]triazol-1-yl-phenyl)-1,3-dihydro-benzo[b][1,4] diazepin-2-one Prepared from {2',5'-difluoro-2-methoxy-5-[3-oxo-3-(3-[1,2,3]triazol-1-yl-phenyl)-propionylamino]-biphenyl-4- yl}-carbamic acid tert.-butyl ester (Example O68) by treatment with TFA in $CH_2Cl_2$ according to the general procedure P. Obtained as a yellow solid (78 mg).

MS (EI) 445 ($M^+$); mp 241° C.

Example 84

2-[7-(2-Fluoro-phenyl)-8-hydroxy-4-oxo-4,5-dihydro-1H-benzo[b][1,4]diazepin-2yl]-thiophene-3-carbonitrile Prepared from {2-tert.-butoxy-5-[3-(3-cyano-thiophen-2-yl)-3-oxo-propionylamino]-2'-fluoro-biphenyl-4-yl}-carbamic acid tert.-butyl ester (Example O69) by treatment with TFA in $CH_2Cl_2$ according to the general procedure P. Obtained as an orange solid (82 mg).

MS (ISN) 376 [$(M-H)^-$]; mp 242° C.

Example 85

5-[7-(2-Fluoro-phenyl)-8-hydroxy-4-oxo-4,5-dihydro-3H-benzo[b][1,4]diazepin-2-yl]-thiophene-2-carbonitrile Prepared from {2-tert.-butoxy-5-[3-(5-cyano-thiophen-2-yl)-3-oxo-propionylamino]-2'-fluoro-biphenyl-4-yl}-carbamic acid tert.-butyl ester (Example O70) by treatment with TFA in $CH_2Cl_2$ according to the general procedure P. Obtained as a yellow solid (126 mg).

MS (EI) 377 ($M^+$); mp.

Example 86

8-(4-Fluoro-phenyl)-7-hydroxy-4-(3-[1,2,3]triazol-1-yl-phenyl)-1,3-dihydro-benzo[b][1,4]diazepin-2-one Prepared from {2-tert.-butoxy-4'-fluoro-5-[3-oxo-3-(3-[1,2,3]triazol-1-yl-phenyl)-propionylamino]-biphenyl-4-yl}-carbamic acid tert.-butyl ester (Example O71) by treatment with TFA in $CH_2Cl_2$ according to the general procedure P. Obtained as a yellow solid (78 mg).

MS (ISP) 414 [$(M+H)^+$]; mp>250° C.

Example 87

3-[7-(2-Fluoro-phenyl)-8-(2-methoxy-ethoxy)-4-oxo-4,5-dihydro-3H-benzo[b][1,4]diazepin-2-yl]-benzonitrile Prepared from [5-[3-(3-cyano-phenyl)-3-oxo-propionylamino]-2'-fluoro-2-(2-methoxy-ethoxy)-biphenyl-4-yl]-carbamic acid tert.-butyl ester (Example O72) by treatment with TFA in $CH_2Cl_2$ according to the general procedure P. Obtained as a light yellow solid (141 mg).

MS (EI) 429 ($M^+$); mp 211–213° C.

Example 88

3-[7-(2-Fluoro-phenyl)-8-hydroxymethyl-4-oxo-4,5-dihydro-3H-benzo[b][1,4]diazepin-2-yl]-benzonitrile Prepared from (RS)-[5-[3-(3-cyano-phenyl)-3-oxo-propionylamino]-2'-fluoro-2-(tetrahydro-pyran-2-yloxymethyl)-biphenyl-4-yl]-carbamic acid tert.-butyl ester (Example O73) by treatment with TFA in $CH_2Cl_2$ according to the general procedure P. Obtained as a light yellow solid (69 mg).

MS (EI) 385 ($M^+$); mp 90–91° C.

Example 89

8-(2-Fluoro-phenyl)-7-hydroxy-4-[3-(3-methyl-isoxazol-5-yl)-phenyl]-1,3-dihydro-benzo[b][1,4]diazepin-2-one Prepared from (2'-fluoro-2-(4-methoxy-benzyloxy)-5-{3-[3-(3-methyl-isoxazol-5-yl)-phenyl]-3-oxo-propionylamino}-biphenyl-4-yl)-carbamic acid tert.-butyl ester (Example O74) by treatment with TFA in $CH_2Cl_2$ according to the general procedure P. Obtained as a yellow solid (278 mg).

MS (ISP) 428 $(M+H)^+$; mp 237° C.

Example 90

3-[7-(2,5-Difluoro-phenyl)-8-hydroxy-4-oxo-4,5-dihydro-3H-benzo[b][1,4]diazepin-2-yl]-benzonitrile Prepared from {2-tert.-butoxy-5-[3-(3-cyano-phenyl)-3-oxo-propionylamino]-2',5'-diflouro-biphenyl-4-yl}-carbamic acid tert.-butyl ester (Example O75) by treatment with TFA in $CH_2Cl_2$ according to the general procedure P. Obtained as a yellow solid (56 mg).

MS (ISP) 390 $(M+H)^+$; mp>250° C.

Example 91

8-(4-Fluoro-phenylethynyl)-7-hydroxy-4-(3-imidazol-1-yl-phenyl)-1,3-dihydro-benzo[b][1,4]diazepin-2-one Prepared from {5-tert.-butoxy-4-(4-fluoro-phenylethynyl)-2-[3-(3-imidazol-1-yl-phenyl)-3-oxo-propionylamino]-phenyl}-carbamic acid tert.-butyl ester (Example O76) by treatment with TFA in $CH_2Cl_2$ according to the general procedure P. Obtained as a yellow solid (55 mg).

MS (EI) 436 ($M^+$); mp 247° C.

Example 92

8-(4-Fluoro-phenylethynyl)-7-hydroxy-4-(3-[1,2,3]triazol-1-yl-phenyl)-1,3-dihydro-benzo[b][1,4]diazepin-2-one Prepared from {5-tert.-butoxy-4-(4-fluoro-phenylethynyl)-2-[3-oxo-3-(3-[1,2,3]triazol-1-yl-phenyl)-propionylamino]-phenyl}-carbamic acid tert.-butyl ester (Example O77) by treatment with TFA in $CH_2Cl_2$ according to the general procedure P. Obtained as a yellow solid (56 mg).

MS (EI) 437 ($M^+$); mp 243° C.

The following examples exemplify, that the 4-aryl-8-iodo-1,3-dihydro-benzo[b][1,4]diazepin-2-ones could also serve as starting material for the Sonogashira-coupling as illustrated in synthetic scheme G.

Example 93

3-(4-Oxo-7-phenylethynyl-8-thiomorpholin-4-yl-4,5-dihydro-3H-benzo[b][1,4]diazepin-2-yl)-benzonitrile Prepared from 3-(7-iodo-4-oxo-8-thiomorpholin-4-yl-4,5-dihydro-3H-benzo[b][1,4]diazepin-2-yl)-benzonitrile (Example 1) (437 mg, 0.895 mmol) and phenylacetylene (0.15 mL, 1.34 mmol) according to the general procedure K. Obtained as a curry solid (334 mg).

MS (EI) 391 ($M^+$); mp 234–235° C. (dec.).

Example 94

(RS)-3-[4-Oxo-8-(1-oxo-thiomorpholin-4-yl)-7-phenylethynyl-4,5-dihydro-3H-benzo[b][1,4]diazepin-2-yl]-benzonitrile A mixture of 3-(4-oxo-7-phenylethynyl-8-thiomorpholin-4-yl-4,5-dihydro-3H-benzo[b][1,4]diazepin-2-yl)- benzonitrile (Example 27) (50 mg, 0.180 mmol) and Davis-reagent (116 mg, 0.432 mmol) in DCM (4.5 mL) was stirred at 23° C. for 1 h. The product was filtered off and washed with DCM. Obtained as a light yellow solid (16 mg).

MS (ISP) 479 [(M+H)$^+$] and 501 [(M+Na)$^+$]; mp>250° C. (dec.).

Palladium-catalyzed carbonylation of the 4-(3-iodophenyl)-8-phenylethynyl-1,3-dihydro-benzo[b][1,4]diazepin-2-one in the presence of secondary amines leads directly to the corresponding amides as shown in synthetic scheme I.

Example 95

3-[8-(2-Methoxy-ethoxy)-4-oxo-7-phenylethynyl-4,5-dihydro-3H-benzo[b][1,4]diazepin 2-yl]-benzamide Prepared from 4-(3-iodo-phenyl)-7-(2-methoxy-ethoxy)-8-phenylethynyl-1,3-dihydro-benzo[b][1,4]diazepin-2-one (Example 25) (268 mg, 0.5 mmol) and hexamethyldisilazane (0.52 mL, 2.5 mmol) according to the general procedure Q. Obtained as a yellow solid (102 mg).

MS (EI) 453 ((M$^+$); mp 227–230° C. (dec.).

Example I

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:
1. A compound of the formula

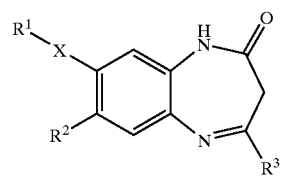

I wherein
X is a single bond or an ethynediyl group, wherein,
when X is a single bond, R$^1$ is halogen or phenyl which is optionally substituted with halogen, lower alkyl, halo-lower alkyl, lower alkoxy, halo-lower alkoxy, or cyano; or
when X is an ethynediyl group, R$^1$ is unsubstituted phenyl, or phenyl substituted with halogen, lower alkyl, halo-lower alkyl, lower cycloalkyl, lower alkoxy or halo-lower alkoxy;
R$^2$ is halogen, hydroxy, lower alkyl, lower halo-alkyl, lower alkoxy, hydroxymethyl, hydroxyethoxy, lower alkoxy-(ethoxy)$_n$(n=1 to 4), lower alkoxymethyl, cyanomethoxy, morpholine-4-yl, thiomorpholine-4-yl, 1-oxothiomorpholine-4-yl, 1,1-dioxothiomorpholine-4-yl, 4-oxo-piperidine-1-yl, 4-alkoxy-piperidine-1-yl, 4-hydroxy-piperidine-1-yl, 4-hydroxyethoxy-piperidine-1-yl, 4-lower alkyl-piperazine-1-yl, alkoxycarbonyl, 2-dialkylamino-ethylsulfanyl-, N,N-bis lower alkylamino lower alkyl; carbamoylmethyl; alkylsulfonyl; lower alkoxycarbonyl-lower alkyl, alkylcarboxy-lower alkyl, carboxy-lower alkyl, alkoxycarbonylmethylsulfanyl, carboxymethylsulfanyl, 1,4-dioxa-8-aza-spiro[4,5]dec-8-yl, carboxy-lower alkoxy, cyano-lower alkyl, 2,3-dihydroxy-lower alkoxy, carbamoylmethoxy, 2-oxo-[1,3]-dioxolan-4-yl-lower alkoxy, (2-hydroxy-lower alkyl)-lower alkyl amino, hydroxycarbamoyl-lower alkoxy, 2,2-dimethyl-tetrahydro-[1,3]dioxolo[4,5c]-pyrrol-5-yl, lower alkoxy-carbamoyl-lower alkoxy, 3 R-hydroxy-pyrrolidin-1-yl, 3,4-dihydroxy-pyrrolidin-1-yl, 2-oxo-oxazolidin-3-yl, lower alkyl-carbamoylmethoxy, or aminocarbamoyl-lower alkoxy; and
R$^3$ is an unsubstituted 5 or 6 membered aryl or heteroaryl or a substituted 5 or 6 membered aryl or heteroaryl with a substituent selected from the group consisting of halogen, cyano, nitro, azido, hydroxy, carboxy, morpholine-4-carbonyl, carbamoyl, thiocarbamoyl, N-hydroxycarbamoyl, trimethylsilyl-ethynyl, lower alkyl, lower alkoxy, halo-lower alkyl, 4-lower alkyl-piperazine-1-carbonyl, unsubstituted lower alkylcarbamoyl or lower alkylcarbamoyl substituted by amino, lower alkylamino, acylamino, oxo, hydroxy, lower alkoxy, lower alkylthio, unsubstituted carboxy or an esterified or amidated carboxy, unsubstituted five-membered aromatic heterocycle, or a five-membered aromatic heterocycle substituted by amino, lower alkylamino, acylamino, oxo, hydroxy, lower alkoxy, lower alkylthio, unsubstituted carboxy or an esterified or amidated carboxy, unsubstituted lower alkyl or a lower alkyl substituted by halogen, amino, lower alkylamino, acylamino, hydroxy, lower alkoxy, lower alkylthio, acyloxy, lower alkenoyl, lower alkylsulfinyl, lower alkylsulfonyl, cycloalkylsulfinyl, cycloalkylsulfonyl, hydroxyimino, alkoxyimino, unsubstituted carboxy or an esterified or amidated carboxy, lower alkenyl, oxo, cyano, carbamoyloxy, unsubstituted sulfamoyl or sulfamoyl substituted by lower alkyl, and unsubstituted amidino or amidino substituted by lower alkyl, -C(NRR')=NR" (where R, R' and R" are hydrogen or lower alkyl), or a pharmaceutically acceptable addition salt thereof.

2. The compound according to claim 1, wherein $R^3$ is phenyl substituted in the meta position by a substituent selected from the group consisting of cyano, halogen, unsubstituted imidazolyl or imidazolyl substituted by lower alkyl or methylsulfanyl, 1,2,3-triazolyl, 1,2,4-triazolyl, unsubstituted isoxazolyl and isoxazolyl substituted by lower alkyl.

3. The compound according to claim 2, selected from the group consisting of 3-(8-Chloro-4-oxo-7-phenylethynyl-4,5-dihydro-3H-benzo[b](1,4]diazepin-2-yl)-benzonitrile;
3-[8-(4-Methyl-piperazin-1-yl)-4-oxo-7-phenylethynyl-4,5-dihydro-3H-benzo[b][1,4]diazepin-2-yl]-benzonitrile;
3-(8-Chloro-4-oxo-7-phenyl-4,5-dihydro-3H -benzo[b][1,4]diazepin-2-yl)-benzonitrile;
[4-(3-Cyano-phenyl)-2-oxo-8-phenylethynyl-2,3-dihydro-1H-benzo[b ][1,4]diazepin-7-ylsulfanyl]-acetic acid methyl ester;
2-[4-(3-Cyano-phenyl)-2-oxo-8-phenylethynyl-2,3-dihydro-1H-benzo[b][1,4]diazepin-7-yl]-acetamide;
3-(8-Methoxy-4-oxo-7-phenylethynyl-4,5-dihydro-3H-benzo[b][1,4]diazepin-2-yl)-benzonitrile;
3-(8-Cyanomethyl-4-oxo-7-phenylethynyl-4,5-dihydro-3H-benzo[b][1,4]diazepin-2-yl)-benzonitrile;
4-(3-Iodo-phenyl)-7-(2-methoxy-ethoxy)-8-phenylethynyl-1,3-dihydro-benzo[b][1,4]diazepin-2-one;
4-(3-Imidazol-1-yl-phenyl)-7-(2-methoxy-ethoxy)-8-phenylethynyl-1,3-dihydro-benzo[b][1,4]diazepin-2-one;
[RS]-3-[4-Oxo-8-(2-oxo-[1,3]dioxolan-4-ylmethoxy)-7-phenylethynyl-4,5-dihydro3H-benzo[b][1,4]diazepin-2-yl]-benzonitrile;
7-Hydroxymethyl-4-(3-imidazol-1-yl-phenyl)-8-phenylethynyl-1,3-dihydro-benzo[b][1,4]diazepin-2-one;
[4-(3-Imidazol-1-yl-phenyl)-2-oxo-8-phenylethynyl-2,3-dihydro-1H-benzo[b][1,4]diazepin-7-yloxy]-acetonitrile;
8-(4-Fluoro-phenylethynyl)-7-hydroxymethyl-4-(3-imidazol-1-yl-phenyl)-1,3-dihydro-benzo[b][1,4] diazepin-2-one;
7-(2-Hydroxy-ethoxy)-4-(3-imidazol-1-yl-phenyl)-8-phenylethynyl-1,3-dihydro-benzo[b][1,4]diazepin-2-one;
8-(4-Fluoro-phenyl)-7-[4-(2-hydroxy-ethoxy)-piperidin-1-yl]-4-(3-imidazol-1-yl-phenyl)-1,3-dihydro-benzo[b][1,4]diazepin-2-one;
8-(4-Fluoro-phenyl)-7-hydroxy-4-(3-imidazol-1-yl-phenyl)-1,3-dihydro-benzo[b][1,4]diazepin-2-one;
8-(2-Fluoro-phenyl)-7-methoxy-4-[3-(2-methyl-imidazol-1-yl)-phenyl]-1,3-dihydro-benzo[b][1,4]diazepin-2-one;
8-(2-Fluoro-phenyl)-7-hydroxy-4-(3-[1,2,3 ]triazol-1-yl-phenyl)-1,3-dihydro-benzo[b][1,4]diazepin-2-one;
8-(2-Fluoro-phenyl)-7-hydroxy-4-[3-(2-methyl-imidazol-1-yl)-phenyl]-1,3-dihydro-benzo[b][1,4]diazepin-2-one;
8-(2-Fluoro-phenyl)-7-hydroxy-4-[3-(2-methylsulfanyl-imidazol-1-yl)-phenyl]-1,3-dihydro-benzo[b][1,4] diazepin-2-one;
8-(2,5-Difluoro-phenyl)-7-methoxy-4-(3-[1,2,3]triazol-1-yl-phenyl)-1,3-dihydro-benzo[b][1,4]diazepin-2-one;
8-(2-Fluoro-phenyl)-7-hydroxy-4-[3-(3-methyl-isoxazol-5-yl)-phenyl]-1,3-dihydro-benzo[b][1,4]diazepin-2-one;
3-[7-(2,5-Difluoro-phenyl)-8-hydroxy-4-oxo-4,5-dihydro-3H-benzo[b][1,4]diazepin-2-yl]-benzonitrile;
8-(4-Fluoro-phenylethynyl)-7-hydroxy-4-(3-imidazol-1-yl-phenyl)-1,3-dihydro-benzo[b][1,4]diazepin-2-one; and
8-(4-Fluoro-phenylethynyl)-7-hydroxy-4-(3-[1,2,3]triazol-1-yl-phenyl)-1,3-dihydro-benzo[b][1,4]diazepin-2-one.

4. The compound according to claim 1, wherein $R^3$ is unsubstituted thiophenyl, or thiophenyl substituted by a substituent selected from the group consisting of cyano, halogen, unsubstituted pyridinyl, pyridinyl substituted in 2-position by cyano or halogen, unsubstituted thiazolyl and thiazolyl substituted in 2-position with imidazolyl or 4-methylimidazolyl.

5. The compound according to claim 4, selected from the group consisting of 5-(7-(2-Fluoro-phenyl)-8-methoxy-4-oxo-4,5-dihydro-3H-benzo[b][1,4]diazepin-2-yl]-thiophene-2-carbonitrile;
2-[7-(2-Fluoro-phenyl)-8-hydroxy-4-oxo-4,5-dihydro-1H-benzo[b]1,4]diazepin-2-yl]-thiophene-3-carbonitrile;
4-[7-(2-Fluoro-phenyl)-8-methoxy-4-oxo-4,5-dihydro-3H-benzo[b][1,4]diazepin-2yl]-pyridine-2-carbonitrile;
4-[7-(4-Fluoro-phenyl)-8-hydroxy-4-oxo-4,5-dihydro-3H-benzo[b][1,4]diazepin-2-yl]-pyridine-2-carbonitrile;
4-[7-(2-Fluoro-phenyl)-8-hydroxy-4-oxo-4,5-dihydro-3H-benzo[b][1,4]diazepin-2-yl]-pyridine-2-carbonitrile; and
8-(2-Fluoro-phenyl)-4-[2-(4-methyl-imidazol-1-yl)-thiazol-4-yl]-1,3-dihydro-benzo[b][1,4]diazepin-2-one.

6. A pharmaceutical composition comprising at least one compound claimed in claim 1 and pharmaceutically acceptable excipients.

7. A process for preparing a compound according to claim 1, comprising reacting a compound of formula II:

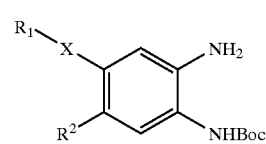

where $R^1$, $R^2$ and X are as set forth in claim 1, with a compound of formula IV or IVa:
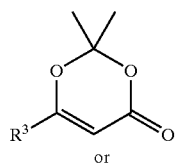
IV
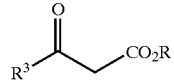
IVa
wherein R is ethyl or butyl, and $R^3$ is as set forth in claim 1, thereby yielding the compound of formula III:
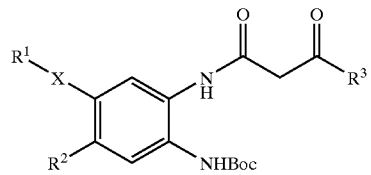
III
subsequently deprotecting the amino group of the compound of formula III; and then cyclizing the deprotected amino compound to obtain a compound of formula I of claim 1.
* * * * *